(12) United States Patent
Pajouhesh et al.

(10) Patent No.: US 9,688,615 B2
(45) Date of Patent: Jun. 27, 2017

(54) BENZIMIDAZOLE INHIBITORS OF THE SODIUM CHANNEL

(71) Applicant: Mark G. DeGiacomo, Boston, MA (US)

(72) Inventors: Hassan Pajouhesh, West Vancouver (CA); Richard Holland, Vancouver (CA); Lingyun Zhang, Vancouver (CA); Hossein Pajouhesh, Coquitlam (CA); Jason Lamontagne, Burnaby (CA); Brendan Whelan, Vancouver (CA)

(73) Assignee: DEGIACOMO, INTERIM TRUSTEE, MARK G., Boston, MA (US)

(*) Notice: Subject to any disclaimer, the term of this patent is extended or adjusted under 35 U.S.C. 154(b) by 0 days.

(21) Appl. No.: 14/833,601

(22) Filed: Aug. 24, 2015

(65) Prior Publication Data
US 2015/0361032 A1 Dec. 17, 2015

Related U.S. Application Data

(62) Division of application No. 14/002,943, filed as application No. PCT/CA2012/000193 on Mar. 2, 2012, now abandoned.

(60) Provisional application No. 61/448,923, filed on Mar. 3, 2011, provisional application No. 61/448,910, filed on Mar. 3, 2011.

(51) Int. Cl.
| | |
|---|---|
| *C07D 207/16* | (2006.01) |
| *C07D 205/04* | (2006.01) |
| *C07D 265/30* | (2006.01) |
| *C07D 231/14* | (2006.01) |
| *C07D 211/60* | (2006.01) |
| *C07C 237/04* | (2006.01) |
| *C07C 237/06* | (2006.01) |
| *C07C 237/22* | (2006.01) |
| *C07C 237/24* | (2006.01) |
| *C07D 235/14* | (2006.01) |
| *C07D 401/04* | (2006.01) |
| *C07D 403/04* | (2006.01) |
| *C07D 403/06* | (2006.01) |
| *C07D 413/04* | (2006.01) |
| *C07D 401/12* | (2006.01) |
| *C07D 413/06* | (2006.01) |
| *C07D 241/08* | (2006.01) |

(52) U.S. Cl.
CPC .......... *C07C 237/06* (2013.01); *C07C 237/04* (2013.01); *C07C 237/22* (2013.01); *C07C 237/24* (2013.01); *C07D 205/04* (2013.01); *C07D 207/16* (2013.01); *C07D 211/60* (2013.01); *C07D 231/14* (2013.01); *C07D 235/14* (2013.01); *C07D 241/08* (2013.01); *C07D 265/30* (2013.01); *C07D 401/04* (2013.01); *C07D 401/12* (2013.01); *C07D 403/04* (2013.01); *C07D 403/06* (2013.01); *C07D 413/04* (2013.01); *C07D 413/06* (2013.01); *C07C 2101/02* (2013.01); *C07C 2101/14* (2013.01)

(58) Field of Classification Search
CPC .. C07D 207/16; C07D 205/04; C07D 265/30; C07D 231/14; C07D 211/60; C07C 237/04; C07C 237/06
See application file for complete search history.

(56) References Cited

U.S. PATENT DOCUMENTS

| | | | |
|---|---|---|---|
| 3,271,249 A | 9/1966 | Clegg et al. | |
| 3,655,901 A | 4/1972 | Jensen et al. | |
| 5,585,385 A * | 12/1996 | Natsugari | C07D 401/04 514/299 |
| 7,655,693 B2 | 2/2010 | Alvaro et al. | |

(Continued)

FOREIGN PATENT DOCUMENTS

| | | |
|---|---|---|
| CA | 2431592 A1 | 6/2002 |
| CA | 2646755 A1 | 10/2007 |

(Continued)

OTHER PUBLICATIONS

PubChem CID 11097669—National Center for Biotechnology Information. PubChem Compound Database; CID=11097669, http://pubchem.ncbi.nlm.nih.gov/summary/summary.cgi?cid=11097669 (accessed Jan. 21, 2016), create date Oct. 26, 2006.*

PubChem CID 24700018—National Center for Biotechnology Information. PubChem Compound Database; CID=24700018, http://pubchem.ncbi.nlm.nih.gov/summary/summary.cgi?cid=24700018 (accessed Jan. 21, 2016), create date Feb. 29, 2008.*

PubChem CID 43226784—National Center for Biotechnology Information. PubChem Compound Database; CID=43226784, http://pubchem.ncbi.nlm.nih.gov/summary/summary.cgi?cid=43226784 (accessed Jan. 21, 2016), create date Jul. 21, 2009.*

PubChem CID 44413156—National Center for Biotechnology Information. PubChem Compound Database; CID=44413156, http://pubchem.ncbi.nlm.nih.gov/summary/summary.

(Continued)

*Primary Examiner* — Laura L. Stockton
(74) *Attorney, Agent, or Firm* — One3 IP Management, P.C.; Annette S. Parent; Peter D. Weinstein

(57) ABSTRACT

The invention relates to compounds useful in treating conditions associated with voltage-gated ion channel function, particularly conditions associated with sodium channel activity. More specifically, the invention concerns compounds (e.g., compounds according to any of Formulas (I)-(XIII) or Compounds (1)-(236) of Table 1) that are useful in treatment of a variety of diseases and conditions.

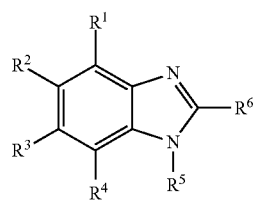

(I)

6 Claims, 11 Drawing Sheets

(56) References Cited

U.S. PATENT DOCUMENTS

| | | | |
|---|---|---|---|
| 7,932,282 B2 | 4/2011 | Beswick et al. | |
| 8,153,623 B2 | 4/2012 | Alvaro et al. | |
| 8,153,681 B2 | 4/2012 | Alvaro et al. | |
| 2005/0250814 A1* | 11/2005 | Zhou | C07D 205/04 514/323 |
| 2006/0025438 A1* | 2/2006 | Salter-Cid | A61K 31/135 514/303 |
| 2006/0089316 A1 | 4/2006 | Brown et al. | |
| 2008/0280969 A1 | 11/2008 | Alvaro et al. | |
| 2010/0105754 A1 | 4/2010 | Alvaro et al. | |
| 2010/0130583 A1 | 5/2010 | Alvaro et al. | |

FOREIGN PATENT DOCUMENTS

| | | |
|---|---|---|
| CA | 2736970 A1 | 3/2010 |
| CA | 2746943 A1 | 7/2010 |
| EP | 0398059 A1 | 11/1990 |
| FR | 2104717 A1 | 4/1972 |
| WO | WO-93/01160 A1 | 1/1993 |
| WO | WO-93/01169 A1 | 1/1993 |
| WO | WO-94/08456 A1 | 4/1994 |
| WO | WO-94/19320 A1 | 9/1994 |
| WO | WO-96/31214 A1 | 10/1996 |
| WO | WO-02/08224 A1 | 1/2002 |
| WO | WO-2005/042497 A2 | 5/2005 |
| WO | WO-2007/070947 A1 | 6/2007 |
| WO | WO-2007/117399 A2 | 10/2007 |
| WO | WO-2007/118853 A1 | 10/2007 |
| WO | WO-2008/008398 A2 | 1/2008 |
| WO | WO-2008/056150 A1 | 5/2008 |
| WO | WO-2008/076752 A1 | 6/2008 |
| WO | WO-2008/119825 A2 * | 10/2008 |
| WO | WO-2010/074193 A1 | 7/2010 |
| WO | WO-2011/001115 A1 | 1/2011 |
| WO | WO-2011/026241 A1 | 3/2011 |

OTHER PUBLICATIONS cgi?cid=44413156 (accessed Jan. 21, 2016), create date Nov. 19, 2009.*
Chemical Abstracts Registry No. 862997-42-0, indexed in the Registry file on STN CAS Online Sep. 13, 2005.*
Chemical Abstracts Registry No. 688025-17-4, indexed in the Registry file on STN CAS Online Jun. 1, 2004.*
Chemical Abstracts Registry No. 693245-75-9, indexed in the Registry file on STN CAS Online Jun. 15, 2004.*
Chemical Abstracts Registry No. 885679-26-5, indexed in the Registry file on STN CAS Online May 26, 2006.*
Brooke et al., "Aromatic polyfluoro-compounds. Part VII. The reaction of pentafluoronitrobenzene with ammonia," J Chem Soc. 802-807 (1961).
Charles et al., "Synthesis of 2,5-disubstituted benzimidazoles as potential antihookworm and antimicrobial agents," Eur J Med Chem. 14(5):435-8 (1979).
Chemical Abstracts Registry No. 825616-92-0, indexed in the Registry file on STN CAS Online Feb. 4, 2005 (1 page).
Database accession No. 1965:58912, accessed Dec. 11, 2014 (abstract only) (2 pages).
Database accession No. 2006:365240, accessed on Dec. 11, 2014 (abstract only) (2 pages).
Göker et al., "Synthesis of 1,2,5(6)-trisubstituted benzimidazoles and evaluation of their antimicrobial activities," Arch Pharm (Weinheim). 328(5):425-30 (1995).
International Preliminary Report on Patentability for International Patent Application No. PCT/CA2012/000193, mailed Sep. 12, 2013 (10 pages).
International Search Report for International Application No. PCT/CA2012/000193, mailed Jun. 29, 2012 (7 pages).
Louvet et al., "Novel benzimidazoles as ligands for the strychnine-insensitive N-methyl-D-aspartate-linked glycine receptor," Eur J Med Chem. 28:71-75 (1993).
Oksuzoglu et al., "A study on the genotoxic activities of some new benzoxazoles," Med Chem Res. 16:1-14 (2007).
Ören et al., "Synthesis and antimicrobial activity of some novel 2,5- and/or 6-substituted benzoxazole and benzimidazole derivatives." Eur J Pharm Sci. 7(2):153-60 (1998).
PubChem CID 21484168. National Center for Biotechnology Information. PubChem Compound Database, <https://pubchem.ncbi.nlm.nih.gov/compound/21484168> retrieved on Nov. 27, 2015 (11 pages).
Supplementary Partial European Search Report for European Application No. 12751899.1, mailed Dec. 15, 2014 (12 pages).
Zou et al., "Design, synthesis, and antiviral evaluation of 2-substituted 4,5-dichloro- and 4,6-dichloro-1-beta-D-ribofuranosylbenzimidazoles as potential agents for human cytomegalovirus infections," J Med Chem. 40(5):802-10 (1997).
Saczewski et al., "Studies of benzimidazole derivatives. XIII. Synthesis of various 2-alpha-hydroxy- and 2-beta-hydroxyalkyl-benzimidazoles," Acta Pol Pharm. 43(4):299-307 (1986) (English abstract included).
Extended European Search Report for European Application No. 15195678.6, dated Feb. 26, 2016 (10 pages).

* cited by examiner

FIG. 1A

Modulation of ion channels by compounds of the invention

| No. | Conc. (nM) | Shift in V₁/₂ (mV) | Change in P2/P1 at 20 mV | Cav2.2 IC50 closed-state (nM) | Cav2.2 IC50 inactivated-state (nM) | Cav3.1 IC50 (nM) | Cav3.2 IC50 closed-state (nM) | Cav3.2 IC50 inactivated-state (nM) | Cav1.2 IC50 closed-state (nM) | Cav1.2 IC50 Inactivated-state (nM) | hERG, % inh. @ 3 µM | Nav1.5 IC50 (nM) |
|---|---|---|---|---|---|---|---|---|---|---|---|---|
| 1 | 30000 | -12.7 | -0.08 | >10000 | 6380 | 60 | 7260 | 1980 | >10000 | 4240 | 31 | >10000 |
| 2 | 30000 | -2.4 | 0.01 | >10000 | >10000 | 1980 | 4570 | 2230 | >10000 | >10000 | | |
| 3 | 30000 | -2.9 | -0.06 | >10000 | >10000 | 900 | 1850 | 670 | >10000 | >10000 | 13 | |
| 5 | 30000 | -3.9 | -0.04 | >10000 | >10000 | >10000 | >10000 | >10000 | >10000 | >10000 | | |
| 10 | 30000 | -9.2 | -0.15 | >10000 | >10000 | 150 | 290 | 80 | >10000 | 4300 | 26 | |
| 11 | 30000 | -3.2 | -0.02 | >10000 | >10000 | >10000 | >10000 | 2400 | >10000 | >10000 | | |
| 12 | 30000 | -5 | -0.02 | >10000 | >10000 | 8590 | >10000 | 4580 | >10000 | >10000 | | |
| 13 | 30000 | -2.6 | -0.03 | >10000 | >10000 | >10000 | >10000 | 5290 | >10000 | >10000 | | |
| 14 | 30000 | -0.8 | -0.02 | >10000 | >10000 | >10000 | >10000 | 1760 | >10000 | >10000 | | |
| 15 | 30000 | -4.9 | -0.06 | >10000 | >10000 | >10000 | >10000 | 5480 | >10000 | >10000 | | |
| 19 | 30000 | -7.1 | -0.21 | 7990 | 2940 | 4.5 | 530 | 40 | 6120 | 3560 | 81 | >10000 |
| 20 | 30000 | -15.6 | -0.35 | >10000 | 1130 | 20 | 60 | 30 | 3900 | 2580 | 109 | |
| 21 | 30000 | -5.8 | -0.05 | >10000 | >10000 | >10000 | >10000 | >10000 | >10000 | >10000 | | |
| 23 | 30000 | -11.8 | -0.06 | >10000 | >10000 | 7520 | >10000 | >10000 | >10000 | >10000 | 26 | >10000 |
| 24 | 30000 | -12.1 | -0.12 | >10000 | >10000 | >10000 | >10000 | 3090 | >10000 | >10000 | 28 | >10000 |
| 26 | 30000 | -4.8 | 0 | >10000 | >10000 | >10000 | >10000 | >10000 | >10000 | >10000 | | |
| 28 | 30000 | -3.4 | -0.02 | >10000 | >10000 | >10000 | >10000 | >10000 | >10000 | >10000 | | |
| 29 | 30000 | -10.8 | -0.09 | >10000 | 7020 | >10000 | >10000 | >10000 | >10000 | >10000 | | |
| 30 | 30000 | -9.4 | -0.18 | >10000 | 8440 | >10000 | >10000 | >10000 | >10000 | >10000 | | |
| 31 | 30000 | -25.8 | -0.27 | >10000 | 4160 | >10000 | 7580 | 1260 | >10000 | 2990 | 60 | 3700 |
| 32 | 30000 | -10.3 | -0.07 | >10000 | 6160 | >10000 | >10000 | 290 | >10000 | 8120 | | |

FIG. 1A (continued)

Modulation of Ion channels by compounds of the invention

| No. | Conc. (nM) | Shift in $V_{1/2}$ (mV) | Change in P2/P1 at 20 mV | Cav2.2 IC50 closed-state (nM) | Cav2.2 IC50 inactivated-state (nM) | Cav3.1 IC50 (nM) | Cav3.2 IC50 closed-state (nM) | Cav3.2 IC50 inactivated-state (nM) | Cav1.2 IC50 closed-state (nM) | Cav1.2 IC50 inactivated-state (nM) | hERG, % inh. @ 3 µM | Nav1.5 IC50 (nM) |
|---|---|---|---|---|---|---|---|---|---|---|---|---|
| 33 | 30000 | -19.4 | -0.18 | >10000 | >10000 | >10000 | >10000 | 7270 | >10000 | >10000 | 20 | >10000 |
| 34 | 30000 | -18.3 | -0.29 | >10000 | >10000 | 2350 | >10000 | 4100 | >10000 | 9160 | 0 | 3600 |
| 35 | 30000 | -10.3 | -0.16 | >10000 | >10000 | >10000 | >10000 | 4390 | >10000 | >10000 | 33 | 7500 |
| 36 | 30000 | -13.7 | -0.1 | >10000 | >10000 | >10000 | >10000 | >10000 | >10000 | >10000 | 28 | >10000 |
| 37 | 30000 | -5.4 | -0.03 | >10000 | >10000 | 6100 | >10000 | 5340 | >10000 | >10000 | | |
| 38 | 30000 | -16.9 | -0.15 | >10000 | >10000 | >10000 | >10000 | 3800 | >10000 | >10000 | | |
| 40 | 30000 | -8.8 | -0.05 | 10000 | 4050 | >10000 | >10000 | 680 | >10000 | 8300 | | |
| 41 | 30000 | -20.4 | -0.15 | >10000 | >10000 | >10000 | >10000 | >10000 | >10000 | >10000 | 45 | >10000 |
| 42 | 30000 | -7.3 | -0.13 | >10000 | >10000 | >10000 | >10000 | 3430 | >10000 | >10000 | | |
| 43 | 30000 | -6.2 | -0.06 | >10000 | >10000 | >10000 | >10000 | 4710 | >10000 | >10000 | | |
| 48 | 10000 | -9.7 | -0.08 | >10000 | 4000 | 8600 | >10000 | 3800 | >10000 | 9900 | 25 | |
| 49 | 10000 | -2.4 | 0 | >10000 | >10000 | >10000 | >10000 | >10000 | >10000 | >10000 | 26 | |
| 50 | 10000 | -3.9 | -0.03 | >10000 | >10000 | >10000 | >10000 | 4800 | >10000 | >10000 | 14 | |
| 51 | 10000 | -22.4 | -0.15 | >10000 | >10000 | >10000 | >10000 | >10000 | >10000 | >10000 | 32 | |
| 52 | 10000 | -20.1 | -0.12 | >10000 | >10000 | >10000 | >10000 | v | >10000 | >10000 | 44 | |
| 56 | 10000 | -10 | -0.07 | >10000 | >10000 | >10000 | >10000 | 7900 | >10000 | >10000 | 14 | |
| 57 | 10000 | -9 | -0.09 | >10000 | >10000 | >10000 | >10000 | >10000 | >10000 | >10000 | 24 | |
| 58 | 10000 | -5 | -0.06 | >10000 | >10000 | >10000 | >10000 | 9800 | >10000 | >10000 | | |
| 59 | 10000 | -8.2 | -0.1 | >10000 | >10000 | >10000 | >10000 | >10000 | >10000 | >10000 | 30 | |
| 60 | 10000 | -7.2 | -0.07 | 5500 | 6100 | >10000 | >10000 | 6100 | 6000 | 6500 | 15 | |
| 61 | 10000 | -8.4 | -0.1 | 8200 | 3900 | >10000 | >10000 | >10000 | >10000 | 8100 | 21 | |
| 62 | 10000 | -7.8 | -0.06 | >10000 | 5700 | >10000 | >10000 | 6100 | >10000 | >10000 | 15 | |
| 63 | 10000 | -5.8 | -0.038 | >10000 | >10000 | >10000 | >10000 | 2200 | >10000 | >10000 | 10 | |
| 64 | 10000 | -4.55 | -0.044 | >10000 | >10000 | >10000 | >10000 | 5300 | >10000 | >10000 | 19 | |

FIG. 1A (continued)

Modulation of ion channels by compounds of the invention

| No. | Conc. (nM) | Shift in $V_{1/2}$ (mV) | Change in P2/P1 at 20 mV | Cav2.2 IC50 closed-state (nM) | Cav2.2 IC50 inactivated-state (nM) | Cav3.1 IC50 (nM) | Cav3.2 IC50 closed-state (nM) | Cav3.2 IC50 inactivated-state (nM) | Cav1.2 IC50 closed-state (nM) | Cav1.2 IC50 inactivated-state (nM) | hERG, % inh. @ 3 μM | Nav1.5 IC50 (nM) |
|---|---|---|---|---|---|---|---|---|---|---|---|---|
| 65 | 10000 | -7.21 | -0.091 | 6200 | 6300 | >10000 | >10000 | 6400 | 7500 | 5300 | | |
| 66 | 10000 | -4.3 | -0.12 | >10000 | >10000 | >10000 | >10000 | >10000 | >10000 | >10000 | 18 | |
| 71 | 10000 | -8.5 | -0.07 | >10000 | >10000 | >10000 | >10000 | 5400 | >10000 | >10000 | 32 | |
| 72 | 10000 | -9.6 | -0.15 | >10000 | >10000 | 5800 | >10000 | 2400 | >10000 | >10000 | 31 | |
| 73 | 10000 | -5.7 | -0.1 | 9000 | 5300 | 890 | 1200 | 1200 | 8400 | 6400 | 24 | |
| 108 | 30000 | -5 | -0.04 | >10000 | >10000 | >10000 | >10000 | >10000 | >10000 | >10000 | | |
| 109 | 30000 | 0 | -0.02 | >10000 | >10000 | >10000 | >10000 | >10000 | >10000 | >10000 | | |
| 110 | 30000 | -14.2 | -0.08 | >10000 | >10000 | >10000 | >10000 | >10000 | >10000 | >10000 | 9 | >10000 |
| 111 | 30000 | -14.4 | -0.14 | >10000 | >10000 | >10000 | >10000 | >10000 | >10000 | >10000 | | |
| 112 | 30000 | -6.6 | -0.08 | >10000 | >10000 | >10000 | >10000 | >10000 | >10000 | >10000 | | |
| 113 | 30000 | -2.5 | -0.02 | >10000 | >10000 | >10000 | >10000 | >10000 | >10000 | >10000 | | |
| 114 | 30000 | -0.4 | 0.01 | >10000 | >10000 | >10000 | >10000 | >10000 | >10000 | >10000 | | |
| 115 | 30000 | 0.1 | -0.01 | >10000 | >10000 | >10000 | >10000 | >10000 | >10000 | >10000 | | |
| 117 | 30000 | -1.8 | -0.06 | >10000 | >10000 | >10000 | >10000 | >10000 | >10000 | >10000 | | |
| 118 | 30000 | -2.7 | -0.08 | >10000 | >10000 | >10000 | >10000 | >10000 | >10000 | >10000 | | |
| 121 | 30000 | -5.2 | -0.05 | >10000 | >10000 | >10000 | >10000 | >10000 | >10000 | >10000 | | |
| 122 | 30000 | 2.3 | -0.05 | >10000 | >10000 | >10000 | >10000 | >10000 | >10000 | >10000 | | |
| 123 | 30000 | -2.3 | -0.04 | >10000 | >10000 | >10000 | >10000 | >10000 | >10000 | >10000 | | |
| 124 | 30000 | -2.8 | -0.03 | >10000 | >10000 | >10000 | >10000 | >10000 | >10000 | >10000 | | |
| 125 | 30000 | -2.7 | -0.06 | >10000 | >10000 | >10000 | >10000 | >10000 | >10000 | >10000 | | |
| 126 | 30000 | -7.2 | -0.06 | >10000 | >10000 | >10000 | >10000 | >10000 | >10000 | >10000 | | |
| 129 | 30000 | -5.1 | -0.04 | >10000 | >10000 | >10000 | >10000 | >10000 | >10000 | >10000 | | |
| 130 | 30000 | -0.2 | -0.07 | >10000 | >10000 | >10000 | >10000 | >10000 | >10000 | >10000 | | |
| 131 | 30000 | -0.6 | -0.04 | >10000 | >10000 | >10000 | >10000 | >10000 | >10000 | >10000 | | |

FIG. 1A (continued)

| No. | Conc. (nM) | Shift in V₁/₂ (mV) | Change in P2/P1 at 20 mV | Modulation of ion channels by compounds of the invention |  |  |  |  |  |  |  | hERG, % inh. @ 3 µM | Nav1.5 IC50 (nM) |
|---|---|---|---|---|---|---|---|---|---|---|---|---|---|
| | | | | Cav2.2 IC50 closed-state (nM) | Cav2.2 IC50 inactivated-state (nM) | Cav3.1 IC50 (nM) | Cav3.2 IC50 closed-state (nM) | Cav3.2 IC50 inactivated-state (nM) | Cav1.2 IC50 closed-state (nM) | Cav1.2 IC50 inactivated-state (nM) | | | |
| 132 | 30000 | 1.3 | -0.01 | >10000 | >10000 | >10000 | >10000 | >10000 | >10000 | >10000 | | |
| 133 | 30000 | -5.1 | -0.06 | >10000 | >10000 | >10000 | >10000 | >10000 | >10000 | >10000 | | |
| 134 | 30000 | -4.9 | -0.06 | >10000 | >10000 | >10000 | >10000 | >10000 | >10000 | >10000 | | |
| 135 | 30000 | -1.9 | -0.02 | >10000 | >10000 | 4490 | 6120 | 640 | >10000 | >10000 | 18 | |
| 137 | 30000 | -3 | -0.11 | >10000 | >10000 | >10000 | >10000 | >10000 | >10000 | >10000 | | |
| 138 | 30000 | -4.3 | -0.07 | >10000 | 8820 | >10000 | >10000 | >10000 | >10000 | >10000 | | |
| 141 | 30000 | 0 | -0.02 | >10000 | >10000 | >10000 | >10000 | >10000 | >10000 | >10000 | | |
| 142 | 30000 | 1 | 0 | >10000 | >10000 | >10000 | 8450 | 2250 | >10000 | >10000 | | |
| 143 | 30000 | -7.2 | -0.11 | >10000 | >10000 | >10000 | >10000 | >10000 | >10000 | >10000 | | |
| 144 | 30000 | -1.1 | -0.03 | >10000 | >10000 | >10000 | >10000 | >10000 | >10000 | >10000 | | |
| 145 | 30000 | -3.4 | -0.04 | >10000 | >10000 | >10000 | >10000 | >10000 | >10000 | >10000 | | |
| 146 | 30000 | -5.2 | -0.11 | >10000 | >10000 | >10000 | >10000 | >10000 | >10000 | >10000 | | |
| 147 | 30000 | -3.2 | -0.09 | >10000 | >10000 | >10000 | >10000 | >10000 | >10000 | >10000 | | |
| 149 | 30000 | -10.5 | -0.16 | >10000 | >10000 | >10000 | >10000 | >10000 | >10000 | >10000 | 55 | >10000 |
| 150 | 30000 | -10.5 | -0.14 | >10000 | >10000 | >10000 | >10000 | 8090 | >10000 | >10000 | | |
| 151 | 30000 | -3.2 | -0.07 | >10000 | >10000 | >10000 | >10000 | >10000 | >10000 | >10000 | | |
| 152 | 30000 | -7.3 | -0.1 | >10000 | >10000 | >10000 | >10000 | >10000 | >10000 | >10000 | | |
| 153 | 30000 | -7 | -0.07 | >10000 | >10000 | >10000 | >10000 | >10000 | >10000 | >10000 | | |
| 154 | 30000 | -10.7 | -0.15 | >10000 | >10000 | >10000 | >10000 | >10000 | >10000 | >10000 | | |
| 155 | 10000 | -5 | -0.04 | >10000 | >10000 | >10000 | >10000 | 6800 | >10000 | >10000 | 26 | |
| 160 | 10000 | -1.6 | 0.01 | >10000 | >10000 | >10000 | >10000 | >10000 | >10000 | >10000 | | |
| 163 | 10000 | -6.16 | -0.041 | >10000 | >10000 | >10000 | >10000 | >10000 | >10000 | >10000 | | |
| 171 | 30000 | -26.3 | -0.3 | >10000 | 5260 | 3080 | >10000 | 1310 | >10000 | 4650 | 59 | |
| 172 | 10000 | -7.1 | -0.14 | >10000 | 6200 | 4500 | 4300 | 1000 | >10000 | >10000 | | |

FIG. 1A (continued)

| No. | Conc. (nM) | Shift in $V_{1/2}$ (mV) | Change in P2/P1 at 20 mV | Modulation of ion channels by compounds of the invention ||||||||
|---|---|---|---|---|---|---|---|---|---|---|
| | | | | Cav2.2 IC50 closed-state (nM) | Cav2.2 IC50 inactivated-state (nM) | Cav3.1 IC50 (nM) | Cav3.2 IC50 closed-state (nM) | Cav3.2 IC50 inactivated-state (nM) | Cav1.2 IC50 closed-state (nM) | Cav1.2 IC50 inactivated-state (nM) | hERG, % inh. @ 3 µM | Nav1.5 IC50 (nM) |
| 173 | 10000 | -9.1 | -0.17 | >10000 | 6000 | 5100 | 7200 | 2100 | >10000 | >10000 | 30 | |
| 174 | 10000 | -7 | -0.15 | >10000 | 5400 | 3400 | 6800 | 1500 | >10000 | >10000 | | |
| 175 | 10000 | -4.24 | -0.051 | >10000 | 5000 | 4400 | 5200 | 1900 | >10000 | >10000 | 29 | |

FIG. 1B

Modulation of ion channels by compounds of the invention

| No. | HNAV1.7 BIOPHYSICS PX SLOW INACT VDEP Delta Vhalf | HNAV1.7 BIOPHYSICS PX SLOW INACT VDEP Significant | HNAV1.7 BIOPHYSICS PX SLOW INACT VDEP Concentration | HNAV1.7 BIOPHYSICS PX SLOW INACT RATIO20MV Delta Ratio | HNAV1.7 BIOPHYSICS PX SLOW INACT RATIO20MV Significant |
|---|---|---|---|---|---|
| 189 | -16.6 | Y | 10000 | -0.07 | N |
| 190 | -31.7 | Y | 10000 | -0.12 | Y |
| 191 | -3.8 | N | 10000 | -0.01 | N |
| 192 | -2.4 | N | 10000 | -0.04 | N |
| 193 | -2.9 | N | 10000 | -0.1 | N |
| 194 | -5.6 | Y | 10000 | 0 | N |
| 195 | -8.5 | Y | 10000 | -0.04 | N |
| 196 | -21.9 | Y | 10000 | -0.17 | Y |
| 197 | -32.7 | Y | 10000 | -0.15 | Y |
|  | -14 | Y | 1000 | -0.06 | N |
| 198 | -5.3 | Y | 10000 | -0.03 | N |
| 199 | -17.5 | N | 10000 | -0.32 | N |
| 200 | -16.8 | Y | 10000 | -0.24 | Y |
| 201 | -8 | N | 10000 | -0.12 | Y |
| 202 | -10 | Y | 10000 | -0.08 |  |
| 203 | -17.8 | Y | 10000 | -0.21 | N |
| 204 | -22.7 | Y | 10000 | -0.21 | N |
|  | -10.8 | N | 1000 | -0.07 | N |
| 205 | -29.5 | Y | 10000 | -0.04 | N |
| 206 | -1.3 | N | 10000 | -0.08 | N |
| 207 | -14.7 | N | 10000 | -0.06 | N |
| 208 | -22.7 | N | 10000 | -0.12 | N |
|  | -8.1 | N | 1000 | -0.08 | N |
| 209 | -0.1 | N | 10000 | 0 | N |
| 210 | -21.9 | Y | 10000 | -0.03 | N |
| 211 | -14.7 | Y | 10000 | -0.09 | N |
| 236 | -14.7 | Y | 10000 | -0.07 | N |
| 216 | -8.4 | N | 10000 | -0.21 | Y |
| 212 | -15.6 | Y | 10000 | -0.11 | Y |
| 213 | -6.5 | N | 10000 | -0.06 | N |
| 214 | -9.4 | N | 10000 | -0.1 | N |
| 219 | -32.1 | Y | 10000 | -0.17 | N |
| 220 | -27.4 | Y | 10000 | -0.1 | N |
| 224 | -0.4 | N | 10000 | 0.01 | N |

FIG. 1B (continued)

| No. | HNAV1.7 BIOPHYSICS PX SLOW INACT VDEP | HNAV1.7 BIOPHYSICS PX SLOW INACT VDEP | HNAV1.7 BIOPHYSICS PX SLOW INACT VDEP | HNAV1.7 BIOPHYSICS PX SLOW INACT RATIO20MV | HNAV1.7 BIOPHYSICS PX SLOW INACT RATIO20MV |
|---|---|---|---|---|---|
| | *Delta Vhalf* | *Significant* | *Concentration* | *Delta Ratio* | *Significant* |
| 222 | -3.7 | N | 10000 | -0.03 | N |
| 223 | -30.2 | N | 10000 | -0.08 | N |
| 226 | -19.2 | N | 10000 | -0.1 | N |
| 228 | -13.3 | N | 10000 | -0.1 | N |
| 215 | -5 | N | 10000 | -0.02 | N |
| 225 | -5.8 | Y | 10000 | -0.06 | N |
| 217 | -13 | Y | 10000 | -0.17 | Y |
| 218 | -11.5 | Y | 10000 | -0.19 | N |
| 227 | -10.8 | Y | 10000 | -0.19 | N |
| 230 | -15.9 | Y | 10000 | -0.08 | N |
| 231 | -6.5 | N | 10000 | -0.07 | N |
| 232 | -7.3 | Y | 10000 | -0.07 | N |
| 235 | -16.9 | Y | 10000 | -0.1 | N |
| 233 | -15.2 | Y | 10000 | -0.19 | Y |
| 229 | -16.3 | Y | 10000 | -0.28 | Y |
| 234 | -21.4 | Y | 10000 | -0.33 | Y |
| 221 | -28.2 | Y | 10000 | -0.13 | Y |

Effect of compounds on SNL-induced mechanical hyperalgesia in the rat

□ Vehicle (DMA:PS80:PEG400.p.o)
▨ 1 (30mg/kg, p.o)
▨ 24 (30 mg/kg, p.o)
■ 41 (30 mg/kg, p.o)

Effect of compounds on SNL-induced mechanical hyperalgesia in the rat

□ Vehicle (DMA:PS80:PEG400, p.o)
▨ 56 (30mg/kg, p.o)         ▨ 33 (30 mg/kg, p.o)
▨ 36 (30 mg/kg, p.o)        ■ 34 (30 mg/kg, p.o)
▭ 31 (30mg/kg, p.o)

Effect of compound (110) on SNL-induced mechanical hyperalgesia in the rat

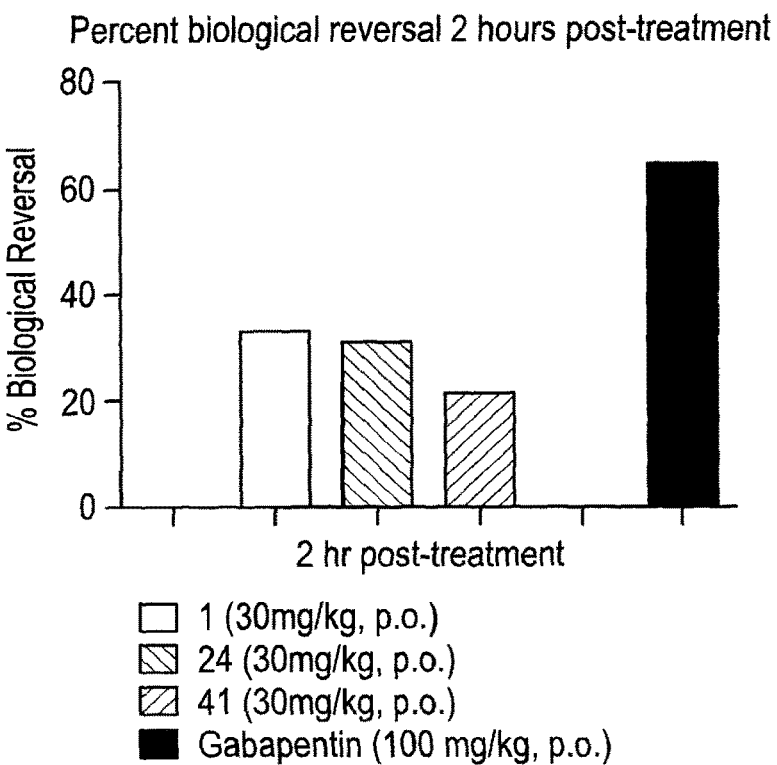
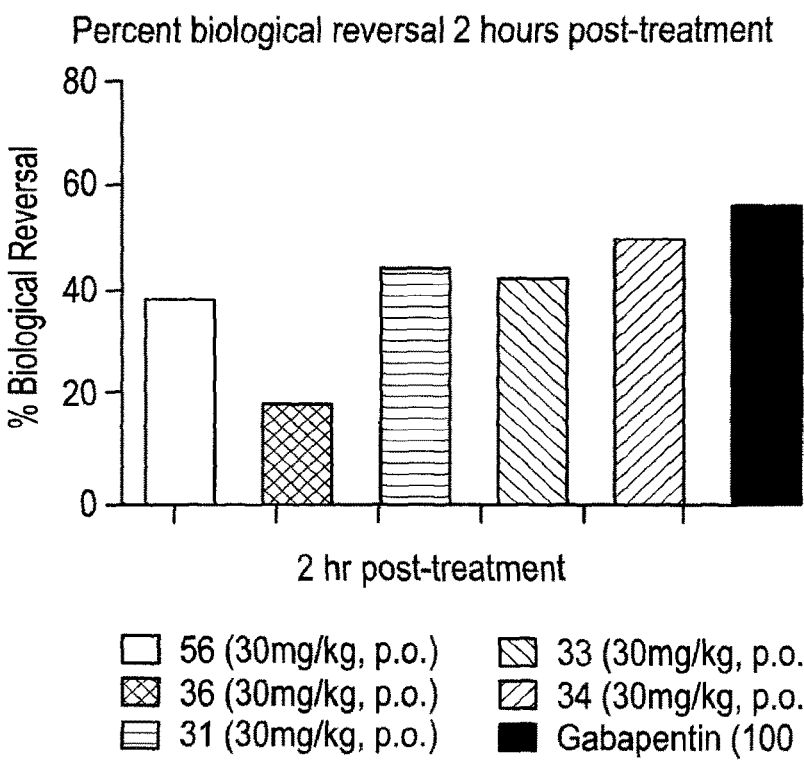

BENZIMIDAZOLE INHIBITORS OF THE SODIUM CHANNEL

CROSS REFERENCE TO RELATED APPLICATIONS

This application claims benefit of U.S. Provisional Application Nos. 61/448,923 and 61/448,910, each of which was filed on Mar. 3, 2011, and each of which is hereby incorporated by reference in its entirety.

FIELD OF THE INVENTION

The invention relates to compounds useful in treating conditions associated with voltage-gated ion channel function, particularly conditions associated with sodium channel activity. More specifically, the invention concerns benzimidazole compounds that are useful in treatment numerous diseases and conditions.

BACKGROUND OF THE INVENTION

Voltage-gated sodium ($Na_v$) channels are present in neurons and excitable tissues where they contribute to processes such as membrane excitability and muscle contraction (Ogata et al., *Jpn. J. Pharmacol.* (2002) 88(4) 365-77). Nine different transmembrane α-subunits ($Na_v1.1$-1.9) from a single $Na_v1$ family combine with auxiliary β-subunits that modify channel function to form functional $Na_v$ channels. Of the nine $Na_v1$ α-subunit isoforms, five are expressed in the dorsal root ganglion where they are involved in setting the resting membrane potential and the threshold for generating action potentials, and also contribute to the upstroke as well as firing of action potentials during sustained depolarization. In particular, the tetrodotoxin (TTX) sensitive $Na_v1.7$ and TTX-insensitive $Na_v1.8$ channel subtypes act as major contributors to both inflammatory and neuropathic pain (Momin et al., *Curr Opin Neurobiol.* 18(4):383-8, 2008; Rush et al., *J Physiol.* 579(Pt 1):1-14, 2007).

Novel allosteric modulators of voltage-gated ion channels (e.g., sodium channels) are thus desired. Modulators may affect the kinetics and/or the voltage potentials of, e.g., $Na_v1.7$ and/or $Na_v1.8$ channels.

SUMMARY OF THE INVENTION

The invention relates to compounds useful in conditions modulated by voltage-gated ion channels (e.g., voltage gated sodium channels).

In a first aspect, the invention features a compound having a structure according to the following formula,

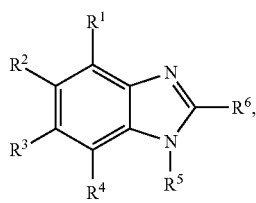

(I)

or a pharmaceutically acceptable salt or solvate thereof, where each of $R^1$, $R^2$, $R^3$, and $R^4$ is selected, independently, from H, optionally substituted C1-C6 alkyl, optionally substituted C1-C6 haloalkyl, optionally substituted C6-C10 aryl, or optionally substituted 5 to 6-membered heteroaryl, where at least one of $R^1$, $R^2$, $R^3$, and $R^4$ is halogen or optionally substituted C1-C6 haloalkyl;

$R^5$ is H, optionally substituted C1-C6 alkyl, or optionally substituted C1-C10 heteroalkyl;

$R^6$ is —$R^{6A}$ or —$CH_2R^{6B}$;

$R^{6A}$ is $NH_2$, optionally substituted cyclopropyl, optionally substituted azetidine, optionally substituted cyclopentyl, optionally substituted pyrazole, optionally substituted pyrrole, optionally substituted pyrrolidine, optionally substituted thiazolidine, optionally substituted thiazolidine-1,1-dioxide, optionally substituted pyrimidine, optionally substituted C1-C10 aminoalkyl, optionally substituted C1-C10 hydroxyalkyl, optionally substituted C1-C10 alkoxyalkyl, optionally substituted C1-C10 haloalkyl, or optionally substituted C1-C10 alkylsulfonyl; or $R^{6A}$ has a structure according to

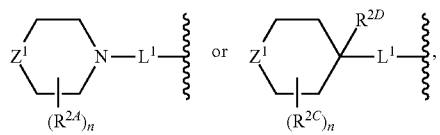

where n is an integer between 0-4;

$Z^1$ is $CH_2$, NH, $NCH_3$, or O;

$L^1$ is —$CH_2$—, —$CHR^{4A}$—, —$CH_2C(=O)$—, —$C(=O)CH_2$—, —$CH_2C(=O)NH$—, —$CH_2C(=O)NHCH_2$—, or —$CH_2NHC(=O)CH_2$—;

each $R^{2A}$ and $R^{2C}$, when present, is selected from OH, $N(R^{2B})_2$, halogen, and unsubstituted C1-C3 alkyl, or two $R^{2A}$ combine to form an oxo (=O) group, and wherein no more than two $R^{2A}$ combine to form an oxo group; and each $R^{2B}$ is, independently, H or unsubstituted C1-C6 alkyl;

$R^{2D}$ is H, OH, or $NH_2$;

and $R^{6B}$ is optionally substituted cyclopropyl, optionally substituted azetidine, optionally substituted cyclopentyl, optionally substituted pyrazole, optionally substituted pyrrole, optionally substituted pyrrolidine, optionally substituted thiazolidine, optionally substituted thiazolidine-1,1-dioxide, or optionally substituted pyrimidine.

In some embodiments, $R^{6A}$ is $NH_2$, optionally substituted cyclopropyl, optionally substituted azetidine, optionally substituted cyclopentyl, optionally substituted pyrazole, optionally substituted pyrrole, optionally substituted pyrrolidine, optionally substituted thiazolidine, optionally substituted thiazolidine-1,1-dioxide, optionally substituted pyrimidine, optionally substituted C1-C10 aminoalkyl, optionally substituted C1-C10 hydroxyalkyl, optionally substituted C1-C10 alkoxyalkyl, optionally substituted C1-C10 haloalkyl, or optionally substituted C1-C10 alkylsulfonyl.

In other embodiments, $R^6$ has a structure according to

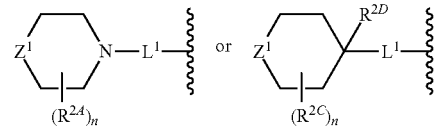

In some embodiments, $R^5$ is H.

In other embodiments, $R^5$ is optionally substituted C1-C10 heteroalkyl.

In certain embodiments, $R^2$ and $R^4$ are both $CF_3$, F, or Cl.

In still other embodiments, $R^2$ and $R^3$ are both $CF_3$, F, or Cl.

In some embodiments, $R^6$ is $-CH_2R^{6B}$, and $R^{6B}$ is optionally substituted azetidine.

In certain embodiments, $R^6$ is optionally substituted C1-C10 aminoalkyl.

In other embodiments, the C1-C10 aminoalkyl includes an oxo (=O) substituent, an alkoxy substituent, an N-sulfonyl group, or any combination thereof.

In some embodiments, the compound has a structure according to the following formula,

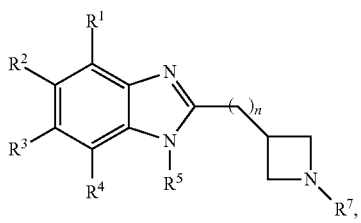

(II)

or a pharmaceutically acceptable salt or solvate thereof, where n is 0 or 1, and $R^7$ is H or $-C(=O)R^{7A}$, where $R^{7A}$ is unsubstituted C1-C6 alkyl or optionally substituted C1-C10 aminoalkyl.

In certain embodiments, n is 0.

In other embodiments, n is 1.

In some embodiments, $R^7$ is H or $C(=O)R^{7A}$, where $R^{7A}$ is unsubstituted C1-C3 alkyl or an optionally substituted C1-C10 aminoalkyl including a terminal $-NH_2$ group.

In further embodiments, $R^2$ and $R^4$ are both $CF_3$, F, or Cl.

In some embodiments, $R^2$ and $R^3$ are both $CF_3$, F, or Cl.

In other embodiments, $R^6$ is optionally substituted cyclopropyl, optionally substituted azetidine, optionally substituted cyclopentyl, optionally substituted pyrazole, optionally substituted pyrrole, optionally substituted pyrrolidine, optionally substituted thiazolidine, optionally substituted thiazolidine-1,1-dioxide, optionally substituted pyrimidine.

In still other embodiments, $R^6$ includes a $-NH_2$ substituent.

In some embodiments, the compound has a structure according to the following formula,

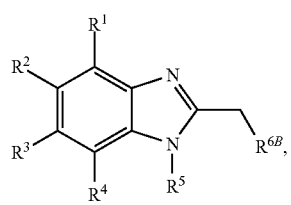

(III)

where $R^{6B}$ is optionally substituted azetidine, optionally substituted cyclopentyl, optionally substituted pyrrolidine, optionally substituted thiazolidine, optionally substituted thiazolidine-1,1-dioxide, or optionally substituted pyrimidine.

In certain embodiments, $R^2$ and $R^4$ are both $CF_3$, F, or Cl.

In other embodiments, $R^2$ and $R^3$ are both $CF_3$, F, or Cl.

In further embodiments, $R^5$ is H.

In still other embodiments, $R^6$ is an optionally substituted C1-C10 aminoalkyl group.

In some embodiments, the C1-C10 aminoalkyl includes a terminal $-NH_2$ group.

In other embodiments, the C1-C10 aminoalkyl includes an oxo (=O) substituent.

In certain embodiments, $R^6$ is $-(CH_2)_{m1}(NR^{6C})_{m2}(C=O)_{m3}(CH_2)_{m4}NR^{6D}R^{6E}$ or $-(CH_2)_{m1}(C(CH_3)_2)_{m2}(CH_2)_{m4}NR^{6C}R^{6D}$ where each of m1 and m4 is, independently, an integer between 1-6; each of m2 and m3 is, independently, 0 or 1; each of $R^{6C}$ and $R^{6E}$ is, independently, H or unsubstituted C1-C6 alkyl; and $R^{6D}$ is H, unsubstituted C1-C6 alkyl, or an N-protecting group.

In some embodiments, $R^6$ is $-(CH_2)_{m1}NH_2$, $-CH_2NHC(=O)CH_2NH_2$, $-C(CH_3)_2CH_2NH_2$, $-C(CH_3)_2NH_2$, and where m1 is 1, 2, or 3.

In other embodiments, $R^2$ and $R^4$ are both $CF_3$, F, or Cl.

In still other embodiments, $R^2$ and $R^3$ are both $CF_3$, F, or Cl.

In particular embodiments, one and only one of $R^2$ or $R^3$ is optionally substituted phenyl.

In certain embodiments, $R^5$ is H.

In some embodiments, $R^6$ is optionally substituted C1-C3 haloalkyl, optionally substituted C1-C10 alkoxyalkyl, optionally substituted C1-C10 hydroxyalkyl, or optionally substituted C1-C10 alkylsulfonyl.

In other embodiments, $R^6$ is $-(CH_2)_{m1}CF_3$, $-(CH_2)_{m1}OR^{6F}$, $-(CH_2)_{m1}SO_2R^{6G}$, where m1 is an integer between 1-6, $R^{6F}$ is H or $CH_3$, and $R^{6G}$ is unsubstituted C1-C3 alkyl.

In further embodiments, $R^2$ and $R^4$ are both $CF_3$, F, or Cl.

In certain embodiments, $R^2$ and $R^3$ are both $CF_3$, F, or Cl.

In some embodiments, $R^5$ is H.

In a second aspect, the invention features a compound having a structure according to the following formula,

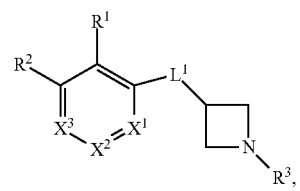

(IV)

or a pharmaceutically acceptable salt or solvate thereof, where each of $X^1$, $X^2$, and $X^3$ is N or $CR^4$, and where one and only one of $X^1$, $X^2$, and $X^3$ is N;

$L^1$ is a covalent bond, $-CH_2$, $-CHR^{5A}$, $-CH_2C(=O)$, $-C(=O)CH_2$, $-CH_2C(=O)NH$, $-CH_2C(=O)NHCH_2$, $-CH_2NHC(=O)CH_2$, or $-CH_2CH_2$;

each of $R^1$, $R^2$, and $R^4$ is, independently, H, unsubstituted C1-C3 alkyl, optionally substituted C1-C3 haloalkyl, or halogen;

$R^3$ is H, optionally substituted C1-C6 alkyl, or optionally substituted C1-C10 heteroalkyl;

$R^{5A}$ is selected from optionally substituted C1-C3 alkyl; and where at least one of $R^1$, $R^2$, $R^3$, and $R^5$ is halogen or optionally substituted C1-C3 haloalkyl.

In some embodiments, $L^1$ is $CH_2$ or $CHCF_3$.

In other embodiments, $R^3$ is H.

In another aspect, the invention features a compound having a structure according to the following formula,

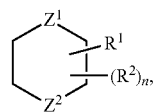
(V)

or a pharmaceutically acceptable salt or solvate thereof, where n is an integer between 0-4;

$R^1$ is selected from —$CH_2R^{3A}$, —$CHR^{4A}R^{3A}$, —$CH_2C(=O)R^{3A}$, —$C(=O)CH_2R^{3A}$, —$CH_2C(=O)NR^{4B}R^{3A}$, $CH_2C(=O)NR^{4B}CH_2R^{3A}$, —$CH_2NR^{4B}C(=O)CH_2R^{3A}$, —$R^{3B}$, —$CH_2CH_2R^{3B}$, and —$CH_2C(=O)NR^{4B}CHR^{4C}R^{3C}$;

each $R^2$, when present, is selected from OH, $N(R^{2A})_2$, halogen, and unsubstituted C1-C3 alkyl, or two $R^2$ combine to form an oxo (=O) group, and where no more than two $R^2$ combine to form an oxo group;

each $R^{2A}$ is, independently, H or unsubstituted C1-C6 alkyl;

$R^{3A}$ is selected from a benzimidazole including at least one C-substituent selected from halogen or C1-C6 haloalkyl or an N-substituent that is C1-C12 heteroalkyl;

a pyridine including at least one substituent selected from halogen or C1-C6 haloalkyl; and a pyrazole including at least one substituent selected from halogen, unsubstituted C1-C3 alkyl, and C1-C6 haloalkyl;

$R^{3B}$ is selected from a benzimidazole including at least one C-substituent selected from Cl, Br, I, or C1-C6 haloalkyl or an N-substituent that is a C1-C10 heteroalkyl;

a pyridine including at least one substituent selected from halogen or C1-C6 haloalkyl; and a pyrazole including at least one substituent selected from halogen, unsubstituted C1-C3 alkyl, and C1-C6 haloalkyl;

$R^{3C}$ is optionally substituted pyridine;

$R^{4A}$ is optionally substituted C1-C3 alkyl;

$R^{4B}$ is H or optionally substituted C1-C3 alkyl;

$R^{4C}$ is C1-C3 haloalkyl;

$Z^1$ is selected from $CH_2$, O, and $NR^5$, where $R^5$ is H or unsubstituted C1-C6 alkyl; and $Z^2$ is NH, $NR^6$, $CHR^2$, $CR^6R^2$, where $R^6$ is a covalent bond to $R^1$.

In some embodiments, n is 0.

In other embodiments, n is 2 or 4. In further embodiments, two $R^2$ combine to form an oxo group. In certain embodiments, $R^2$ is $CH_3$.

In some embodiments, $Z^1$ is O, NH, $CH_2$, or $NCH_3$.

In other embodiments, $Z^2$ is N, CH, or $CNH_2$.

The compounds described herein can have a structure according to the following formula,

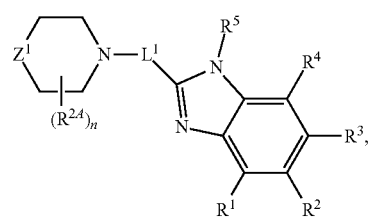
(VI)

or a pharmaceutically acceptable salt thereof, where $Z^1$ is $CH_2$, NH, $NCH_3$, or O;

$L^1$ is —$CH_2$, —$CHR^{4A}$, —$CH_2C(=O)$, —$C(=O)CH_2$, —$CH_2C(=O)NH$, —$CH_2C(=O)NHCH_2$, or —$CH_2NHC(=O)CH_2$;

$R^5$ is H or C1-C10 heteroalkyl;

each of $R^1$, $R^2$, $R^3$, and $R^4$ is, independently, H, unsubstituted C1-C3 alkyl, optionally substituted C1-C3 haloalkyl, or halogen, and where at least one of $R^1$, $R^2$, $R^3$, $R^4$, and $R^{R5}$ is not H.

In some embodiments, $Z^1$ is NH.

In other embodiments, n is 2 or 4.

In some embodiments, two $R^{2A}$ combine to form an oxo group.

In other embodiments, $R^{2A}$ is $CH_3$.

In still other embodiments, $R^1$ and $R^4$ are both H.

In certain embodiments, $R^1$ and $R^4$ are, independently, F, $CF_3$, or Cl.

In some embodiments, $R^3$ is F, Cl, or $CF_3$.

In other embodiments, $R^2$ is F, Cl, or $CF_3$.

In still other embodiments, $R^5$ is H.

In further embodiments, $R^5$ is optionally substituted C1-C10 hydroxyalkyl or C1-C10 aminoalkyl.

In other embodiments, $L^1$ is $CH_2$.

In other embodiments, the compound has a structure according to the following formula,

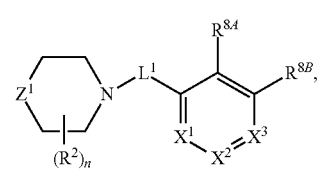
(VII)

or a pharmaceutically acceptable salt thereof, where $Z^1$ is $CH_2$, NH, $NCH_3$, or O;

each of $X^1$, $X^2$, and $X^3$ is N or $CR^{8C}$, and where one and only one of $X^1$, $X^2$, and $X^3$ is N;

$L^1$ is a covalent bond, —$CH_2$, —$CHR^{4A}$, —$CH_2C(=O)$, —$C(=O)CH_2$, —$CH_2C(=O)NH$, —$CH_2C(=O)NHCH_2$, —$CH_2NHC(=O)CH_2$, or —$CH_2CH_2$;

each of $R^{8A}$, $R^{8B}$, and $R^{8C}$ is, independently, H, unsubstituted C1-C3 alkyl, optionally substituted C1-C3 haloalkyl, or halogen, and where at least one of $R^7$, $R^{8A}$, $R^{8B}$, $R^{8C}$, and $R^{8D}$ is not H.

In some embodiments, $Z^1$ is NH.

In other embodiments, n is 2 or 4. In certain embodiments, two $R^2$ combine to form an oxo group.

In further embodiments, $R^2$ is $CH_3$.

In some embodiments, $X^2$ is N.

In still other embodiments, at least one of $R^{8A}$, $R^{8B}$, and $R^{8C}$ is F, Cl, or $CF_3$.

In some embodiments, $L^1$ is $-CH_2C(=O)NHCH_2$ or $-CH_2NHC(=O)CH_2$.

In other embodiments, the compound has a structure according to the following formula,

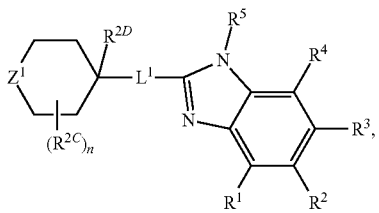

(VIII)

or a pharmaceutically acceptable salt or solvate thereof wherein
$Z^1$ is $CH_2$ or NH;
$L^1$ is a covalent bond, $-CH_2$, $-CHR^{4A}$, $-CH_2C(=O)$, $-C(=O)CH_2$, $-CH_2C(=O)NH$, $-CH_2C(=O)NHCH_2$, $-CH_2C(=O)NHCHCF_3-$, or $-CH_2NHC(=O)CH_2$;
n is an integer between 0-4;
each $R^{2C}$, when present, is independently, OH, $NH_2$, $NHCH_3$, $N(CH_3)_2$, or unsubstituted C1-C3 alkyl, or two $R^{2C}$ groups combine to form an oxo (=O) group, and wherein no more than one $R^{2B}$ or $R^{2C}$ group can be OH $NH_2$, $NHCH_3$, or $N(CH_3)_2$;
$R^{2D}$ is H, OH, or $NH_2$,
$R^5$ is H or C1-C10 heteroalkyl;
each of $R^1$, $R^2$, $R^3$, and $R^4$ is, independently, H, unsubstituted C1-C3 alkyl, optionally substituted C1-C3 haloalkyl, or halogen, and
wherein at least one of $R^1$, $R^2$, $R^3$, $R^4$, and $R^5$ is not H.

In certain embodiments, $Z^1$ is $CH_2$.
In other embodiments, n is 0 or 1.
In certain embodiments, one of $R^2$ and $R^3$ is $NH_2$, $NHCH_3$, or $N(CH_3)_2$.
In further embodiments, $R^1$ and $R^4$ are both H.
In other embodiments, $R^1$ and $R^4$ are, independently, F, $CF_3$, or Cl.
In still other embodiments, $R^3$ is F, Cl, or $CF_3$.
In certain embodiments, $R^2$ is F, Cl, or $CF_3$.
In some embodiments, $R^5$ is H.
In certain embodiments, the compound has a structure according to the following formula,

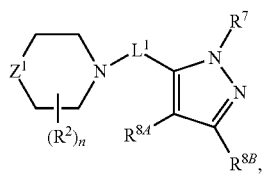

(IX)

or a pharmaceutically acceptable salt or solvate thereof, where
$Z^1$ is $CH_2$, NH, $NCH_3$, or O;
$L^1$ is a covalent bond, $-CH_2$, $-CHR^{4A}$, $-CH_2C(=O)$, $-C(=O)CH_2$, $-CH_2C(=O)NH$, $-CH_2C(=O)NHCH_2$, $-CH_2NHC(=O)CH_2$, or $-CH_2CH_2$;
$R^7$ is selected from H, optionally substituted C1-C6 alkyl, and optionally substituted C1-C10 heteroalkyl;

each of $R^{8A}$ and $R^{8B}$ is selected, independently, from H, halogen, unsubstituted C1-C3 alkyl, and C1-C3 haloalkyl, and
where at least one of $R^7$, $R^{8A}$, and $R^{8B}$ is not H.

In some embodiments, $Z^1$ is N.
In other embodiments, n is 2 or 4.
In still other embodiments, two $R^2$ combine to form an oxo group.
In certain embodiments, $R^2$ is $CH_3$.
In some embodiments, $R^7$ is unsubstituted C1-C3 alkyl.
In further embodiments, at least one of $R^{8A}$ and $R^{8B}$ is F, Cl, or $CF_3$.
In some embodiments, $L^1$ is $CH_2$.
In still another aspect, the invention features a compound having a structure according to the following formula,

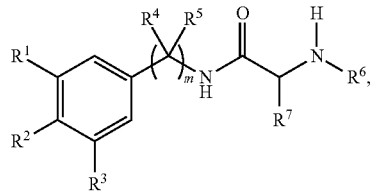

(X)

or a pharmaceutically acceptable salt or solvate thereof, where
each of $R^1$, $R^2$, and $R^3$ is, independently, H, unsubstituted C1-C6 alkyl, optionally substituted C1-C6 haloalkyl, or halogen;
m is 1 or 2;
each $R^4$ and $R^5$ is, independently, H, optionally substituted C1-C6 alkyl, or optionally substituted C1-C6 haloalkyl, or $R^4$ and $R^5$ combine to form an optionally substituted C3-C6 cycloalkyl, or $R^4$ and $R^5$ combine to form an oxo (C=O) group;
each of $R^6$ and $R^8$ is, independently, H or optionally substituted C1-C6 alkyl; or $R^6$ and $R^8$ combine to form an optionally substituted three-to-nine membered heterocyclyl, or $R^6$ and $R^{7A}$ combine to form an optionally substituted three-to-nine membered heterocyclyl;
n is 1 or 2;
each $R^{7A}$ and $R^{7B}$ is, independently H, optionally substituted C1-C6 alkyl, or optionally substituted C1-C6 haloalkyl; or $R^6$ combines with $R^{7A}$ to form an optionally substituted three-to-nine heterocyclyl; or an $R^{7A}$ and $R^{7B}$ group on the same carbon combine to form an optionally substituted C3-C6 cycloalkyl; or, when n is 2, both $R^{7A}$ groups combine to form an optionally substituted C3-C6 cycloalkyl.

In some embodiments, each of $R^1$, $R^2$, and $R^3$ is, independently, H, C1-C3 haloalkyl, or halogen.
In other embodiments, one of $R^1$, $R^2$, and $R^3$ is H.
In still other embodiments, two of $R^1$, $R^2$, and $R^3$ are, independently, $CF_3$, Cl, or F.
In certain embodiments, $R^4$ and $R^5$ are both H; or $R^4$ and $R^5$ are both $CH_3$; or $R^4$ and $R^5$ combine to form an optionally substituted C3-C6 cycloalkyl; or $R^4$ and $R^5$ combine to form an oxo (C=O) group.
In other embodiments, $R^6$ combines with $R^{7A}$ to form a three-to-six membered heterocyclyl ring, or wherein $R^6$ and $R^8$ combine to form an optionally substituted three-to-six membered heterocyclyl.

In still other embodiments, $R^6$ is H.

In some embodiments, $R^{7A}$ is H and $R^{7B}$ is optionally substituted C1-C6 alkyl.

In still other embodiments, the compound has a structure according to a formula that is

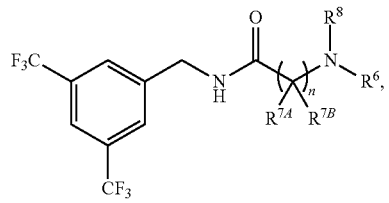
(XI)

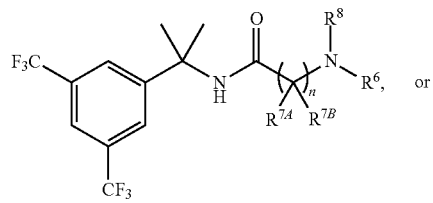
(XII)

or

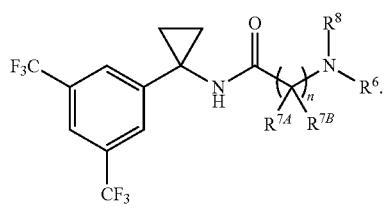
(XIII)

In further embodiments, n is 1, and $R^{7A}$ and $R^{7B}$ are both H, or $R^{7A}$ is H and $R^{7B}$ is optionally substituted C1-C6 alkyl. In still other embodiments, $R^6$ is H and $R^8$ is optionally substituted C1-C6 alkyl, or wherein $R^6$ and $R^8$ combine to form an optionally substituted five- to six-membered heterocyclyl (e.g., an unsubstituted five- to six-membered heterocyclyl or a five- to six-membered heterocyclyl that includes a phenyl substituent).

In another aspect, the invention features a compound having a structure selected from the group consisting of any of Compounds (1)-(236) of Table 1, or a pharmaceutically acceptable salt or solvate thereof. In some embodiments, the compound, or a pharmaceutically acceptable salt or solvate thereof, selected from the group consisting of

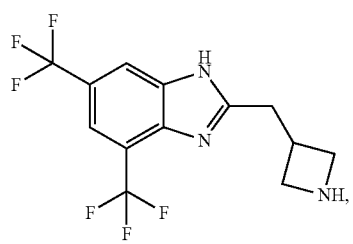
(1)

-continued

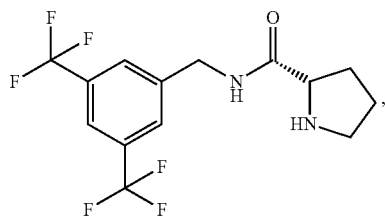
(17)

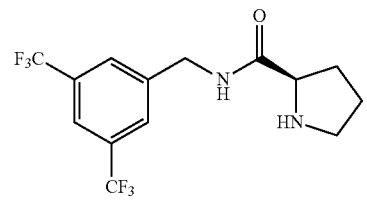
(18)

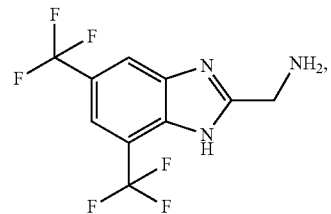
(23)

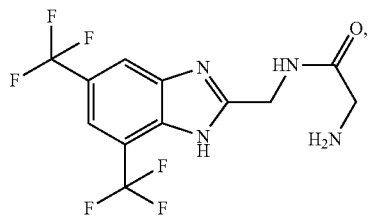
(24)

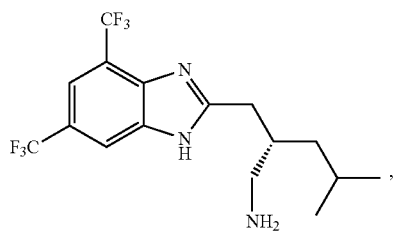
(31)

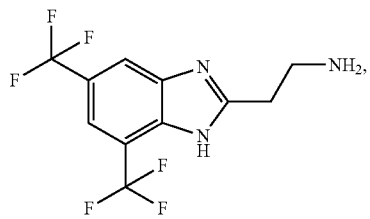
(33)

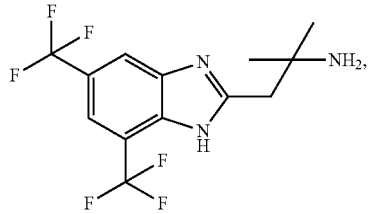
(34)

-continued
(36)
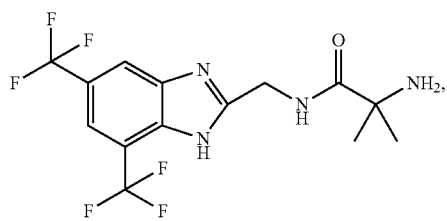
(38)
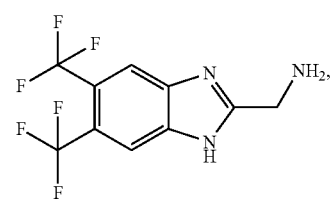
(41)
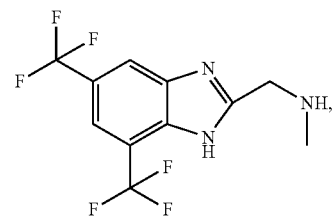
(75)
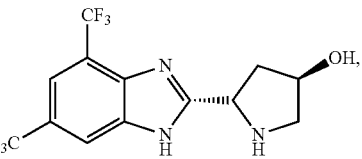
(76)
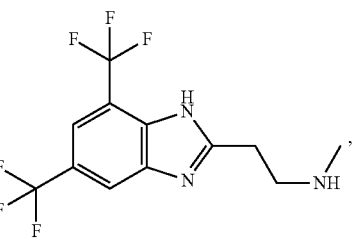
(106)
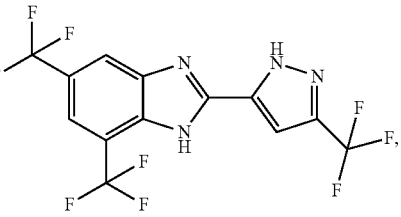
(110)
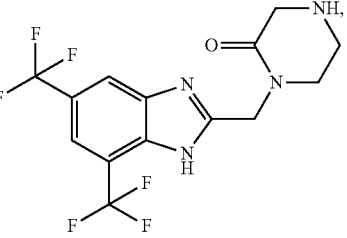
-continued
(183)
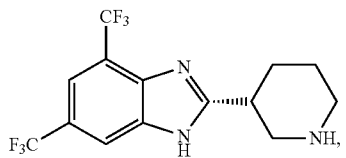
(185)
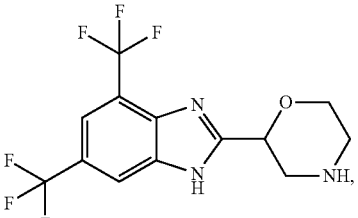
(197)
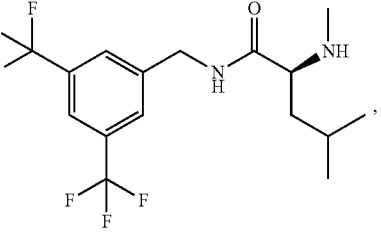
(204)
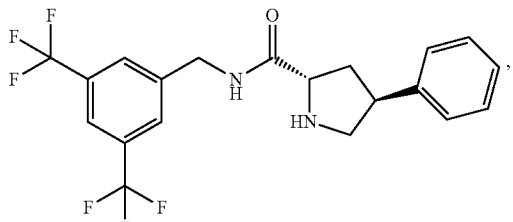
(208)
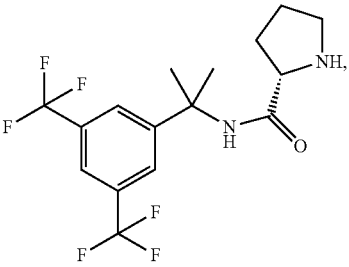
(218)
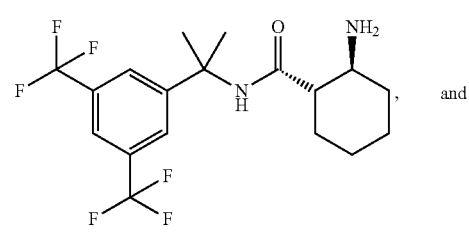
and
(236)
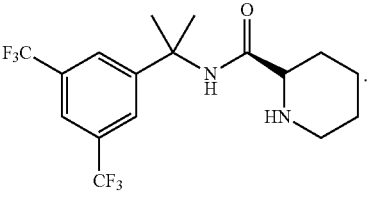

In another aspect, the invention features a pharmaceutical composition that includes any of the compounds described herein (e.g., a compound according to any of Formulas (I)-(XIII) or any of Compounds (1)-(236) of Table 1) and a pharmaceutically acceptable carrier or excipient.

In some embodiments, the pharmaceutical composition is formulated in unit dosage form (e.g., a tablet, caplet, capsule, lozenge, film, strip, gelcap, or syrup).

In still another aspect, the invention features method to treat a disease or condition by administering to a subject in need of such treatment an effective amount of any of the compounds described herein (e.g., a compound according to any of Formulas (I)-(XIII) or any of Compounds (1)-(236) of Table 1), or a pharmaceutical composition thereof.

In certain embodiments, the disease or condition is pain, epilepsy, Parkinson's disease, a mood disorder (e.g., a major depressive disorder (e.g., atypical depression, melancholic depression, psychotic major depression, catatonic depression, postpartum depression, seasonal affective disorder, dysthymia, and depressive disorder not otherwise specified (DD-NOS)), recurrent brief depression, minor depressive disorder, or a bipolar disorder), psychosis (e.g., schizophrenia), tinnitus, amyotropic lateral sclerosis, glaucoma, ischaemia, spasticity disorders, obsessive compulsive disorder, restless leg syndrome, and Tourette syndrome.

In some embodiments, the subject is a fasted subject.

In certain embodiments, the subject is a fed subject.

In other embodiments, the condition is pain or epilepsy.

In some embodiments, the pain is inflammatory pain (e.g., inflammatory pain caused by rheumatoid arthritis, juvenile idiopathic arthritis, ankylosing spondylitis, psoriatic arthritis, inflammatory bowel disease, primary dysmenorrhea, or endometriosis) or neuropathic pain.

In certain embodiments, the pain is chronic pain.

In further embodiments, the chronic pain is peripheral neuropathic pain; central neuropathic pain, musculoskeletal pain, headache, visceral pain, or mixed pain.

In some embodiments, the peripheral neuropathic pain is post-herpetic neuralgia, diabetic neuropathic pain, neuropathic cancer pain, HIV-associated neuropathy, erythromelalgia, failed back-surgery syndrome, trigeminal neuralgia, or phantom limb pain; said central neuropathic pain is multiple sclerosis related pain, Parkinson disease related pain, post-stroke pain, post-traumatic spinal cord injury pain, lumbosacral radiculopathy, cervical radiculopathy, brachial radiculopathy, or pain in dementia; the musculoskeletal pain is osteoarthritic pain and fibromyalgia syndrome; inflammatory pain such as rheumatoid arthritis, or endometriosis; the headache is migraine, cluster headache, tension headache syndrome, facial pain, or headache caused by other diseases; the visceral pain is interstitial cystitis, irritable bowel syndrome, or chronic pelvic pain syndrome; or the mixed pain is lower back pain, neck and shoulder pain, burning mouth syndrome, or complex regional pain syndrome.

In other embodiments, the headache is migraine.

In certain embodiments, the pain is acute pain.

In further embodiments, the acute pain is nociceptive pain or post-operative pain.

In another aspect, the invention features a method of modulating a voltage-gated sodium channel, the method including contacting a cell with any of the compounds described herein (e.g., a compound according to any of Formulas (I)-(XIII) or any of Compounds (1)-(236) of Table 1).

The term "alkoxy" represents a chemical substituent of formula —OR, where R is an optionally substituted C1-C6 alkyl group, unless otherwise specified. In some embodiments, the alkyl group can be substituted, e.g., the alkoxy group can have 1, 2, 3, 4, 5 or 6 substituent groups as defined herein.

The term "alkoxyalkyl" represents a heteroalkyl group, as defined herein, that is described as an alkyl group that is substituted with an alkoxy group. Exemplary unsubstituted alkoxyalkyl groups include between 2 to 12 carbons. In some embodiments, the alkyl and the alkoxy each can be further substituted with 1, 2, 3, or 4 substituent groups as defined herein for the respective group.

As used herein, the term "alkyl," "alkenyl" and "alkynyl" include straight-chain, branched-chain and cyclic monovalent substituents, as well as combinations of these, containing only C and H when unsubstituted. Examples include methyl, ethyl, isobutyl, cyclohexyl, cyclopentylethyl, 2-propenyl, 3-butynyl, and the like. The term "cycloalkyl," as used herein, represents a monovalent saturated or unsaturated non-aromatic cyclic alkyl group having between three to nine carbons (e.g., a C3-C9 cycloalkyl), unless otherwise specified, and is exemplified by cyclopropyl, cyclobutyl, cyclopentyl, cyclohexyl, cycloheptyl, bicyclo[2.2.1.]heptyl, and the like. When the cycloalkyl group includes one carbon-carbon double bond, the cycloalkyl group can be referred to as a "cycloalkenyl" group. Exemplary cycloalkenyl groups include cyclopentenyl, cyclohexenyl, and the like.

Typically, the alkyl, alkenyl and alkynyl groups contain 1-12 carbons (e.g., C1-C12 alkyl) or 2-12 carbons (e.g., C2-C12 alkenyl or C2-C12 alkynyl). In some embodiments, the alkyl groups are C1-C8, C1-C6, C1-C4, C1-C3, or C1-C2 alkyl groups; or C2-C8, C2-C6, C2-C4, or C2-C3 alkenyl or alkynyl groups. Further, any hydrogen atom on one of these groups can be replaced with a substituent as described herein.

Heteroalkyl, heteroalkenyl and heteroalkynyl are similarly defined and contain at least one carbon atom but also contain one or more O, S or N heteroatoms or combinations thereof within the backbone residue whereby each heteroatom in the heteroalkyl, heteroalkenyl or heteroalkynyl group replaces one carbon atom of the alkyl, alkenyl or alkynyl group to which the heteroform corresponds. In some embodiments, the heteroalkyl, heteroalkenyl and heteroalkynyl groups have C at each terminus to which the group is attached to other groups, and the heteroatom(s) present are not located at a terminal position. As is understood in the art, these heteroforms do not contain more than three contiguous heteroatoms. In some embodiments, the heteroatom is O or N. The term "heterocyclyl," as used herein represents cyclic heteroalkyl or heteroalkenyl that is, e.g., a 3-, 4-, 5-, 6- or 7-membered ring, unless otherwise specified, containing one, two, three, or four heteroatoms independently selected from the group consisting of nitrogen, oxygen, and sulfur. The 5-membered ring has zero to two double bonds, and the 6- and 7-membered rings have zero to three double bonds. The term "heterocyclyl" also represents a heterocyclic compound having a bridged multicyclic structure in which one or more carbons and/or heteroatoms bridges two non-adjacent members of a monocyclic ring, e.g., a quinuclidinyl group. The term "heterocyclyl" includes bicyclic, tricyclic, and tetracyclic groups in which any of the above heterocyclic rings is fused to one, two, or three carbocyclic rings, e.g., an aryl ring, a cyclohexane ring, a cyclohexene ring, a cyclopentane ring, a cyclopentene ring, or another monocyclic heterocyclic ring, such as indolyl, quinolyl, isoquinolyl, tetrahydroquinolyl, benzofuryl, benzothienyl and the like.

The designated number of carbons in heteroforms of alkyl, alkenyl and alkynyl includes the heteroatom count. For example, if heteroalkyl is defined as C1-C6, it will contain 1-6 C, N, O, or S atoms such that the heteroalkyl contains at least one C atom and at least one heteroatom, for example 1-5 carbons and 1 N atom, or 1-4 carbons and 2 N atoms. Similarly, when heteroalkyl is defined as C1-C6 or C1-C4, it would contain 1-5 carbons or 1-3 carbons respectively, i.e., at least one C is replaced by 0, N or S. Accordingly, when heteroalkenyl or heteroalkynyl is defined as C2-C6 (or C2-C4), it would contain 2-6 or 2-4 C, N, O, or S atoms, since the heteroalkenyl or heteroalkynyl contains at least one carbon atom and at least one heteroatom, e.g. 2-5 carbons and 1 N atom, or 2-4 carbons, and 2 O atoms. Further, heteroalkyl, heteroalkenyl or heteroalkynyl substituents may also contain one or more carbonyl groups. Examples of heteroalkyl, heteroalkenyl and heteroalkynyl groups include $CH_2OCH_3$, $CH_2N(CH_3)_2$, $CH_2OH$, $(CH_2)_n NR_2$, OR, COOR, $CONR_2$, $(CH_2)_n OR$, $(CH_2)_n COR$, $(CH_2)_n COOR$, $(CH_2)_n SR$, $(CH_2)_n SOR$, $(CH_2)_n SO_2R$, $(CH_2)_n CONR_2$, NRCOR, NRCOOR, $OCONR_2$, OCOR and the like wherein the R group contains at least one C and the size of the substituent is consistent with the definition of e.g., alkyl, alkenyl, and alkynyl, as described herein (e.g., n is 1, 2, 3, 4, 5, 6, 7, 8, 9, 10, 11, or 12).

As used herein, the terms "alkylene," "alkenylene," and "alkynylene," or the prefix "alk" refer to divalent or trivalent groups having a specified size, typically C1-C2, C1-C3, C1-C4, C1-C6, or C1-C8 for the saturated groups (e.g., alkylene or alk) and C2-C3, C2-C4, C2-C6, or C2-C8 for the unsaturated groups (e.g., alkenylene or alkynylene). They include straight-chain, branched-chain and cyclic forms as well as combinations of these, containing only C and H when unsubstituted. Because they are divalent, they can link together two parts of a molecule, as exemplified by X in the compounds described herein. Examples are methylene, ethylene, propylene, cyclopropan-1,1-diyl, ethylidene, 2-butene-1,4-diyl, and the like. These groups can be substituted by the groups typically suitable as substituents for alkyl, alkenyl and alkynyl groups as set forth herein. Thus C=O is a C1 alkylene that is substituted by =O, for example. For example, the term "alkaryl," as used herein, represents an aryl group, as defined herein, attached to the parent molecular group through an alkylene group, as defined herein, and the term "alkheteroaryl" refers to a heteroaryl group, as defined herein, attached to the parent molecular group through an alkylene group, as defined herein. The alkylene and the aryl or heteroaryl group are each optionally substituted as described herein.

Heteroalkylene, heteroalkenylene and heteroalkynylene are similarly defined as divalent groups having a specified size, typically C1-C3, C1-C4, C1-C6, or C1-C8 for the saturated groups and C2-C3, C2-C4, C2-C6, or C2-C8 for the unsaturated groups. They include straight chain, branched chain and cyclic groups as well as combinations of these, and they further contain at least one carbon atom but also contain one or more O, S or N heteroatoms or combinations thereof within the backbone residue, whereby each heteroatom in the heteroalkylene, heteroalkenylene or heteroalkynylene group replaces one carbon atom of the alkylene, alkenylene or alkynylene group to which the heteroform corresponds. As is understood in the art, these heteroforms do not contain more than three contiguous heteroatoms.

The term "alkylsulfonyl," as used herein, represents a heteroalkyl group that is described as an optionally substituted alkyl group, as described herein, that includes an $—S(O)_2—$ group.

The term "amino," as used herein, represents $—N(R^{N1})_2$, wherein each $R^{N1}$ is, independently, H, OH, $NO_2$, $N(R^{N2})_2$, $SO_2OR^{N2}$, $SO_2R^{N2}$, $SOR^{N2}$, $SO_2N(R^{N2})_2$, $SON(R^{N2})_2$, an N-protecting group, alkyl, alkenyl, alkynyl, alkoxy, aryl, alkaryl, cycloalkyl, alkcycloalkyl, heterocyclyl (e.g., heteroaryl), alkheterocyclyl (e.g., alkheteroaryl), or two $R^{N1}$ combine to form a heterocyclyl or an N-protecting group, and wherein each $R^{N2}$ is, independently, H, alkyl, or aryl. In a preferred embodiment, amino is $—NH_2$, or $—NHR^{N1}$, wherein $R^{N1}$ is, independently, OH, $NO_2$, $NH_2$, $NR^{N2}_2$, $SO_2OR^{N2}$, $SO_2R^{N2}$, $SOR^{N2}$, $SO_2N(R^{N2})_2$, $SON(R^{N2})_2$, alkyl, or aryl, and each $R^{N2}$ can be H, alkyl, or aryl. The term "aminoalkyl," as used herein, represents a heteroalkyl group, as defined herein, that is described as an alkyl group, as defined herein, substituted by an amino group, as defined herein. The alkyl and amino each can be further substituted with 1, 2, 3, or 4 substituent groups as described herein for the respective group. For example, the alkyl moiety may comprise an oxo (=O) substituent.

"Aromatic" moiety or "aryl" moiety refers to any monocyclic or fused ring bicyclic system which has the characteristics of aromaticity in terms of electron distribution throughout the ring system and includes a monocyclic or fused bicyclic moiety such as phenyl or naphthyl; "heteroaromatic" or "heteroaryl" also refers to such monocyclic or fused bicyclic ring systems containing one or more heteroatoms selected from O, S and N. The inclusion of a heteroatom permits inclusion of 5-membered rings to be considered aromatic as well as 6-membered rings. Thus, typical aromatic/heteroaromatic systems include pyridyl, pyrimidyl, indolyl, benzimidazolyl, benzotriazolyl, isoquinolyl, quinolyl, benzothiazolyl, benzofuranyl, thienyl, furyl, pyrrolyl, thiazolyl, oxazolyl, isoxazolyl, benzoxazolyl, benzoisoxazolyl, imidazolyl and the like. Because tautomers are theoretically possible, phthalimido is also considered aromatic. Typically, the ring systems contain 5-12 ring member atoms or 6-10 ring member atoms. In some embodiments, the aromatic or heteroaromatic moiety is a 6-membered aromatic rings system optionally containing 1-2 nitrogen atoms. More particularly, the moiety is an optionally substituted phenyl, pyridyl, indolyl, pyrimidyl, pyridazinyl, benzothiazolyl or benzimidazolyl, pyrazolyl, imidazolyl, isoxazolyl, thiazolyl, benzothiazolyl, indolyl. Even more particularly, such moiety is phenyl, pyridyl, or pyrimidyl and even more particularly, it is phenyl.

"O-aryl" or "O-heteroaryl" refers to aromatic or heteroaromatic systems which are coupled to another residue through an oxygen atom. A typical example of an O-aryl is phenoxy. Similarly, "arylalkyl" refers to aromatic and heteroaromatic systems which are coupled to another residue through a carbon chain, saturated or unsaturated, typically of C1-C8, C1-C6, or more particularly C1-C4 or C1-C3 when saturated or C2-C8, C2-C6, C2-C4, or C2-C3 when unsaturated, including the heteroforms thereof. For greater certainty, arylalkyl thus includes an aryl or heteroaryl group as defined above connected to an alkyl, heteroalkyl, alkenyl, heteroalkenyl, alkynyl or heteroalkynyl moiety also as defined above. Typical arylalkyls would be an aryl(C6-C12)alkyl(C1-C8), aryl(C6-C12)alkenyl(C2-C8), or aryl(C6-C12)alkynyl(C2-C8), plus the heteroforms. A typical example is phenylmethyl, commonly referred to as benzyl.

Halo may be any halogen atom, especially F, Cl, Br, or I, and more particularly it is fluoro or chloro.

The term "haloalkyl," as used herein, represents an alkyl group, as defined herein, substituted by a halogen group (i.e., F, Cl, Br, or I). A haloalkyl may be substituted with one, two, three, or, in the case of alkyl groups of two carbons or more, four halogens. Haloalkyl groups include perfluoroalkyls. In some embodiments, the haloalkyl group can be further substituted with 1, 2, 3, or 4 substituent groups as described herein for alkyl groups.

The term "hydroxy," as used herein, represents an —OH group.

The term "hydroxyalkyl," as used herein, represents an alkyl group, as defined herein, substituted by one to three hydroxy groups, with the proviso that no more than one hydroxy group may be attached to a single carbon atom of the alkyl group, and is exemplified by hydroxymethyl, dihydroxypropyl, and the like.

The term "N-protecting group," as used herein, represents those groups intended to protect an amino group against undesirable reactions during synthetic procedures. Commonly used N-protecting groups are disclosed in Greene, "Protective Groups in Organic Synthesis," 3$^{rd}$ Edition (John Wiley & Sons, New York, 1999), which is incorporated herein by reference. N-protecting groups include acyl, aryloyl, or carbamyl groups such as formyl, acetyl, propionyl, pivaloyl, t-butylacetyl, 2-chloroacetyl, 2-bromoacetyl, trifluoroacetyl, trichloroacetyl, phthalyl, o-nitrophenoxyacetyl, α-chlorobutyryl, benzoyl, 4-chlorobenzoyl, 4-bromobenzoyl, 4-nitrobenzoyl, and chiral auxiliaries such as protected or unprotected D, L or D, L-amino acids such as alanine, leucine, phenylalanine, and the like; sulfonyl-containing groups such as benzenesulfonyl, p-toluenesulfonyl, and the like; carbamate forming groups such as benzyloxycarbonyl, p-chlorobenzyloxycarbonyl, p-methoxybenzyloxycarbonyl, p-nitrobenzyloxycarbonyl, 2-nitrobenzyloxycarbonyl, p-bromobenzyloxycarbonyl, 3,4-dimethoxybenzyloxycarbonyl, 3,5-dimethoxybenzyl oxycarbonyl, 2,4-dimethoxybenzyloxycarbonyl, 4-methoxybenzyloxycarbonyl, 2-nitro-4,5-dimethoxybenzyloxycarbonyl, 3,4,5-trimethoxybenzyloxycarbonyl, 1-(p-biphenylyl)-1-methylethoxycarbonyl, α,α-dimethyl-3,5-dimethoxybenzyloxycarbonyl, benzhydryloxy carbonyl, t-butyloxycarbonyl, diisopropylmethoxycarbonyl, isopropyloxycarbonyl, ethoxycarbonyl, methoxycarbonyl, allyloxycarbonyl, 2,2,2,-trichloroethoxycarbonyl, phenoxycarbonyl, 4-nitrophenoxy carbonyl, fluorenyl-9-methoxycarbonyl, cyclopentyloxycarbonyl, adamantyloxycarbonyl, cyclohexyloxycarbonyl, phenylthiocarbonyl, and the like, alkaryl groups such as benzyl, triphenylmethyl, benzyloxymethyl, and the like and silyl groups such as trimethylsilyl, and the like. Preferred N-protecting groups are formyl, acetyl, benzoyl, pivaloyl, t-butylacetyl, alanyl, phenylsulfonyl, benzyl, t-butyloxycarbonyl (Boc), and benzyloxycarbonyl (Cbz).

In general, a substituent group (e.g., alkyl, alkenyl, alkynyl, or aryl (including all heteroforms defined above) may itself optionally be substituted by additional substituents. The nature of these substituents is similar to those recited with regard to the substituents on the basic structures above. Thus, where an embodiment of a substituent is alkyl, this alkyl may optionally be substituted by the remaining substituents listed as substituents where this makes chemical sense, and where this does not undermine the size limit of alkyl per se; e.g., alkyl substituted by alkyl or by alkenyl would simply extend the upper limit of carbon atoms for these embodiments, and is not included. For example, where a group is substituted, the group may be substituted with 1, 2, 3, 4, 5, or 6 substituents. Optional substituents include, but are not limited to: C1-C6 alkyl or heteroaryl, C2-C6 alkenyl or heteroalkenyl, C2-C6 alkynyl or heteroalkynyl, halogen; aryl, heteroaryl, azido(—N$_3$), nitro (—NO$_2$), cyano (—CN), acyloxy(—OC(=O)R'), acyl (—C(=O)R'), alkoxy (—OR'), amido (—NR'C(=O)R" or —C(=O)NRR'), amino (—NRR'), carboxylic acid (—CO$_2$H), carboxylic ester (—CO$_2$R'), carbamoyl (—OC(=O)NR'R" or —NRC(=O)OR'), hydroxy (—OH), isocyano (—NC), sulfonate (—S(=O)$_2$OR), sulfonamide (—S(=O)$_2$NRR' or —NRS(=O)$_2$R'), or sulfonyl (—S(=O)$_2$R), where each R or R' is selected, independently, from H, C1-C6 alkyl or heteroaryl, C2-C6 alkenyl or heteroalkenyl, 2C-6C alkynyl or heteroalkynyl, aryl, or heteroaryl. A substituted group may have, for example, 1, 2, 3, 4, 5, 6, 7, 8, or 9 substituents.

Typical optional substituents on aromatic or heteroaromatic groups include independently halo, CN, NO$_2$, CF$_3$, OCF$_3$, COOR', CONR'$_2$, OR', SR', SOR', SO$_2$R', NR'$_2$, NR'(CO)R',NR'C(O)OR', NR'C(O)NR'$_2$, NR'SO$_2$NR'$_2$, or NR'SO$_2$R', wherein each R' is independently H or an optionally substituted group selected from alkyl, alkenyl, alkynyl, heteroalkyl, heteroalkenyl, heteroalkynyl, heteroaryl, and aryl (all as defined above); or the substituent may be an optionally substituted group selected from alkyl, alkenyl, alkynyl, heteroalkyl, heteroalkenyl, heteroalkynyl, aryl, heteroaryl, O-aryl, O-heteroaryl and arylalkyl.

Optional substituents on a non-aromatic group (e.g., alkyl, alkenyl, and alkynyl groups), are typically selected from the same list of substituents suitable for aromatic or heteroaromatic groups, except as noted otherwise herein. A non-aromatic group may also include a substituent selected from =O and =NOR' where R' is H or an optionally substituted group selected from alkyl, alkenyl, alkynyl, heteroalkyl, heteroalkenyl, heteralkynyl, heteroaryl, and aryl (all as defined above).

The term an "effective amount" of an agent (e.g., a compound according to any of Formulas (I)-(XIII) or any of Compounds (1)-(236) of Table 1), as used herein, is that amount sufficient to effect beneficial or desired results, such as clinical results, and, as such, an "effective amount" depends upon the context in which it is being applied. For example, in the context of administering an agent that is a modulator of a voltage-gated ion channel (e.g., a sodium channel such as Na$_v$1.7 or Na$_v$ 1.8), an effective amount of an agent is, for example, an amount sufficient to achieve a change in sodium channel activity as compared to the response obtained without administration of the agent.

The term "pharmaceutical composition," as used herein, represents a composition containing a compound described herein (e.g., a compound according to any of Formulas (I)-(XIII) or any of Compounds (1)-(236) of Table 1) formulated with a pharmaceutically acceptable excipient. In some embodiments, the pharmaceutical composition is manufactured or sold with the approval of a governmental regulatory agency as part of a therapeutic regimen for the treatment of disease in a mammal. Pharmaceutical compositions can be formulated, for example, for oral administration in unit dosage form (e.g., a tablet, capsule, caplet, gelcap, or syrup); for topical administration (e.g., as a cream, gel, lotion, or ointment); for intravenous administration (e.g., as a sterile solution free of particulate emboli and in a solvent system suitable for intravenous use); or in any other formulation described herein.

A "pharmaceutically acceptable excipient," as used herein, refers any ingredient other than the compounds described herein (for example, a vehicle capable of suspending or dissolving the active compound) and having the properties of being nontoxic and non-inflammatory in a patient. Excipients may include, for example: antiadherents, antioxidants, binders, coatings, compression aids, disintegrants, dyes (colors), emollients, emulsifiers, fillers (diluents), film formers or coatings, flavors, fragrances, glidants (flow enhancers), lubricants, preservatives, printing inks, sorbents, suspensing or dispersing agents, sweeteners, or waters of hydration. Exemplary excipients include, but are not limited to: butylated hydroxytoluene (BHT), calcium carbonate, calcium phosphate (dibasic), calcium stearate, croscarmellose, crosslinked polyvinyl pyrrolidone, citric acid, crospovidone, cysteine, ethylcellulose, gelatin, hydroxypropyl cellulose, hydroxypropyl methylcellulose, lactose, magnesium stearate, maltitol, mannitol, methionine, methylcellulose, methyl paraben, microcrystalline cellulose, polyethylene glycol, polyvinyl pyrrolidone, povidone, pregelatinized starch, propyl paraben, retinyl palmitate, shellac, silicon dioxide, sodium carboxymethyl cellulose, sodium citrate, sodium starch glycolate, sorbitol, starch (corn), stearic acid, stearic acid, sucrose, talc, titanium dioxide, vitamin A, vitamin E, vitamin C, and xylitol.

The term "pharmaceutically acceptable prodrugs" as used herein, represents those prodrugs of the compounds of the present invention that are, within the scope of sound medical judgment, suitable for use in contact with the tissues of humans and animals with undue toxicity, irritation, allergic response, and the like, commensurate with a reasonable benefit/risk ratio, and effective for their intended use, as well as the zwitterionic forms, where possible, of the compounds of the invention.

The term "pharmaceutically acceptable salt," as use herein, represents those salts of the compounds described here (e.g., a compound according to any of Formulas (I)-(XIII) or any of Compounds (1)-(236) of Table 1) that are, within the scope of sound medical judgment, suitable for use in contact with the tissues of humans and animals without undue toxicity, irritation, allergic response and the like and are commensurate with a reasonable benefit/risk ratio. Pharmaceutically acceptable salts are well known in the art. For example, pharmaceutically acceptable salts are described in: Berge et al., *J. Pharmaceutical Sciences* 66:1-19, 1977 and in *Pharmaceutical Salts: Properties, Selection, and Use*, (Eds. P. H. Stahl and C. G. Wermuth), Wiley-VCH, 2008. The salts can be prepared in situ during the final isolation and purification of the compounds described herein or separately by reacting the free base group with a suitable organic acid.

The compounds of the invention may have ionizable groups so as to be capable of preparation as pharmaceutically acceptable salts. These salts may be acid addition salts involving inorganic or organic acids or the salts may, in the case of acidic forms of the compounds of the invention be prepared from inorganic or organic bases. Frequently, the compounds are prepared or used as pharmaceutically acceptable salts prepared as addition products of pharmaceutically acceptable acids or bases. Suitable pharmaceutically acceptable acids and bases are well-known in the art, such as hydrochloric, sulphuric, hydrobromic, acetic, lactic, citric, or tartaric acids for forming acid addition salts, and potassium hydroxide, sodium hydroxide, ammonium hydroxide, caffeine, various amines, and the like for forming basic salts. Methods for preparation of the appropriate salts are well-established in the art.

Representative acid addition salts include acetate, adipate, alginate, ascorbate, aspartate, benzenesulfonate, benzoate, bisulfate, borate, butyrate, camphorate, camphorsulfonate, citrate, cyclopentanepropionate, digluconate, dodecylsulfate, ethanesulfonate, fumarate, glucoheptonate, glycerophosphate, hemisulfate, heptonate, hexanoate, hydrobromide, hydrochloride, hydroiodide, 2-hydroxyethanesulfonate, lactobionate, lactate, laurate, lauryl sulfate, malate, maleate, malonate, methanesulfonate, 2-naphthalenesulfonate, nicotinate, nitrate, oleate, oxalate, palmitate, pamoate, pectinate, persulfate, 3-phenylpropionate, phosphate, picrate, pivalate, propionate, stearate, succinate, sulfate, tartrate, thiocyanate, toluenesulfonate, undecanoate, valerate salts and the like. Representative alkali or alkaline earth metal salts include sodium, lithium, potassium, calcium, magnesium and the like, as well as nontoxic ammonium, quaternary ammonium, and amine cations, including, but not limited to ammonium, tetramethylammonium, tetraethylammonium, methylamine, dimethylamine, trimethylamine, triethylamine, ethylamine and the like.

The term "pharmaceutically acceptable solvate" as used herein means a compound as described herein (e.g., a compound according to any of Formulas (I)-(XIII) or any of Compounds (1)-(236) of Table 1) where molecules of a suitable solvent are incorporated in the crystal lattice. A suitable solvent is physiologically tolerable at the dosage administered. For example, solvates may be prepared by crystallization, recrystallization, or precipitation from a solution that includes organic solvents, water, or a mixture thereof. Examples of suitable solvents are ethanol, water (for example, mono-, di-, and tri-hydrates), N-methylpyrrolidinone (NMP), dimethyl sulfoxide (DMSO), N,N'-dimethylformamide (DMF), N,N'-dimethylacetamide (DMAC), 1,3-dimethyl-2-imidazolidinone (DMEU), 1,3-dimethyl-3,4,5,6-tetrahydro-2-(1H)-pyrimidinone (DMPU), acetonitrile (ACN), propylene glycol, ethyl acetate, benzyl alcohol, 2-pyrrolidone, benzyl benzoate, and the like. When water is the solvent, the molecule is referred to as a "hydrate."

The term "prevent," as used herein, refers to prophylactic treatment or treatment that prevents one or more symptoms or conditions of a disease, disorder, or conditions described herein (for example, pain (e.g., chronic or acute pain), epilepsy, Alzheimer's disease, Parkinson's disease, cardiovascular disease, diabetes, cancer, sleep disorders, obesity, psychosis such as schizophrenia, overactive bladder, renal disease, neuroprotection, addiction, and male birth control). Preventative treatment can be initiated, for example, prior to ("pre-exposure prophylaxis") or following ("post-exposure prophylaxis") an event that precedes the onset of the disease, disorder, or conditions. Preventive treatment that includes administration of a compound described herein (e.g., a compound according to any of Formulas (I)-(XIII) or any of Compounds (1)-(236) of Table 1), or a pharmaceutically acceptable salt or solvate thereof, or a pharmaceutical composition thereof, can be acute, short-term, or chronic. The doses administered may be varied during the course of preventative treatment.

The term "prodrug," as used herein, represents compounds that are rapidly transformed in vivo to the parent compound of the above formula, for example, by hydrolysis in blood. Prodrugs of the compounds described herein may be conventional esters. Some common esters that have been utilized as prodrugs are phenyl esters, aliphatic (C1-C8 or C8-C24) esters, cholesterol esters, acyloxymethyl esters, carbamates, and amino acid esters. For example, a compound that contains an OH group may be acylated at this position in its prodrug form. A thorough discussion is provided in T. Higuchi and V. Stella, *Pro-drugs as Novel Delivery Systems*, Vol. 14 of the A.C.S. Symposium Series, Edward B. Roche, ed., *Bioreversible Carriers in Drug Design*, American Pharmaceutical Association and Pergamon Press, 1987, and Judkins et al., *Synthetic Communications* 26(23):4351-4367, 1996, each of which is incorporated herein by reference. Preferably, prodrugs of the compounds of the present invention are suitable for use in contact with the tissues of humans and animals with undue toxicity, irritation, allergic response, and the like, commensurate with a reasonable benefit/risk ratio, and effective for their intended use.

In addition, the compounds of the invention may be coupled through conjugation to substances designed to alter the pharmacokinetics, for targeting, or for other reasons. Thus, the invention further includes conjugates of these compounds. For example, polyethylene glycol is often coupled to substances to enhance half-life; the compounds may be coupled to liposomes covalently or noncovalently or to other particulate carriers. They may also be coupled to targeting agents such as antibodies or peptidomimetics, often through linker moieties. Thus, the invention is also directed to compounds (e.g., a compound according to any of Formulas (I)-(XIII) or any of Compounds (1)-(236) of Table 1) when modified so as to be included in a conjugate of this type.

As used herein, and as well understood in the art, "to treat" a condition or "treatment" of the condition (e.g., the conditions described herein such as pain (e.g., chronic or acute pain), epilepsy, Alzheimer's disease, Parkinson's disease, cardiovascular disease, diabetes, cancer, sleep disorders, obesity, psychosis such as schizophrenia, overactive bladder, renal disease, neuroprotection, addiction, and male birth control) is an approach for obtaining beneficial or desired results, such as clinical results. Beneficial or desired results can include, but are not limited to, alleviation or amelioration of one or more symptoms or conditions; diminishment of extent of disease, disorder, or condition; stabilized (i.e., not worsening) state of disease, disorder, or condition; preventing spread of disease, disorder, or condition; delay or slowing the progress of the disease, disorder, or condition; amelioration or palliation of the disease, disorder, or condition; and remission (whether partial or total), whether detectable or undetectable. "Palliating" a disease, disorder, or condition means that the extent and/or undesirable clinical manifestations of the disease, disorder, or condition are lessened and/or time course of the progression is slowed or lengthened, as compared to the extent or time course in the absence of treatment.

The term "unit dosage form" refers to a physically discrete unit suitable as a unitary dosage for human subjects and other mammals, each unit containing a predetermined quantity of active material calculated to produce the desired therapeutic effect, in association with any suitable pharmaceutical excipient or excipients. Exemplary, non-limiting unit dosage forms include a tablet (e.g., a chewable tablet), caplet, capsule (e.g., a hard capsule or a soft capsule), lozenge, film, strip, gelcap, and syrup.

In some cases, the compounds of the invention contain one or more chiral centers. The invention includes each of the isolated stereoisomeric forms as well as mixtures of stereoisomers in varying degrees of chiral purity, including racemic mixtures. It also encompasses the various diastereomers and tautomers that can be formed.

Compounds useful in the invention may also be isotopically labeled compounds. Useful isotopes include hydrogen, carbon, nitrogen, oxygen, phosphorous, fluorine, and chlorine, (e.g., $^{2}H$, $^{3}H$, $^{13}C$, $^{14}C$, $^{15}N$, $^{18}O$, $^{17}O$, $^{31}P$, $^{32}P$, $^{35}S$, $^{18}F$, and $^{36}Cl$). Isotopically labeled compounds can be prepared by synthesizing a compound using a readily available isotopically labeled reagent in place of a non-isotopically labeled reagent. In some embodiments, the compound (e.g., a compound according to any of Formulas (I)-(XIII) or any of Compounds (1)-(236) of Table 1), or a composition that includes the compound, has the natural abundance of each element present in the compound.

The compounds described herein (e.g., a compound according to any of Formulas (I)-(XIII) or any of Compounds (1)-(236) of Table 1) are also useful for the manufacture of a medicament useful to treat conditions requiring modulation of voltage-gated ion channel activity (e.g., sodium channel activity), and, in particular, $Na_v 1.7$ or $Na_v 1.8$ channel activity.

Other features and advantages of the invention will be apparent from the following detailed description, the drawings, and the claims.

BRIEF DESCRIPTION OF THE DRAWINGS

FIGS. 1A-1B show the modulation of ion channel activity by the compounds described herein.

FIGS. 2A-2C and 3A-3C show data obtained in the spinal nerve ligation (SNL) assay for select compounds of the invention.

DETAILED DESCRIPTION OF THE INVENTION

Compounds

Figure 2A:
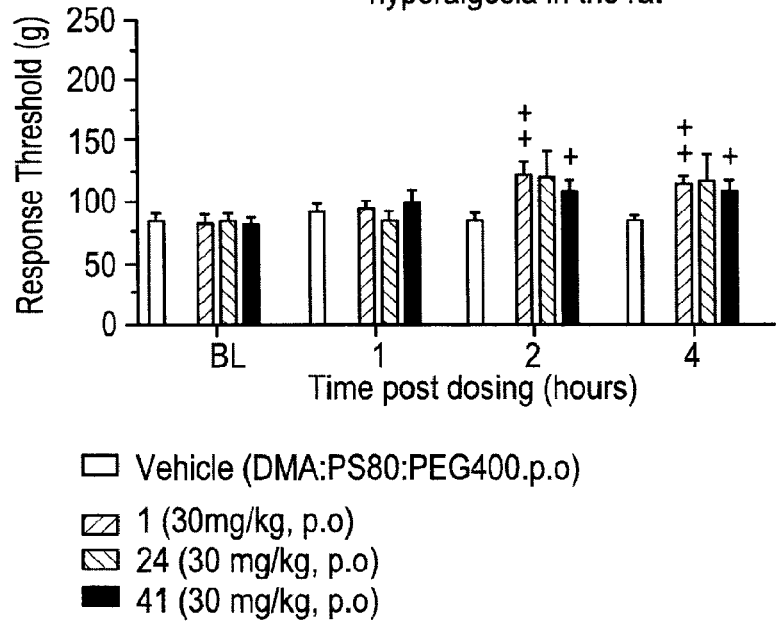
Figure 2B:
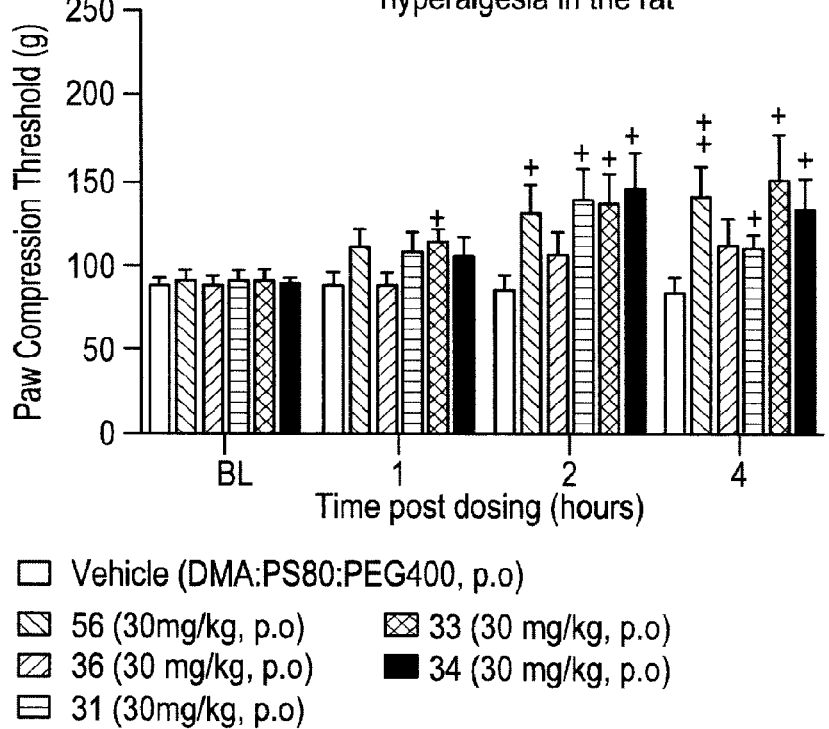

The invention features compounds that can modulate the activity of voltage-gated ion channels (e.g., voltage-gated sodium channels). These compounds can also be used to treat disorders such as pain, epilepsy, Parkinson's disease, mood disorders, psychosis (e.g., schizophrenia), tinnitus, amyotropic lateral sclerosis, glaucoma, ischaemia, spasticity disorders, obsessive compulsive disorder, restless leg syndrome, and Tourette syndrome. Exemplary compounds described herein include compounds that have a structure according to the following formula,

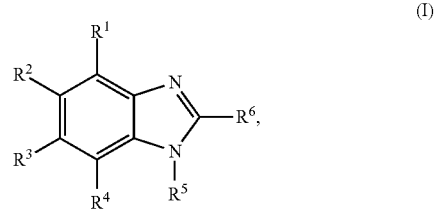

or a pharmaceutically acceptable salt or solvate thereof, where each of $R^1$, $R^2$, $R^3$, and $R^4$ is selected, independently, from H, optionally substituted C1-C6 alkyl, optionally substituted C1-C6 haloalkyl, optionally substituted C6-C10 aryl, or optionally substituted 5 to 6-membered heteroaryl, where at least one of $R^1$, $R^2$, $R^3$, and $R^4$ is halogen or optionally substituted C1-C6 haloalkyl;

$R^5$ is H, optionally substituted C1-C6 alkyl, or optionally substituted C1-C10 heteroalkyl;

$R^6$ is —$R^{6A}$ or —$CH_2R^{6B}$;

$R^{6A}$ is $NH_2$, optionally substituted cyclopropyl, optionally substituted azetidine, optionally substituted cyclopentyl, optionally substituted pyrazole, optionally substituted pyrrole, optionally substituted pyrrolidine, optionally substituted thiazolidine, optionally substituted thiazolidine-1,1-dioxide, optionally substituted pyrimidine, optionally substituted C1-C10 aminoalkyl, optionally substituted C1-C10 hydroxyalkyl, optionally substituted C1-C10 alkoxyalkyl, optionally substituted C1-C10 haloalkyl, or optionally substituted C1-C10 alkylsulfonyl; or $R^{6A}$ has a structure according to

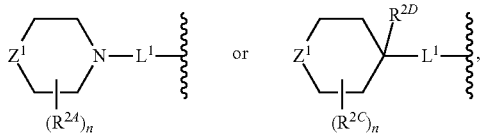

where
n is an integer between 0-4;
$Z^1$ is $CH_2$, NH, $NCH_3$, or O;
$L^1$ is $-CH_2$, $-CHR^{4A}$, $-CH_2C(=O)$, $-C(=O)CH_2$, $-CH_2C(=O)NH$, $-CH_2C(=O)NHCH_2$, or $-CH_2NHC(=O)CH_2$;
each $R^{2A}$ and $R^{2C}$, when present, is selected from OH, $N(R^{2B})_2$, halogen, and unsubstituted C1-C3 alkyl, or two $R^{2A}$ combine to form an oxo (=O) group, and wherein no more than two $R^{2A}$ combine to form an oxo group; and
each $R^{2B}$ is, independently, H or unsubstituted C1-C6 alkyl;
$R^{2D}$ is H, OH, or $NH_2$;
and
$R^{6B}$ is optionally substituted cyclopropyl, optionally substituted azetidine, optionally substituted cyclopentyl, optionally substituted pyrazole, optionally substituted pyrrole, optionally substituted pyrrolidine, optionally substituted thiazolidine, optionally substituted thiazolidine-1,1-dioxide, or optionally substituted pyrimidine.

In some embodiments, $R^5$ is H.
In other embodiments, $R^5$ is optionally substituted C1-C10 heteroalkyl.
In certain embodiments, $R^2$ and $R^4$ are both $CF_3$, F, or Cl.
In still other embodiments, $R^2$ and $R^3$ are both $CF_3$, F, or Cl.
In some embodiments, $R^6$ is $-CH_2R^{6B}$, and $R^{6B}$ is optionally substituted azetidine.
In certain embodiments, $R^6$ is optionally substituted C1-C10 aminoalkyl.
In other embodiments, the C1-C10 aminoalkyl includes an oxo (=O) substituent, an alkoxy substituent, an N-sulfonyl group, or any combination thereof.
Other embodiments (e.g., Formulas (II)-(XIII) and any of compounds (1)-(236) of Table 1), as well as exemplary methods for the synthesis of these compounds, are described herein.

Utility and Administration

The compounds described herein (e.g., a compound according to any of Formulas (I)-(XIII) or any of Compounds (1)-(236) of Table 1) are useful in the methods of the invention and, while not bound by theory, are believed to exert their desirable effects through their ability to modulate the activity of voltage-gated ion channels, e.g., the activity of sodium channels such as the $Na_v$ 1.7 and $Na_v$1.8 channels. The compounds described herein (e.g., a compound according to any of Formulas (I)-(XIII) or any of Compounds (1)-(236) of Table 1) can also be used for the treatment of certain conditions such as pain, epilepsy, migraine, Parkinson's disease, mood disorders, schizophrenia, psychosis, tinnitus, amyotropic lateral sclerosis, glaucoma, ischaemia, spasticity disorders, obsessive compulsive disorder, restless leg syndrome, and Tourette syndrome.

Modulation of Sodium Channels

There are nine $Na_v1$ α-subunit isoforms: $Na_v$1.1-1.9 (see, e.g., Yu et al., Genome Biolog, 4:207, 2003). In addition to pain, other conditions associated with voltage-dependent sodium channel activity include seizures (e.g., $Na_v$1.1), epilepsy (e.g., $Na_v$1.2), neurodegeneration (e.g., $Na_v$1.1, $Na_v$1.2), myotonia (e.g., $Na_v$1.4), arrhythmia (e.g., $Na_v$1.5), and movement disorders (e.g., $Na_v$1.6) as described in PCT Publication No. WO 2008/118758, herein incorporated by reference. The expression of particular isoforms in particular tissues can influence the therapeutic effects of sodium channel modulators. For example, the $Na_v$1.4 and $Na_v$1.5 isoforms are largely found in skeletal and cardiac myocytes (see, e.g., Gold, Exp Neurol. 210(1): 1-6, 2008).

Sodium Channel Activity and Pain

Voltage-dependent ion channels in pain-sensing neurons are currently of great interest in developing drugs to treat pain. For example, blocking voltage-dependent sodium channels in pain-sensing neurons can block pain signals by interrupting initiation and transmission of the action potential.

Studies also indicate that particular sodium channel isoforms are predominantly expressed in peripheral sensory neurons associated with pain sensation; for example, $Na_v$1.7, $Na_v$1.8 and $Na_v$ 1.9 activity are thought to be involved in inflammatory, and possibly neuropathic, pain (see, e.g., Cummins et al., Pain, 131(3):243-257, 2007). The $Na_v$1.3 isoform has also been implicated in pain, e.g., pain associated with tissue injury (Gold, Exp Neurol. 210(1): 1-6, 2008).

The $Na_v$1.7 and $Na_v$1.8 channel subtypes act as major contributors to both inflammatory and neuropathic pain (vide infra). Recently, mutations have been identified in the $Na_v$1.7 channel that lead either to a gain of channel function (Dib-Hajj et al., Brain 128:1847-1854, 2005) or more commonly to a loss of channel function (Chatelier et al., J. Neurophisiol. 99:2241-50, 2008). These mutations underlie human heritable disorders such as erythermalgia (Yang et al., J Med Genet. 41(3) 171-4, 2004), paroxysmal extreme pain disorder (Fertleman et al., Neuron. 52(5) 767-74, 2006), and congenital indifference to pain (Cox et al., Nature 444(7121):894-8, 2006). Behavioral studies have shown in mice that inflammatory and acute mechanosensory pain is reduced when $Na_v$1.7 is knocked out in $Na_v$1.8-positive neurons (Nassar et al., Proc Natl Acad Sci USA. 101(34): 12706-11, 2004). In addition, siRNA of $Na_v$1.7 attenuates inflammatory hyperalgesia (Yeomans et al., Hum Gene Ther. 16(2) 271-7, 2005).

The $Na_v$1.8 isoform is selectively expressed in sensory neurons and has been identified as a target for the treatment of pain, e.g., chronic pain (e.g., Swanwick et al., Neurosci. Lett. 486:78-83, 2010). The role of $Na_v$1.8 in inflammatory (Khasar et al. Neurosci Lett. 256(1):17-20, 1998), neuropathic and mechanical hyperalgesia (Joshi et al., Pain 123 (1-2):75-82, 2006) has also emerged using molecular techniques to knockdown $Na_v$ 1.8, which has been shown to reduce the maintenance of these different pain states.

Lacosamide is a functionalized amino acid that has shown effectiveness as an analgesic in several animal models of neuropathic pain and is currently in late stages of clinical development for epilepsy and diabetic neuropathic pain. One mode of action that has been validated for lacosamide is inhibition of voltage-gated sodium channel activity by selective inhibition with the slow-inactivated conformation of the channel (Sheets et al., Journal of Pharmacology and Experimental Therapeutics, 326(1) 89-99 (2008)). Modulators of sodium channels, including clinically relevant compounds, can exhibit a pronounced state-dependent binding, where sodium channels that are rapidly and repeatedly activated and inactivated are more readily blocked. In a simplified scheme, voltage-gated sodium channels have four distinct states: open, closed, fast-inactivated and slow-inactivated. Classic sodium channel modulators, such as lidocaine, are believed to exhibit the highest affinity for the fast-inactivated state. However, alteration of the slow inactivated state is also clinically relevant.

Modulation of Calcium Channels

The entry of calcium into cells through voltage-gated calcium channels mediates a wide variety of cellular and physiological responses, including excitation-contraction coupling, hormone secretion and gene expression (e.g., Miller et al., *Science* 235:46-52 (1987); Augustine et al., *Annu Rev Neurosci* 10: 633-693 (1987)). In neurons, calcium channels directly affect membrane potential and contribute to electrical properties such as excitability, repetitive firing patterns and pacemaker activity. Calcium entry further affects neuronal functions by directly regulating calcium-dependent ion channels and modulating the activity of calcium-dependent enzymes such as protein kinase C and calmodulin-dependent protein kinase II. An increase in calcium concentration at the presynaptic nerve terminal triggers the release of neurotransmitter, which also affects neurite outgrowth and growth cone migration in developing neurons.

Calcium channels mediate a variety of normal physiological functions, and are also implicated in a number of human disorders as described herein. For example, calcium channels also have been shown to mediate the development and maintenance of the neuronal sensitization and hyperexcitability processes associated with neuropathic pain, and provide attractive targets for the development of analgesic drugs (reviewed in Vanegas et al., *Pain* 85: 9-18 (2000)). Native calcium channels have been classified by their electrophysiological and pharmacological properties into T-, L-, N-, P/Q- and R-types (reviewed in Catterall, *Annu Rev Cell Dev Biol* 16: 521-555, 2000; Huguenard, *Annu Rev Physiol* 58: 329-348, 1996). The L-, N- and P/Q-type channels activate at more positive potentials (high voltage-activated) and display diverse kinetics and voltage-dependent properties (Id.). T-type channels can be distinguished by having a more negative range of activation and inactivation, rapid inactivation, slow deactivation, and smaller single-channel conductances. There are three subtypes of T-type calcium channels that have been molecularly, pharmacologically, and elecrophysiologically identified: these subtypes have been termed $\alpha_{1G}$, $\alpha_{1H}$, and $\alpha_{1I}$ (alternately called Cav 3.1, Cav 3.2 and Cav 3.3 respectively).

T-type calcium channels are involved in various medical conditions. In mice lacking the gene expressing the 3.1 subunit, resistance to absence seizures was observed (Kim et al., *Mol. Cell Neurosci.* 18(2): 235-245 (2001)). Other studies have also implicated the 3.2 subunit in the development of epilepsy (Su et al., *J. Neurosci.* 22: 3645-3655 (2002)). There is also evidence that some existing anticonvulsant drugs, such as ethosuximide, function through the blockade of T-type channels (Gomora et al., *Mol. Pharmacol.* 60: 1121-1132 (2001)).

Low voltage-activated calcium channels are highly expressed in tissues of the cardiovascular system. There is also a growing body of evidence that suggests that T-type calcium channels are abnormally expressed in cancerous cells and that blockade of these channels may reduce cell proliferation in addition to inducing apoptosis. Recent studies also show that the expression of T-type calcium channels in breast cancer cells is proliferation state dependent, i.e. the channels are expressed at higher levels during the fast-replication period, and once the cells are in a non-proliferation state, expression of this channel is minimal. Therefore, selectively blocking calcium channel entry into cancerous cells may be a valuable approach for preventing tumor growth (e.g., PCT Patent Application Nos. WO 05/086971 and WO 05/77082; Taylor et al., *World J. Gastroenterol.* 14(32): 4984-4991 (2008); Heo et al., *Biorganic & Medicinal Chemistry Letters* 18:3899-3901 (2008)).

T-type calcium channels may also be involved in still other conditions. A recent study also has shown that T-type calcium channel antagonists inhibit high-fat diet-induced weight gain in mice. In addition, administration of a selective T-type channel antagonist reduced body weight and fat mass while concurrently increasing lean muscle mass (e.g., Uebele et al., *The Journal of Clinical Investigation,* 119(6): 1659-1667 (2009)). T-type calcium channels may also be involved in pain (see for example: US Patent Publication No. 2003/0086980; PCT Publication Nos. WO 03/007953 and WO 04/000311). In addition to cardiovascular disease, epilepsy (see also US Patent Application No. 2006/0025397), cancer, and chronic or acute pain, T-type calcium channels have been implicated in diabetes (US Patent Publication No. 2003/0125269), sleep disorders (US Patent Publication No. 2006/0003985), Parkinson's disease and psychosis such as schizophrenia (US Patent Publication No. 2003/0087799); overactive bladder (Sui et al., *British Journal of Urology International* 99(2): 436-441 (2007); US Patent Publication No. 2004/0197825), renal disease (Hayashi et al., *Journal of Pharmacological Sciences* 99: 221-227 (2005)), anxiety and alcoholism (US Patent Publication No. 2009/0126031), neuroprotection, and male birth control.

The modulation of ion channels by the compounds described herein (e.g., a compound according to any of Formulas (I)-(XIII) or any of Compounds (1)-(236) of Table 1) can be measured according to methods known in the art (e.g., in the references provided herein). Modulators of ion channels, e.g., voltage gated sodium and calcium ion channels, and the medicinal chemistry or methods by which such compounds can be identified, are also described in, for example: Birch et al., *Drug Discovery Today,* 9(9):410-418 (2004); Audesirk, "Chapter 6-Electrophysiological Analysis of Ion Channel Function," *Neurotoxicology: Approaches and Methods,* 137-156 (1995); Camerino et al., "Chapter 4: Therapeutic Approaches to Ion Channel Diseases," *Advances in Genetics,* 64:81-145 (2008); Petkov, "Chapter 16-Ion Channels," *Pharmacology: Principles and Practice,* 387-427 (2009); Standen et al., "Chapter 15-Patch Clamping Methods and Analysis of Ion Channels," *Principles of Medical Biology, Vol.* 7, Part 2, 355-375 (1997); Xu et al., *Drug Discovery Today,* 6(24):1278-1287 (2001); and Sullivan et al., *Methods Mol. Biol.* 114:125-133 (1999). Exemplary experimental methods are also provided in the Examples.

Diseases and Conditions

Exemplary conditions that can be treated using the compounds described herein include pain (e.g., chronic or acute pain), epilepsy, Alzheimer's disease, Parkinson's disease, diabetes; cancer; sleep disorders; obesity; mood disorders, psychosis such as schizophrenia; overactive bladder; renal disease, neuroprotection, and addiction. For example, the condition can be pain (e.g., neuropathic pain or post-surgery pain), epilepsy, migraine, Parkinson's disease, mood disorders, schizophrenia, psychosis, tinnitus, amyotropic lateral sclerosis, glaucoma, ischaemia, spasticity disorders, obsessive compulsive disorder, restless leg syndrome, and Tourette syndrome.

Epilepsy as used herein includes but is not limited to partial seizures such as temporal lobe epilepsy, absence seizures, generalized seizures, and tonic/clonic seizures.

Cancer as used herein includes but is not limited to breast carcinoma, neuroblastoma, retinoblastoma, glioma, prostate carcinoma, esophageal carcinoma, fibrosarcoma, colorectal carcinoma, pheochromocytoma, adrenocarcinoma, insulinoma, lung carcinoma, melanoma, and ovarian cancer.

Acute pain as used herein includes but is not limited to nociceptive pain and post-operative pain. Chronic pain includes but is not limited by: peripheral neuropathic pain (e.g., post-herpetic neuralgia, diabetic neuropathic pain, neuropathic cancer pain, HIV-associated neuropathy, erythromelalgia, failed back-surgery syndrome, trigeminal neuralgia, or phantom limb pain); central neuropathic pain (e.g., multiple sclerosis related pain, Parkinson disease related pain, post-stroke pain, post-traumatic spinal cord injury pain, lumbosacral radiculopathy, cervical radiculopathy, brachial radiculopathy, or pain in dementia); musculoskeletal pain such as osteoarthritic pain and fibromyalgia syndrome; inflammatory pain (e.g., inflammatory pain caused by rheumatoid arthritis, juvenile idiopathic arthritis, ankylosing spondylitis, psoriatic arthritis, inflammatory bowel disease, primary dysmenorrhea, or endometriosis); headache such as migraine, cluster headache, tension headache syndrome, facial pain, headache caused by other diseases; visceral pain such as interstitial cystitis, irritable bowel syndrome and chronic pelvic pain syndrome; and mixed pain such as lower back pain, neck and shoulder pain, burning mouth syndrome and complex regional pain syndrome.

In treating osteoarthritic pain, joint mobility can also improve as the underlying chronic pain is reduced. Thus, use of compounds of the present invention to treat osteoarthritic pain inherently includes use of such compounds to improve joint mobility in patients suffering from osteoarthritis.

The compounds described herein can be tested for efficacy in any standard animal model of pain. Various models test the sensitivity of normal animals to intense or noxious stimuli (physiological or nociceptive pain). These tests include responses to thermal, mechanical, or chemical stimuli. Thermal stimuli usually involve the application of hot stimuli (typically varying between 42-55° C.) including, for example: radiant heat to the tail (the tail flick test), radiant heat to the plantar surface of the hindpaw (the Hargreaves test), the hotplate test, and immersion of the hindpaw or tail into hot water. Immersion in cold water, acetone evaporation, or cold plate tests may also be used to test cold pain responsiveness. Tests involving mechanical stimuli typically measure the threshold for eliciting a withdrawal reflex of the hindpaw to graded strength monofilament von Frey hairs or to a sustained pressure stimulus to a paw (e.g., the Ugo Basile analgesiometer). The duration of a response to a standard pinprick may also be measured. When using a chemical stimulus, the response to the application or injection of a chemical irritant (e.g., capsaicin, mustard oil, bradykinin, ATP, formalin, acetic acid) to the skin, muscle joints or internal organs (e.g., bladder or peritoneum) is measured.

In addition, various tests assess pain sensitization by measuring changes in the excitability of the peripheral or central components of the pain neural pathway. In this regard, peripheral sensitization (i.e., changes in the threshold and responsiveness of high threshold nociceptors) can be induced by repeated heat stimuli as well as the application or injection of sensitizing chemicals (e.g., prostaglandins, bradykinin, histamine, serotonin, capsaicin, or mustard oil). Central sensitization (i.e., changes in the excitability of neurons in the central nervous system induced by activity in peripheral pain fibers) can be induced by noxious stimuli (e.g., heat), chemical stimuli (e.g., injection or application of chemical irritants), or electrical activation of sensory fibers.

Various pain tests developed to measure the effect of peripheral inflammation on pain sensitivity can also be used to study the efficacy of the compounds (Stein et al., *Pharmacol. Biochem. Behav.* (1988) 31: 445-451; Woolf et al., *Neurosci.* (1994) 62: 327-331). Additionally, various tests assess peripheral neuropathic pain using lesions of the peripheral nervous system. One such example is the "axotomy pain model" (Watson, *J. Physiol.* (1973) 231:41). Other similar tests include the SNL test which involves the ligation of a spinal segmental nerve (Kim and Chung *Pain* (1992) 50: 355), the Seltzer model involving partial nerve injury (Seltzer, *Pain* (1990) 43: 205-18), the spared nerve injury (SNI) model (Decosterd and Woolf, *Pain* (2000) 87:149), chronic constriction injury (CCI) model (Bennett (1993) *Muscle Nerve* 16: 1040), tests involving toxic neuropathies such as diabetes (streptozocin model), pyridoxine neuropathy, taxol, vincristine, and other antineoplastic agent-induced neuropathies, tests involving ischaemia to a nerve, peripheral neuritis models (e.g., CFA applied perineurally), models of post-herpetic neuralgia using HSV infection, and compression models.

In all of the above tests, outcome measures may be assessed, for example, according to behavior, electrophysiology, neurochemistry, or imaging techniques to detect changes in neural activity.

Exemplary models of pain are also described in the Examples provided herein.

In addition to being able to modulate a particular voltage-gated ion channel, e.g., a sodium channel, it may be desirable that the compound has very low activity with respect to the hERG $K^+$ channel, which is expressed in the heart: compounds that block this channel with high potency may cause reactions which are fatal. See, e.g., Bowlby et al., "hERG (KCNH2 or $K_v11.1$ $K^+$ Channels: Screening for Cardiac Arrhythmia Risk," *Curr. Drug Metab.* 9(9):965-70 (2008)). Thus, for a compound that modulates sodium channel activity, it may also be shown that the hERG $K^+$ channel is not inhibited or only minimally inhibited as compared to the inhibition of the primary channel targeted. Similarly, it may be desirable that the compound does not inhibit cytochrome p450, an enzyme that is required for drug detoxification. Such compounds may be particularly useful in the methods described herein.

Pharmaceutical Compositions

For use as treatment of human and animal subjects, the compounds of the invention can be formulated as pharmaceutical or veterinary compositions. Depending on the subject to be treated, the mode of administration, and the type of treatment desired—e.g., prevention, prophylaxis, or therapy—the compounds are formulated in ways consonant with these parameters. A summary of such techniques is found in *Remington: The Science and Practice of Pharmacy*, 21$^{st}$ *Edition*, Lippincott Williams & Wilkins, (2005); and *Encyclopedia of Pharmaceutical Technology*, eds. J. Swarbrick and J. C. Boylan, 1988-1999, Marcel Dekker, New York, each of which is incorporated herein by reference.

The compounds described herein (e.g., a compound according to any of Formulas (I)-(XIII) or any of Compounds (1)-(236) of Table 1) may be present in amounts totaling 1-95% by weight of the total weight of the composition. The composition may be provided in a dosage form that is suitable for intraarticular, oral, parenteral (e.g., intravenous, intramuscular), rectal, cutaneous, subcutaneous, topical, transdermal, sublingual, nasal, vaginal, intravesicular, intraurethral, intrathecal, epidural, aural, or ocular administration, or by injection, inhalation, or direct contact with the nasal, genitourinary, gastrointesitnal, reproductive or oral mucosa. Thus, the pharmaceutical composition may be in the form of, e.g., tablets, capsules, pills, powders, granulates, suspensions, emulsions, solutions, gels including hydrogels, pastes, ointments, creams, plasters, drenches, osmotic delivery devices, suppositories, enemas, injectables, implants, sprays, preparations suitable for iontophoretic delivery, or aerosols. The compositions may be formulated according to conventional pharmaceutical practice.

In general, for use in treatment, the compounds described herein (e.g., a compound according to any of Formulas (I)-(XIII) or any of Compounds (1)-(236) of Table 1) may be used alone, as mixtures of two or more compounds or in combination with other pharmaceuticals. An example of other pharmaceuticals to combine with the compounds described herein (e.g., a compound according to any of Formulas (I)-(XIII) or any of Compounds (1)-(236) of Table 1) would include pharmaceuticals for the treatment of the same indication. For example, in the treatment of pain, a compound may be combined with another pain relief treatment such as an NSAID, or a compound which selectively inhibits COX-2, or an opioid, or an adjuvant analgesic such as an antidepressant. Another example of a potential pharmaceutical to combine with the compounds described herein (e.g., a compound according to any of Formulas (I)-(XIII) or any of Compounds (1)-(236) of Table 1) would include pharmaceuticals for the treatment of different yet associated or related symptoms or indications. Depending on the mode of administration, the compounds will be formulated into suitable compositions to permit facile delivery. Each compound of a combination therapy may be formulated in a variety of ways that are known in the art. For example, the first and second agents of the combination therapy may be formulated together or separately. Desirably, the first and second agents are formulated together for the simultaneous or near simultaneous administration of the agents.

The compounds of the invention may be prepared and used as pharmaceutical compositions comprising an effective amount of a compound described herein (e.g., a compound according to any of Formulas (I)-(XIII) or any of Compounds (1)-(236) of Table 1) and a pharmaceutically acceptable carrier or excipient, as is well known in the art. In some embodiments, the composition includes at least two different pharmaceutically acceptable excipients or carriers.

Formulations may be prepared in a manner suitable for systemic administration or topical or local administration. Systemic formulations include those designed for injection (e.g., intramuscular, intravenous or subcutaneous injection) or may be prepared for transdermal, transmucosal, or oral administration. The formulation will generally include a diluent as well as, in some cases, adjuvants, buffers, preservatives and the like. The compounds can be administered also in liposomal compositions or as microemulsions.

For injection, formulations can be prepared in conventional forms as liquid solutions or suspensions or as solid forms suitable for solution or suspension in liquid prior to injection or as emulsions. Suitable excipients include, for example, water, saline, dextrose, glycerol and the like. Such compositions may also contain amounts of nontoxic auxiliary substances such as wetting or emulsifying agents, pH buffering agents and the like, such as, for example, sodium acetate, sorbitan monolaurate, and so forth.

Various sustained release systems for drugs have also been devised. See, for example, U.S. Pat. No. 5,624,677, which is herein incorporated by reference.

Systemic administration may also include relatively non-invasive methods such as the use of suppositories, transdermal patches, transmucosal delivery and intranasal administration. Oral administration is also suitable for compounds of the invention. Suitable forms include syrups, capsules, and tablets, as is understood in the art.

For administration to animal or human subjects, the dosage of the compounds of the invention may be, for example, 0.01-50 mg/kg (e.g., 0.01-15 mg/kg or 0.1-10 mg/kg). For example, the dosage can be 10-30 mg/kg.

Each compound of a combination therapy, as described herein, may be formulated in a variety of ways that are known in the art. For example, the first and second agents of the combination therapy may be formulated together or separately.

The individually or separately formulated agents can be packaged together as a kit. Non-limiting examples include, but are not limited to, kits that contain, e.g., two pills, a pill and a powder, a suppository and a liquid in a vial, two topical creams, etc. The kit can include optional components that aid in the administration of the unit dose to patients, such as vials for reconstituting powder forms, syringes for injection, customized IV delivery systems, inhalers, etc. Additionally, the unit dose kit can contain instructions for preparation and administration of the compositions. The kit may be manufactured as a single use unit dose for one patient, multiple uses for a particular patient (at a constant dose or in which the individual compounds may vary in potency as therapy progresses); or the kit may contain multiple doses suitable for administration to multiple patients ("bulk packaging"). The kit components may be assembled in cartons, blister packs, bottles, tubes, and the like.

Formulations for oral use include tablets containing the active ingredient(s) in a mixture with non-toxic pharmaceutically acceptable excipients. These excipients may be, for example, inert diluents or fillers (e.g., sucrose, sorbitol, sugar, mannitol, microcrystalline cellulose, starches including potato starch, calcium carbonate, sodium chloride, lactose, calcium phosphate, calcium sulfate, or sodium phosphate); granulating and disintegrating agents (e.g., cellulose derivatives including microcrystalline cellulose, starches including potato starch, croscarmellose sodium, alginates, or alginic acid); binding agents (e.g., sucrose, glucose, sorbitol, acacia, alginic acid, sodium alginate, gelatin, starch, pregelatinized starch, microcrystalline cellulose, magnesium aluminum silicate, carboxymethylcellulose sodium, methylcellulose, hydroxypropyl methylcellulose, ethylcellulose, polyvinylpyrrolidone, or polyethylene glycol); and lubricating agents, glidants, and antiadhesives (e.g., magnesium stearate, zinc stearate, stearic acid, silicas, hydrogenated vegetable oils, or talc). Other pharmaceutically acceptable excipients can be colorants, flavoring agents, plasticizers, humectants, buffering agents, and the like.

Two or more compounds may be mixed together in a tablet, capsule, or other vehicle, or may be partitioned. In one example, the first compound is contained on the inside of the tablet, and the second compound is on the outside, such that a substantial portion of the second compound is released prior to the release of the first compound.

Formulations for oral use may also be provided as chewable tablets, or as hard gelatin capsules wherein the active ingredient is mixed with an inert solid diluent (e.g., potato starch, lactose, microcrystalline cellulose, calcium carbonate, calcium phosphate or kaolin), or as soft gelatin capsules wherein the active ingredient is mixed with water or an oil medium, for example, peanut oil, liquid paraffin, or olive oil. Powders, granulates, and pellets may be prepared using the ingredients mentioned above under tablets and capsules in a conventional manner using, e.g., a mixer, a fluid bed apparatus or a spray drying equipment.

Dissolution or diffusion controlled release can be achieved by appropriate coating of a tablet, capsule, pellet, or granulate formulation of compounds, or by incorporating the compound into an appropriate matrix. A controlled release coating may include one or more of the coating substances mentioned above and/or, e.g., shellac, beeswax, glycowax, castor wax, carnauba wax, stearyl alcohol, glyceryl monostearate, glyceryl distearate, glycerol palmitostearate, ethylcellulose, acrylic resins, dl-polylactic acid, cellulose acetate butyrate, polyvinyl chloride, polyvinyl acetate, vinyl pyrrolidone, polyethylene, polymethacrylate, methylmethacrylate, 2-hydroxymethacrylate, methacrylate hydrogels, 1,3 butylene glycol, ethylene glycol methacrylate, and/or polyethylene glycols. In a controlled release matrix formulation, the matrix material may also include, e.g., hydrated methylcellulose, carnauba wax and stearyl alcohol, carbopol 934, silicone, glyceryl tristearate, methyl acrylate-methyl methacrylate, polyvinyl chloride, polyethylene, and/or halogenated fluorocarbon.

The liquid forms in which the compounds and compositions of the present invention can be incorporated for administration orally include aqueous solutions, suitably flavored syrups, aqueous or oil suspensions, and flavored emulsions with edible oils such as cottonseed oil, sesame oil, coconut oil, or peanut oil, as well as elixirs and similar pharmaceutical vehicles.

Generally, when administered to a human, the oral dosage of any of the compounds of the combination of the invention will depend on the nature of the compound, and can readily be determined by one skilled in the art. Typically, such dosage is normally about 0.001 mg to 2000 mg per day, desirably about 1 mg to 1000 mg per day, and more desirably about 5 mg to 500 mg per day. Dosages up to 200 mg per day may be necessary.

Administration of each drug in a combination therapy, as described herein, can, independently, be one to four times daily for one day to one year, and may even be for the life of the patient. Chronic, long-term administration may be indicated.

Synthesis

The reaction scheme and Examples are intended to illustrate the synthesis of a representative number of compounds. Accordingly, the Examples are intended to illustrate but not to limit the invention. Additional compounds not specifically exemplified may be synthesized using conventional methods in combination with the methods described herein.

EXAMPLES

Example 1

Synthesis of (4,6-bis(trifluoromethyl)-1H-benzo[d]imidazol-2-yl) methanamine (5)

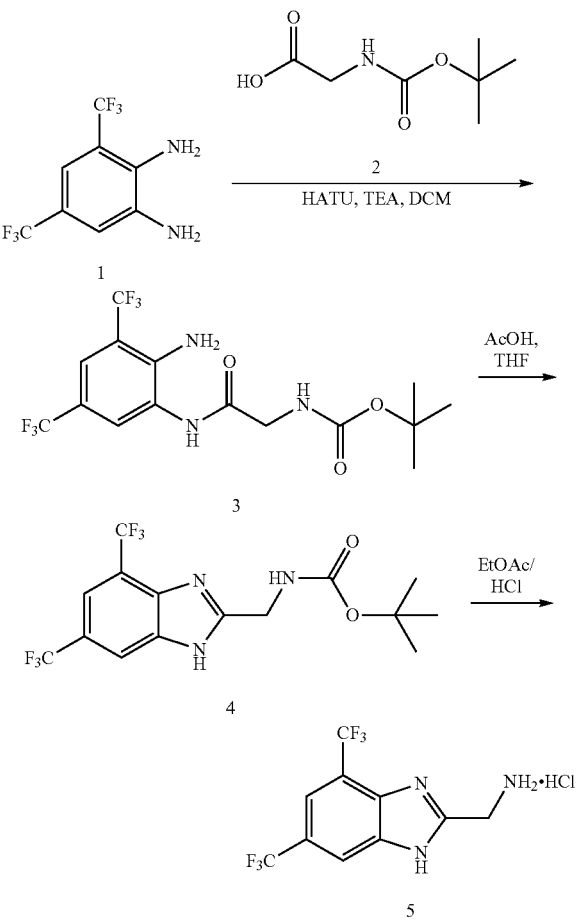

Synthesis of tert-butyl (2-((2-amino-3,5-bis(trifluoromethyl)phenyl)amino)-2-oxoethyl)carbamate (3)

3,5-Bis(trifluoromethyl)benzene-1,2-diamine (1) (3.0 g, 12.3 mol), 2-((tert-butoxycarbonyl)amino)acetic acid (2) (2.1 g, 12.3 mmol), HATU (6.4 g, 17.2 mmol), and triethylamine (TEA; 3.5 mL, 25 mmol) were stirred in dichloromethane (DCM; 50 mL) at room temperature for 17 hours. The reaction was diluted with DCM (100 mL), washed sequentially with $NH_4Cl$ (saturated solution), $NaHCO_3$ (saturated solution), and brine. The organics were separated, dried ($Na_2SO_4$), and concentrated in vacuo. The residue was purified by automated column chromatography (EtOAc/petroleum ether, 35/65) to give tert-butyl (2-((2-amino-3,5-bis(trifluoromethyl)phenyl)amino)-2-oxoethyl)carbamate (3) (3.07 g, 61.7%); Confirmed by LCMS (Positive ion mode).

Synthesis of tert-Butyl ((4,6-bis(trifluoromethyl)-1H-benzo[d]imidazol-2-yl)methyl)carbamate (4)

tert-Butyl (2-((2-amino-3,5-bis(trifluoromethyl)phenyl)amino)-2-oxoethyl)carbamate (3) (1.4 g, 3.5 mmol) was heated in THF/AcOH (95/5, 20 mL) using a microwave at 140° C. for 2.5 hours. The reaction was concentrated in vacuo, taken up in EtOAc, and washed with NaHCO₃ (saturated solution) to neutralize. The organic layer was separated, dried (Na₂SO₄), and concentrated in vacuo. The residue was purified by automated column chromatography (EtOAc/PE, 50:50) to give tert-Butyl ((4,6-bis(trifluoromethyl)-1H-benzo[d]imidazol-2-yl)methyl)carbamate (4), (730 mg, 54%); confirmed by LCMS (Positive ion mode)).

Synthesis of (4,6-bis(trifluoromethyl)-1H-benzo[d]imidazol-2-yl)methanamine hydrochloride (5)

tert-Butyl ((4,6-bis(trifluoromethyl)-1H-benzo[d]imidazol-2-yl)methyl)carbamate (4) (730 mg, 1.9 mmol) was taken up in EtOAc, and the solution was flushed with HCl (g) for 5 minutes. The resultant suspension was stirred at room temperature for 25 minutes then concentrated in vacuo. The resultant solid was dried under high vacuum for 14 hours to give (4,6-bis(trifluoromethyl)-1H-benzo[d]imidazol-2-yl)methanamine hydrochloride (5), in a quantitative manner; ¹H NMR (300 mHz, CD₃OD) δ 4.57 (s, 2H), 7.81 (s, 1H), 8.21 (s, 1H).

Example 2

Synthesis of 2-amino-N-((5,7-bis(trifluoromethyl)-1H-benzo[d]imidazol-2-yl)methyl)acetamide hydrochloride (7)

TEA (0.73 mL, 5.2 mmol) were stirred in DCM at room temperature for 14 hours. The reaction was diluted with DCM (100 mL) and washed sequentially with NH₄Cl (saturated solution), NaHCO₃ (saturated solution), and brine. The organics were separated, dried (Na₂SO₄), and concentrated in vacuo. The residue was purified by automated column chromatography (EtOAc/PE, 50/50) to give tert-butyl (2-(((5,7-bis(trifluoromethyl)-1H-benzo[d]imidazol-2-yl)methyl)amino)-2-oxoethyl)carbamate (6) (732 mg, 64%; Confirmed by LCMS (positive ion mode)).

Synthesis of 2-amino-N-((5,7-bis(trifluoromethyl)-1H-benzo[d]imidazol-2-yl)methyl)acetamide hydrochloride (7)

tert-Butyl (2-(((5,7-bis(trifluoromethyl)-1H-benzo[d]imidazol-2-yl)methyl)amino)-2-oxoethyl)carbamate (6) (732 mg, 1.66 mmol) was taken up in EtOAc, and the solution flushed with HCl (g) for 5 minutes. The suspension was stirred at room temperature for 20 minutes, concentrated in vacuo, and the residue purified by reverse phase HPLC to give 2-amino-N-((5,7-bis(trifluoromethyl)-1H-benzo[d]imidazol-2-yl)methyl)acetamide hydrochloride (7); ¹H NMR (300 mHz, CD₃OD) δ 3.45 (s, 2H), 5.04 (s, 2H), 8.18 (s, 1H), (8.49, S, 1H).

Example 3

Synthesis of 1-((4,6-bis(trifluoromethyl)-1H-benzo[d]imidazol-2-yl)methyl)-3-(tert-butyl)urea (9)

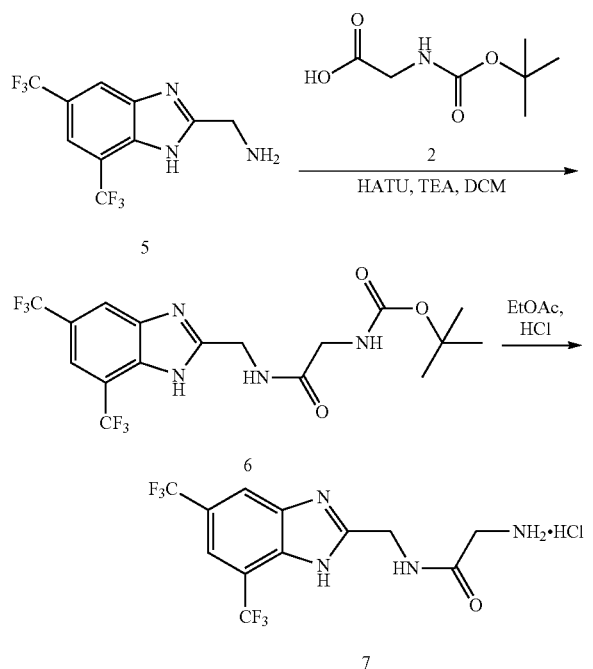

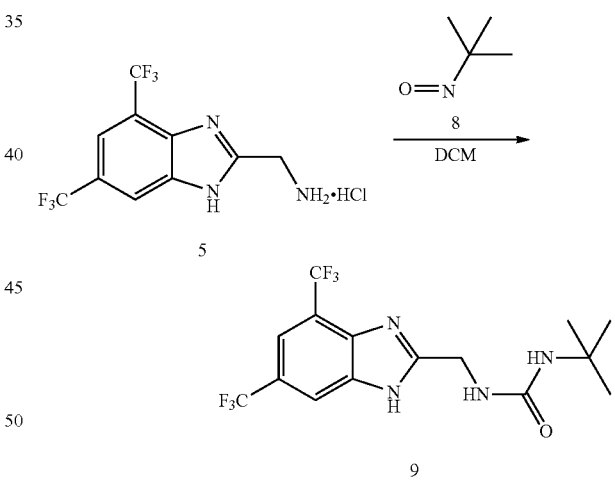

Synthesis of tert-butyl (2-(((5,7-bis(trifluoromethyl)-1H-benzo[d]imidazol-2-yl)methyl)amino)-2-oxoethyl)carbamate (6)

(4,6-Bis(trifluoromethyl)-1H-benzo[d]imidazol-2-yl)methanamine hydrochloride (5) (1 g, 2.6 mmol), BOC-gly (2) (4.55 mg, 2.6 mmol), HATU (1.35 g, 3.64 mmol), and Synthesis of 1-((4,6-bis(trifluoromethyl)-1H-benzo[d]imidazol-2-yl)methyl)-3-(tert-butyl)urea (9)

(4,6-Bis(trifluoromethyl)-1H-benzo[d]imidazol-2-yl)methanamine hydrochloride (5) (250 mg, 0.88 mmol) and TEA (0.25 mL, 1.8 mmol) were stirred in DCM. tert-Butyl isocyanate (8) (105 μL, 0.9 mmol) was added and the reaction stirred at room temperature for 1 h. The reaction was concentrated in vacuo and the residue purified by reverse phase HPLC to give 1-((4,6-bis(trifluoromethyl)-1H-benzo[d]imidazol-2-yl)methyl)-3-(tert-butyl)urea (9). Confirmed by LCMS (positive ion mode).

Example 4

Synthesis of 5-(3-chloro-4-fluorophenyl)-2-(pyrimidin-5-ylmethyl)-1H-benzo[d]imidazole (15)

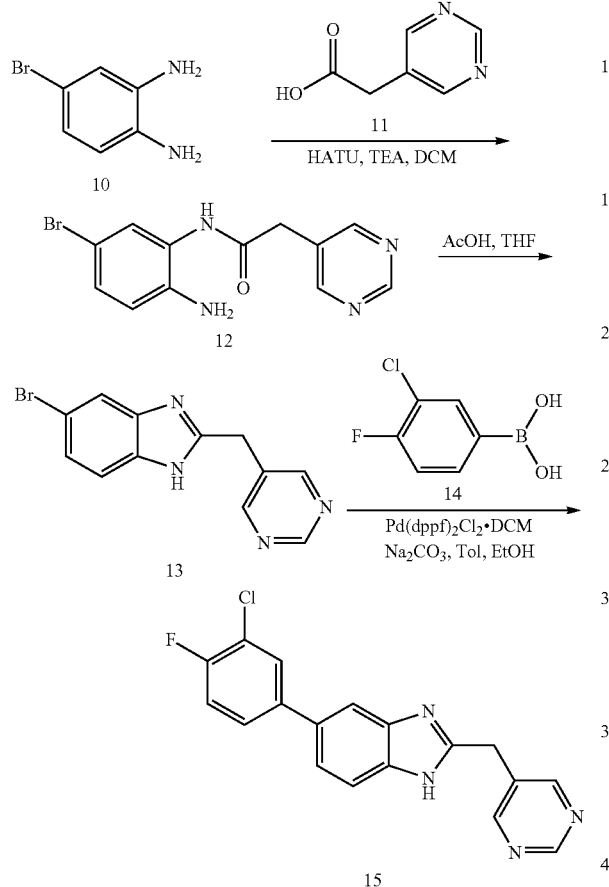

Preparation of N-(2-amino-5-bromophenyl)-2-(pyrimidin-5-yl)acetamide (12)

To a solution of 4-bromobenzene-1,2-diamine (10) (0.281 g, 1.5 mmol), 2-(pyrimidin-5-yl)acetic acid (11) (0.207 g, 1.5 mmol), and HATU (0.741 g, 1.95 mmol) in DCM (50 ml) was added triethylamine (0.63 ml, 4.5 mmol). The reaction mixture was stirred at room temperature overnight. The solution was washed with saturated sodium bicarbonate (50 ml) and brine (50 ml). The DCM solution was dried over sodium sulfate and concentrated. The residue was purified by automated column chromatography columned using DCM and methanol as eluents. Yield 0.4 g, 87%. MS: m/z 306.9 (M+H$^+$).

Preparation of 5-bromo-2-(pyrimidin-5-ylmethyl)-1H-benzo[d]imidazole (13)

A solution of N-(2-amino-5-bromophenyl)-2-(pyrimidin-5-yl)acetamide (12) (0.4 g, 1.3 mmol) in THF (12 ml) and acetic acid (7 ml) was reacted in the microwave at 145° C. for 3 hours. The solvents were removed. The residue was dissolved in ethyl acetate (50 ml) and washed with saturated sodium bicarbonate (30 ml) and brine (30 ml). The ethyl acetate solution was dried over sodium sulfate and concentrated. The residue was purified by automated column chromatography using DCM and methanol as eluents. Yield 0.345 g, 91%. MS: m/z 288.9 (M+H$^+$).

Preparation of 5-(3-chloro-4-fluorophenyl)-2-(pyrimidin-5-ylmethyl)-1H-benzo[d]imidazole (15)

Pd(dppf)$_2$Cl$_2$.DCM (0.274 g, 0.336 mmol) was added to a suspension of 5-bromo-2-(pyrimidin-5-ylmethyl)-1H-benzo[d]imidazole (13) (0.345 g, 1.12 mmol), 3-chloro-4-fluorobenzene boronic acid (14) (0.234 g, 1.34 mmol), and sodium carbonate (0.594 g, 5.6 mmol) in ethanol (7 ml) and toluene (7 ml). The reaction mixture was stirred at 130° C. overnight. The deep brown solution was filtered through Celite and concentrated. The residue was purified by automated column chromatography using DCM and methanol as eluents. Yield 0.15 g, 40%. MS: m/z 338.9 (M+H$^+$).

Example 5

Synthesis of (5,7-bis(trifluoromethyl)-1H-benzo[d]imidazol-2-yl)methanol (21)

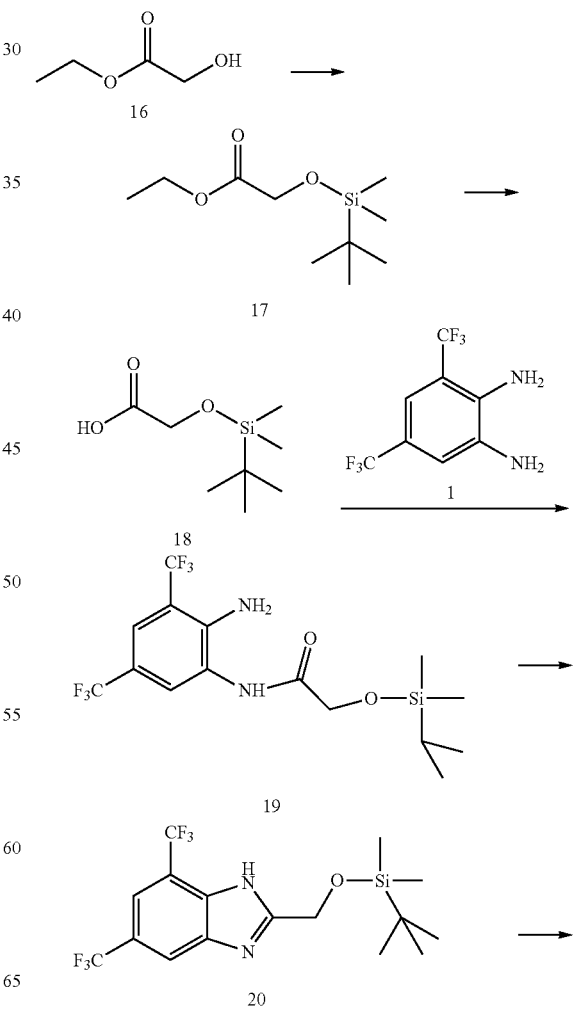

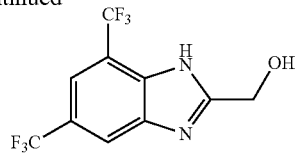

21

Preparation of ethyl 2-((tert-butyldimethylsilyl)oxy)acetate (17)

A solution of ethyl 2-hydroxyacetate (16) (3.12 g, 30 mmol) and imidazole (2.45 g, 36 mmol) in DCM (100 ml) was added tert-butylchlorodimethylsilane (5.43 g, 36 mmol) at 0° C. and the reaction mixture was stirred at 0° C. for 1 hour. The reaction mixture was washed with saturated sodium bicarbonate (50 ml) and brine (50 ml). The DCM solution was dried over sodium sulfate and concentrated. The residual (17)(6.68 g, 100% yield) was used in the next step without further purification.

Preparation of 2-((tert-butyldimethylsilyl)oxy)acetic acid (18)

A solution of ethyl 2-((tert-butyldimethylsilyl)oxy)acetate (17) (6.68 g, 30 mmol) in methanol (30 ml) was added 2N NaOH solution (30 ml). The mixture was then stirred at room temperature for 2 hours. The reaction mixture was concentrated, diluted with water, and acidified with 2N HCl to pH 4-5. The aqueous solution was extracted with ethyl acetate 3 times. The combined ethyl acetate solution was washed with brine and dried over sodium sulfate and concentrated. The residual (18) was used in the next step without further purification. Yield 2.19 g, 38%. MS, m/z 189.1 (M–H$^+$).

Preparation of N-(2-amino-3,5-bis(trifluoromethyl)phenyl)-2-((isopropyldimethylsilyl)oxy)acetamide (19)

A solution of 3,5-bis(trifluoromethyl)benzene-1,2-diamine (1) (1.28 g, 5.26 mmol), 2-((tert-butyldimethylsilyl)oxy)acetic acid (18) (1 g, 5.26 mmol) and HATU (2.6 g, 6.84 mmol) in DMF (15 ml) was reacted in the microwave at 80° C. for 2 hours. The reaction mixture was diluted with ethyl acetate. The solution was washed with saturated sodium bicarbonate and brine. The ethyl acetate solution was dried over sodium sulfate and concentrated. The residue (19) was purified by automated column chromatography using petroleum ether and ethyl acetate as eluents. Yield 0.84 g, 40%. MS, m/z 403.0 (M+H$^+$).

Preparation of 2-(((tert-butyldimethylsilyl)oxy)methyl)-5,7-bis(trifluoromethyl)-1H-benzo[d]imidazole (20)

A solution of N-(2-amino-3,5-bis(trifluoromethyl)phenyl)-2-((isopropyl dimethylsilyl)oxy)acetamide (19) (0.84 g, 2.09 mmol) in THF (14 ml) and acetic acid (7 ml) was reacted in the microwave at 145° C. for 3 hours. The solvents were removed. The residue was dissolved in ethyl acetate (50 ml) and washed with saturated sodium bicarbonate (30 ml) and brine (30 ml). The ethyl acetate solution was dried over sodium sulfate and concentrated. The residue (20) was purified by automated column chromatography using pet ether and ethyl acetate as eluents. Yield 0.5 g, 60%. MS, m/z 399.0 (M+H$^+$).

Preparation of (5,7-bis(trifluoromethyl)-1H-benzo[d]imidazol-2-yl)methanol (21)

To a solution of 2-(((tert-butyldimethylsilyl)oxy)methyl)-5,7-bis(trifluoromethyl)-1H-benzo[d]imidazole (20) (0.5 g, 1.26 mmol) in THF (15 ml) was added 1M TBAF solution in THF (1.7 ml, 1.7 mmol) at 0° C. The reaction mixture was stirred at room temperature overnight. The solvent was removed. The residue was dissolved in ethyl acetate (50 ml) and washed with brine (30 ml). The ethyl acetate solution was dried over sodium sulfate and concentrated. The residue of (34) was purified by automated column chromatography using petroleum ether and ethyl acetate as eluents. Yield 0.22 g, 61%. MS, m/z 284.9 (M+H$^+$).

Example 6

Synthesis of (1-((4,6-bis(trifluoromethyl)-1H-benzo[d]imidazol-2-yl)methyl)-1-methylurea (24)

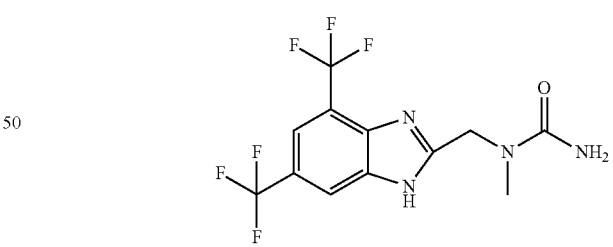

Preparation of (1-((4,6-bis(trifluoromethyl)-1H-benzo[d]imidazol-2-yl)methyl)-1-methylurea (24)

A solution of 1-(4,6-bis(trifluoromethyl)-1H-benzo[d]imidazol-2-yl)-N-methylmethanamine hydrochloride (22) (0.4 g, 1.19 mmol) and urea (23) (0.11 g, 1.83 mmol) in water (10 ml) was refluxed overnight. At this time, crystals separated from the liquid and were then collected by filtration. The precipitated product (24) was washed with water and dried. Yield 0.3 g, 72%. MS, m/z 340.22 (M+H$^+$).

Example 7

Synthesis of (1-((4,6-bis(trifluoromethyl)-1H-benzo[d]imidazol-2-yl)methyl)-1-N-methylsulfuric diamide (26)

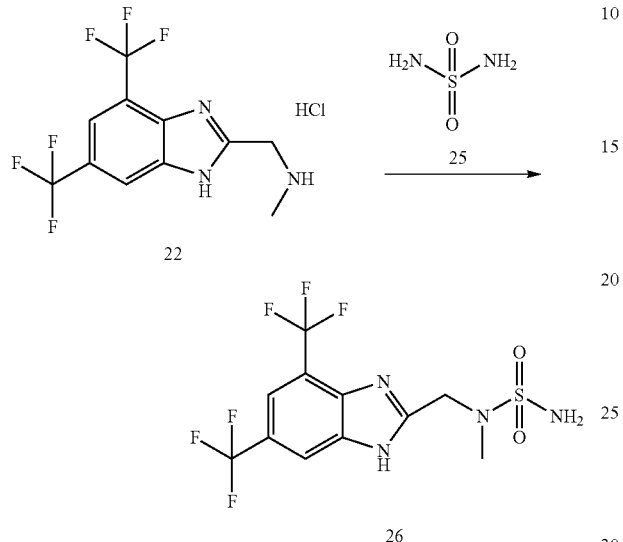

Preparation of (1-((4,6-bis(trifluoromethyl)-1H-benzo[d]imidazol-2-yl)methyl)-1-N-methylsulfuric diamide (26)

A solution of 1-(4,6-bis(trifluoromethyl)-1H-benzo[d]imidazol-2-yl)-N-methylmethanamine hydrochloride (22) (0.2 g, 0.6 mmol), sulfamide (25) (0.16 g, 1.68 mmol) in dioxane (15 ml) was heated to reflux for 6 hours. The reaction mixture was then cooled, and the solvent was evaporated. The residue was dissolved in water (10 ml), and the aqueous was extracted with ethyl acetate three times. The combined ethyl acetate layers were combined, dried, and evaporated. The residue (26) was purified by automated column chromatography using petroleum ether and ethyl acetate as eluents. Yield 70%. MS, m/z 376.28 (M+H$^+$).

Example 8

Synthesis of 4,6-bis(trifluoromethyl)-1H-benzo[d]imidazol-2-amine (28)

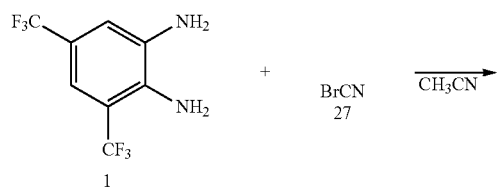

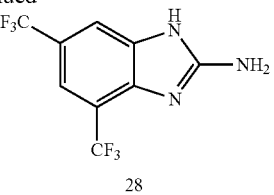

Preparation of 4,6-bis(trifluoromethyl)-1H-benzo[d]imidazol-2-amine (28)

To a solution of 3,5-bis(trifluoromethyl)benzene-1,2-diamine (1) (0.40 g, 1.6 mmol) in acetonitrile (15 mL) was added a solution of cyanogen bromide in acetonitrile (27) (5 M, 0.66 mL, 3.3 mmol). The resultant mixture was allowed to stir at room temperature for 23 hours. At this time, the reaction was concentrated in vacuo, and the crude product was purified by automated flash chromatography to afford the (28); confirmed by LCMS (positive ion mode)).

Example 9

Synthesis of 2-((methylsulfonyl)methyl)-4,6-bis(trifluoromethyl)-1H-benzo[d]imidazole (32)

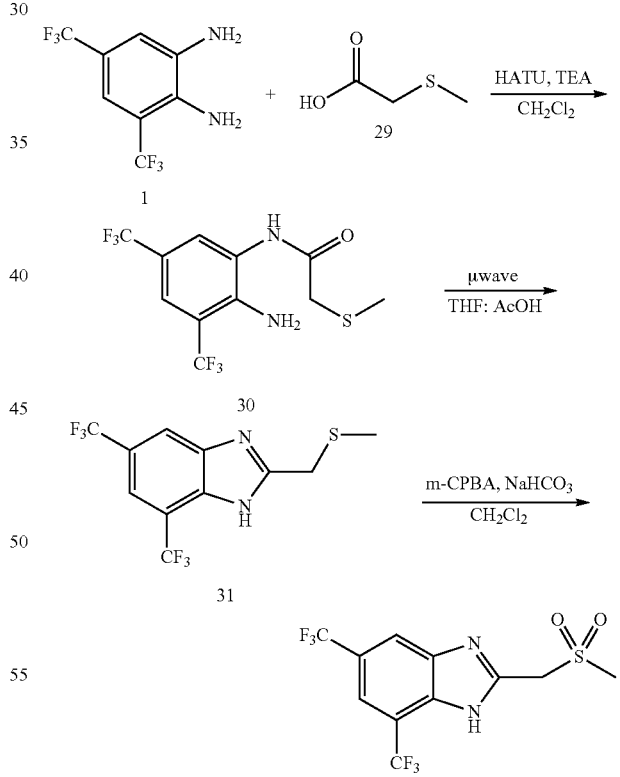

Preparation of N-(2-amino-3,5-bis(trifluoromethyl)phenyl)-2-(methylthio)acetamide (30)

To a mixture of 3,5-bis(trifluoromethyl)benzene-1,2-diamine (1) (0.50 g, 2.1 mmol), 2-(methylthio)acetic acid (29)

(0.22 g, 2.1 mmol) and HATU (1.01 g, 2.67 mmol) in dichloromethane (15 mL) was added triethylamine (0.9 mL, 6 mmol). The resultant solution was stirred at room temperature for 24 hours. The reaction was then washed with a saturated aqueous solution of sodium bicarbonate (2×30 mL). The organic phase was then dried over anhydrous sodium sulfate and concentrated in vacuo. The crude product was purified by automated flash chromatography (2:1 hexane:ethyl acetate) to afford the title compound (30) (0.40 g, 59%; confirmed by LCMS (positive ion mode).) as a pale yellow oil, which crystallized on standing. The other regioisomer was not observed during the course of purification.

Preparation of 2-((methylthio)methyl)-4,6-bis(trifluoromethyl)-1H-benzo[d]imidazole (31)

To a solution of N-(2-amino-3,5-bis(trifluoromethyl)phenyl)-2-(methylthio)acetamide (30) (0.40 g, 1.2 mmol) in tetrahydrofuran (3 mL) was added glacial acetic acid (2 mL). The reaction was sealed in a microwave reaction vial and heated at 130° C. for 30 minutes. The resultant solution was concentrated in vacuo, taken up in ethyl acetate (40 mL), and washed with a saturated aqueous solution of sodium bicarbonate (2×10 mL). The organic phase was then dried over anhydrous sodium sulfate and concentrated in vacuo. The crude product was purified by automated flash chromatography (2:1 hexane:ethyl acetate) to afford the title compound (31) (0.34 g, 89%; confirmed by LCMS (positive ion mode)) as a yellow solid.

Preparation of 2-((methylsulfonyl)methyl)-4,6-bis(trifluoromethyl)-1H-benzo[d]imidazole (32)

To a solution of 2-((methylthio)methyl)-4,6-bis(trifluoromethyl)-1H-benzo[d]imidazole (31) (0.34 g, 1.1 mmol) in dichloromethane (20 mL) was added m-CPBA (77%, 0.73 g, 3.2 mmol) and sodium bicarbonate (0.45 g, 5.4 mmol). The resultant mixture was stirred at room temperature for 17 hours, at which time dichloromethane was added (30 mL). To the resultant solution was added an aqueous solution of sodium hydroxide (2 M, 10 mL) and a saturated aqueous solution of sodium thiosulfate (10 mL). The mixture was allowed to stir for 1 hours. The aqueous layer was subsequently separated, acidified with hydrochloric acid (2 M, 12 mL), extracted with ethyl acetate (3×30 mL), and dried over anhydrous sodium sulfate. The resultant oil was taken up in an ethyl acetate:methanol mixture (1:1) and filtered. The filtrate was then concentrated in vacuo, and the product was purified by automated flash chromatography to afford the title compound (32) (confirmed by LCMS (positive ion mode)).

Example 10

Synthesis of N-((5,7-bis(trifluoromethyl)-1H-benzo[d]imidazol-2-yl)methyl)methanesulfonamide (34)

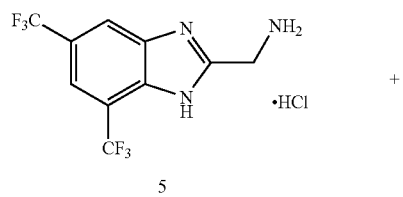

5

+

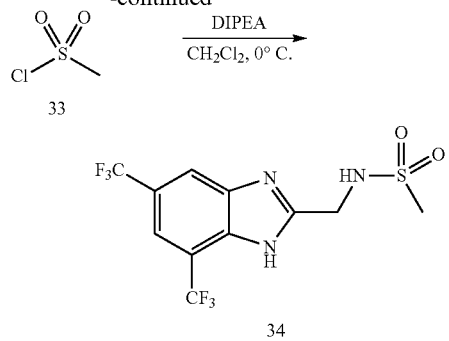

Preparation of N-((5,7-bis(trifluoromethyl)-1H-benzo[d]imidazol-2-yl)methyl) methanesulfonamide (34)

To a solution of (5,7-bis(trifluoromethyl)-1H-benzo[d]imidazol-2-yl)methanamine hydrogen chloride (5) (0.30 g, 0.94 mmol) and DIPEA (0.3 mL, 2 mmol) in dichloromethane (25 mL) at 0° C. was added methanesulfonyl chloride (33) (0.07 mL, 0.94 mmol) dropwise via syringe. The resultant solution was warmed to room temperature, stirred for 72 hours, and then concentrated in vacuo. The resultant oil was then taken up in dichloromethane (30 mL) and washed with a saturated aqueous solution of sodium bicarbonate (20 mL) and brine (20 mL). The organic layer was dried over anhydrous sodium sulfate and concentrated in vacuo. The crude product was purified by automated flash chromatography (ethyl acetate) to afford the title compound (34) (confirmed by LCMS (positive ion mode).

Example 11

Synthesis of (R)-2-(pyrrolidin-2-yl)-4,6-bis(trifluoromethyl)-1H-benzo[d]imidazole (39)

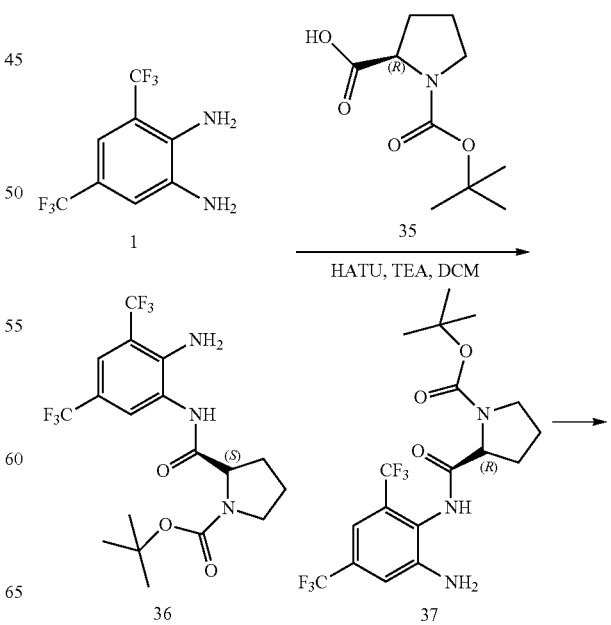

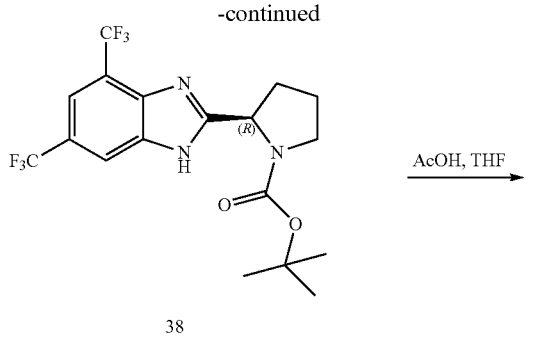

Example 12

Synthesis of 2-(3-((4,6-bis(trifluoromethyl)-1H-benzo[d]imidazol-2-yl)methyl)azetidin-1-yl)-N-(1-methylcyclobutyl)acetamide (42)

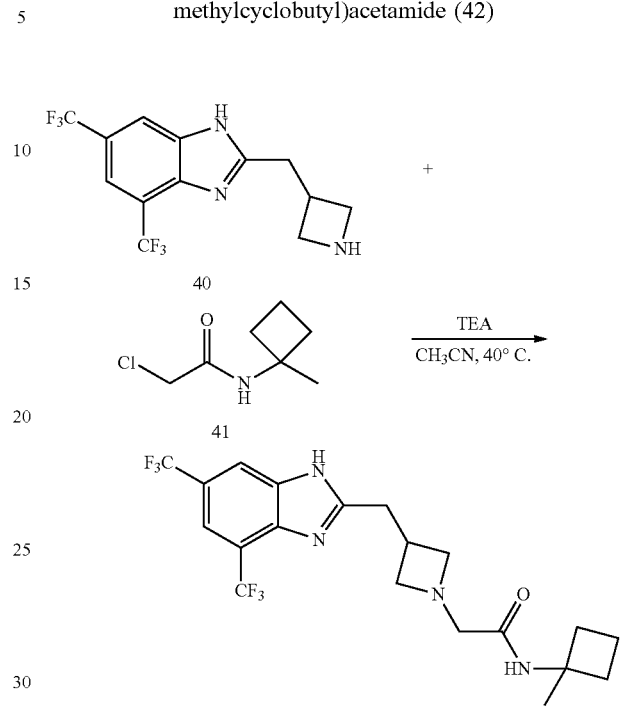

Preparation of (R)-2-(pyrrolidin-2-yl)-4,6-bis(trifluoromethyl)-1H-benzo[d]imidazole (39)

3,5-bis(trifluoromethyl)benzene-1,2-diamine (1) (1.5 g, 6.14 mmol), (R)-1-(tert-butoxycarbonyl)pyrrolidine-2-carboxylic acid (35) (1.30 g, 6.04 mmol), TEA (1.1 mL, 7.98 mmol), and HATU (3.2 g, 8.42 mmol) were dissolved in DCM (15 mL). This solution was stirred overnight at room temperature and then concentrated in vacuo. The residue was taken up in ethyl acetate (50 mL) and then washed sequentially with saturated aqueous ammonium chloride (20 mL), saturated sodium bicarbonate (20 mL), and brine (20 mL). The organic fraction was then dried over anhydrous sodium sulfate, filtered, and concentrated in vacuo. The residue was purified by automated column chromatography (smooth gradient 20→70% ethyl acetate:petroleum ether) to afford a mixture of the desired isomers (36) and (37), confirmed by LCMS (positive ion mode).

The mixture of isomers was taken up in THF/AcOH (95/5) and heated using a microwave at 140° C. for 2 hours. The reaction was concentrated in vacuo, taken up in EtOAc, and then washed with water (30 mL), saturated aqueous sodium bicarbonate (30 mL), and brine (30 mL). The organic layer was dried over anhydrous sodium sulfate then concentrated in vacuo. The residue was purified by automated column chromatography (smooth gradient 20→70% ethyl acetate:petroleum ether), and this initial purification was followed by a second round of automated column chromatography (smooth gradient 0→50% ethyl acetate:dichloromethane) to afford the N-Boc-protected product (38) as clear colorless gum. The product was taken up in HCl saturated ethyl acetate and stirred for two hours at room temperature. The clear mixture turned milky over time and was condensed in vacuo to give the HCl salt of the product (39) as a white solid (1.00 g, 51% over two steps). $^1$H NMR (300 MHz, CD$_3$OD) δ 2.24-2.40 (m, 3H), 2.67-2.75 (m, 1H), 3.52-3.59 (m, 1H), 3.63-3.70 (m, 1H), 5.17 (t, J=6 Hz, 1H), 7.86 (s, 1H), 8.25 (s, 1H).

Preparation of 2-(3-((4,6-bis(trifluoromethyl)-1H-benzo[d]imidazol-2-yl)methyl)azetidin-1-yl)-N-(1-methylcyclobutyl)acetamide (42)

To a solution of 2-(azetidin-3-ylmethyl)-4,6-bis(trifluoromethyl)-1H-benzo[d]imidazole (40) (0.81 g, 2.5 mmol) and triethylamine (1.8 mL, 13 mmol) in acetonitrile (50 mL) was added 2-chloro-N-(1-methylcyclobutyl)acetamide (41) (0.41 g, 2.5 mmol). The resultant solution was stirred at 40° C. for 17 hours and concentrated in vacuo. The crude product was purified by automated flash chromatography to afford the title compound (42). The product was confirmed by LCMS (positive ion mode).

Example 13

Synthesis of 1-((5,7-bis(trifluoromethyl)-1H-benzo[d]imidazol-2-yl)methyl)piperazin-2-one hydrochloride (47)

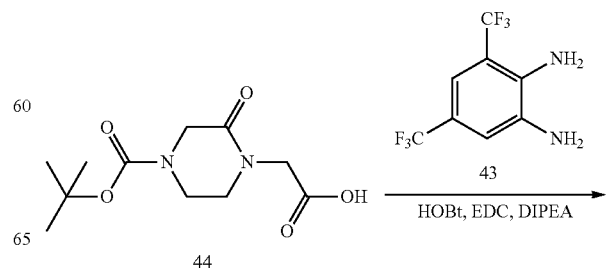

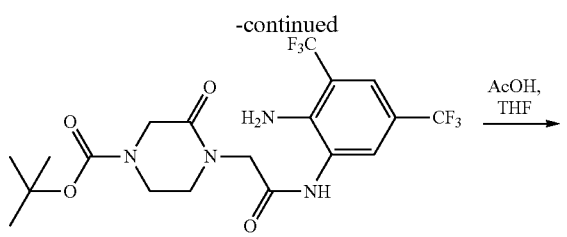

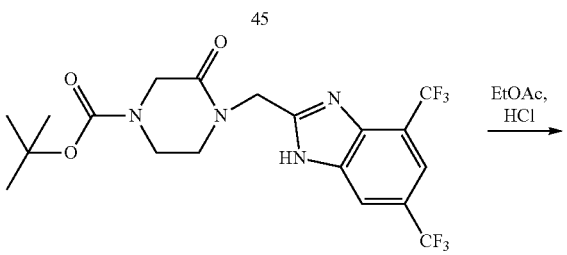

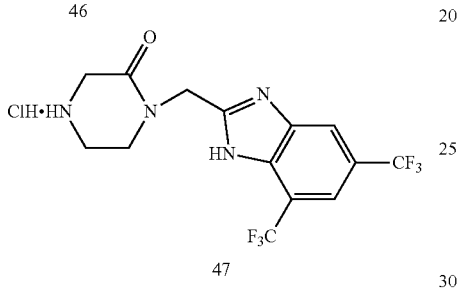

Synthesis of tert-butyl 4-(2-((2-amino-3,5-bis(trifluoromethyl)phenyl)amino)-2-oxoethyl)-3-oxopiperazine-1-carboxylate (45)

2-(4-(tert-butoxycarbonyl)-2-oxopiperazin-1-yl)acetic acid (2) (2.0 g, 7.77 mmol), 3,5 bis(trifluoromethyl)-O-phenylenediamine (44) (2.15 g, 8.81 mmol), HOBt (1.36 g, 10.1 mmol), EDC (1.93 g, 10.1 mmol), and diisopropylethylamine (2.3 mL, 13.2 mmol) were stirred in DMF (15 mL) at room temperature for 14 hours. The residue was concentrated in vacuo and was taken up in EtOAc (200 ml). The reaction mixture was washed sequentially with NH₄Cl (saturated solution), NaHCO₃ (saturated solution), and brine. The organics were separated, dried (Na₂SO₄) and concentrated in vacuo. The residue was purified by automated column chromatography (EtOAc/PE) to give tert-butyl 4-(2-((2-amino-3,5-bis(trifluoromethyl)phenyl)amino)-2-oxoethyl)-3-oxopiperazine-1-carboxylate (45) (3.5 g, 93%; confirmed by LCMS (positive ion mode)).

Synthesis of tert-butyl 4-((4,6-bis(trifluoromethyl)-1H-benzo[d]imidazol-2-yl)methyl)-3-oxopiperazine-1-carboxylate (46)

tert-Butyl 4-(2-((2-amino-3,5-bis(trifluoromethyl)phenyl)amino)-2-oxoethyl)-3-oxopiperazine-1-carboxylate (45) (3.5 g, 7.23 mmol) was heated in THF/AcOH (1:1, 20 mL) using a microwave at 140° C. for 45 minutes. The residue was concentrated in vacuo, and the residue was then taken up in EtOAc (150 ml). The reaction mixture was washed sequentially with NaHCO₃ (saturated solution) and brine. The organics were separated, dried (Na₂SO₄), and concentrated in vacuo. The residue was purified by automated column chromatography (EtOAc) to give tert-butyl 4-((4,6-bis(trifluoromethyl)-1H-benzo[d]imidazol-2-yl)methyl)-3-oxopiperazine-1-carboxylate (46) (3.1 g, 92%; confirmed by LCMS (positive ion mode))

Synthesis of 1-((5,7-bis(trifluoromethyl)-1H-benzo[d]imidazol-2-yl)methyl)piperazin-2-one hydrochloride (47)

tert-butyl 4-((4,6-bis(trifluoromethyl)-1H-benzo[d]imidazol-2-yl)methyl)-3-oxopiperazine-1-carboxylate (46) (3.1 g, 6.65 mmol) was taken up in EtOAc, and the solution was flushed with HCl (g) for 5 minutes. The resultant suspension was stirred at room temperature for 30 minutes then concentrated in vacuo. The resultant solid was dried under high vacuum for 14 hours to give 1-((5,7-bis(trifluoromethyl)-1H-benzo[d]imidazol-2-yl)methyl)piperazin-2-one hydrochloride (47) in a quantitative manner. ¹H NMR (300 mHz, CD₃OD) δ 3.70-3.75 (m, 2H), 4.00-4.10 (m, 4H), 5.10 (s, 1H), 8.15 (s, 1H), 8.2 (s, 1H), 7.86 (s, 1H).

Example 14

Synthesis of 2-(azetidin-3-ylmethyl)-4,6-bis(trifluoromethyl)-1H-benzo[d]imidazole (51)

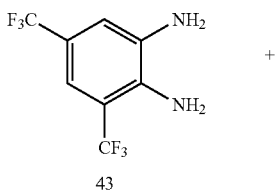

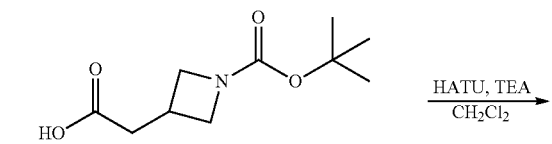

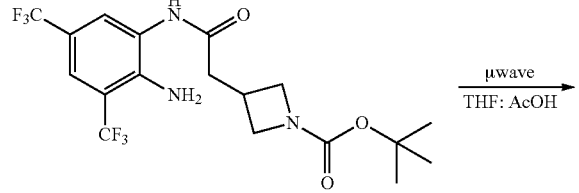

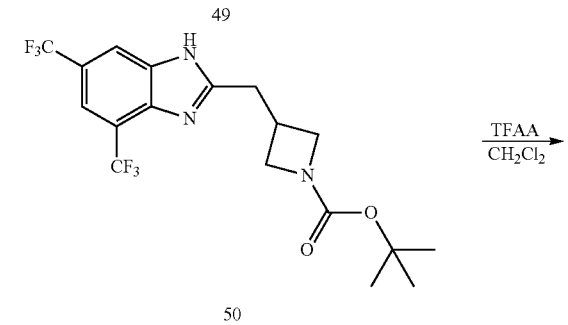

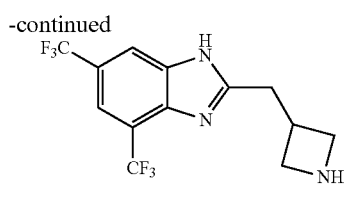

51

Preparation of tert-butyl 3-(2-((2-amino-3,5-bis(trifluoromethyl)phenyl)amino)-2-oxoethyl)azetidine-1-carboxylate (49)

To a mixture of 3,5-bis(trifluoromethyl)benzene-1,2-diamine (43) (3.00 g, 12.3 mmol), 2-(1-(tert-butoxycarbonyl)azetidin-3-yl)acetic acid (48) (2.64 g, 12.3 mmol), and HATU (6.08 g, 16.0 mmol) in dichloromethane (60 mL) was added triethylamine (5.1 mL, 36.9 mmol). The resultant solution was stirred at room temperature for 23 hours and then washed with a saturated aqueous solution of sodium bicarbonate (2×70 mL). The organic phase was then dried over anhydrous sodium sulfate and concentrated in vacuo. The crude product was purified by automated flash chromatography (1:1 hexane:ethyl acetate) to afford the title compound (49) (3.46 g, 64%) as a white foam. The other regioisomer was not observed during the course of purification. The product was confirmed by LCMS (positive ion mode).

Preparation of tert-butyl 3-((4,6-bis(trifluoromethyl)-1H-benzo[d]imidazol-2-yl)methyl)azetidine-1-carboxylate (50)

To a solution of tert-butyl 3-(2-((2-amino-3,5-bis(trifluoromethyl)phenyl)amino)-2-oxoethyl)azetidine-1-carboxylate (49) (2.54 g, 5.75 mmol) in tetrahydrofuran (15 mL) was added glacial acetic acid (3 mL). The reaction was sealed in a microwave reaction vial and reacted at 130° C. for 45 minutes. The resultant solution was concentrated in vacuo, taken up in ethyl acetate (80 mL), and washed with a saturated aqueous solution of sodium bicarbonate (20 mL). The organic phase was then dried over anhydrous sodium sulfate and concentrated in vacuo. The crude product was purified by automated flash chromatography (1:1 hexane:ethyl acetate) to afford the title compound (50) (2.12 g, 87%) as a white solid. The product was confirmed by LCMS (positive ion mode).

Preparation of 2-(azetidin-3-ylmethyl)-4,6-bis(trifluoromethyl)-1H-benzo[d]imidazole (51)

To a solution of tert-butyl 3-((4,6-bis(trifluoromethyl)-1H-benzo[d]imidazol-2-yl)methyl)azetidine-1-carboxylate (50) (1.06 g, 2.50 mmol) in dichloromethane (40 mL) was added trifluoroacetic acid (2.4 mL, 31 mmol). The resultant solution was allowed to stir at room temperature for 2.5 hours and was then concentrated in vacuo. The resultant oil was taken up in toluene (30 mL) then concentrated in vacuo. The crude product was purified by automated flash chromatography (80:20:1 dichloromethane:methanol: ammonium hydroxide) to afford the title compound (51) as a cream colored foam; $^1$H NMR (400 MHz, CD$_3$OD) δ 3.22 (quintet, 1H), 3.28 (d, 2H), 3.47 (septet, 1H), 3.99 (m, 2H), 4.16 (m, 2H), 7.64 (s, 1H), 8.00 (s, 1H). The product was confirmed by LCMS (positive ion mode).

Example 15

Synthesis of 2-(2-oxopiperazin-1-yl)-N-(5-(trifluoromethyl)pyridin-2-yl)acetamide (54)

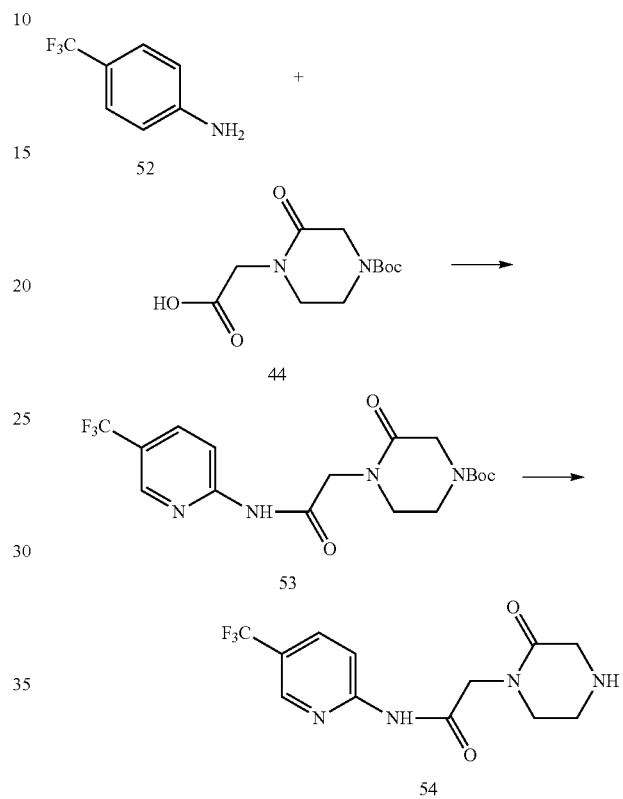

Synthesis of tert-butyl 3-oxo-4-(2-oxo-2-((5-(trifluoromethyl)pyridin-2-yl)amino)ethyl)piperazine-1-carboxylate (53)

To a solution of 5-(trifluoromethyl)pyridin-2-amine (52) (0.162 g, 1 mmol), 2-(4-(tert-butoxycarbonyl)-2-oxopiperazin-1-yl)acetic acid (44) (0.257 g, 1 mmol), and HATU (0.46 g, 1.3 mmol) in DMF 3 ml was added triethylamine (0.3 ml, 3 mmol). The mixture was heated in a microwave at 75° C. for 2 hours. The reaction mixture was diluted with ethyl acetate and washed with saturated sodium bicarbonate aqueous solution and brine. The organic layer was dried over sodium sulfate and concentrated. The residue was purified by automated flash chromatography using pet ether and ethyl acetate as eluents. Yield 0.15 g, 50%. LCMS m/z 401.9 (M+H$^+$).

Synthesis of 2-(2-oxopiperazin-1-yl)-N-(5-(trifluoromethyl)pyridin-2-yl)acetamide (54)

To a solution of tert-butyl 3-oxo-4-(2-oxo-2-((5-(trifluoromethyl)pyridin-2-yl)amino)ethyl)piperazine-1-carboxylate (53) (0.15 g, 0.5 mmol) in ethyl acetate (3 ml) was added saturated HCl solution in ethyl acetate (2 ml). The reaction mixture was stirred at room temperature for 30 minutes. The reaction mixture was then concentrated and dried in vacuo to give 2-(2-oxopiperazin-1-yl)-N-(5-(trifluoromethyl)pyridin-2-yl)acetamide (54) as HCl salt. Yield 0.165 g, 98%. LCMS m/z 301.9 (M+H$^+$).

Example 16

Synthesis of 1-(2-(4,6-bis(trifluoromethyl)-1H-benzo[d]imidazol-2-yl)ethyl)piperazin-2-one (61)

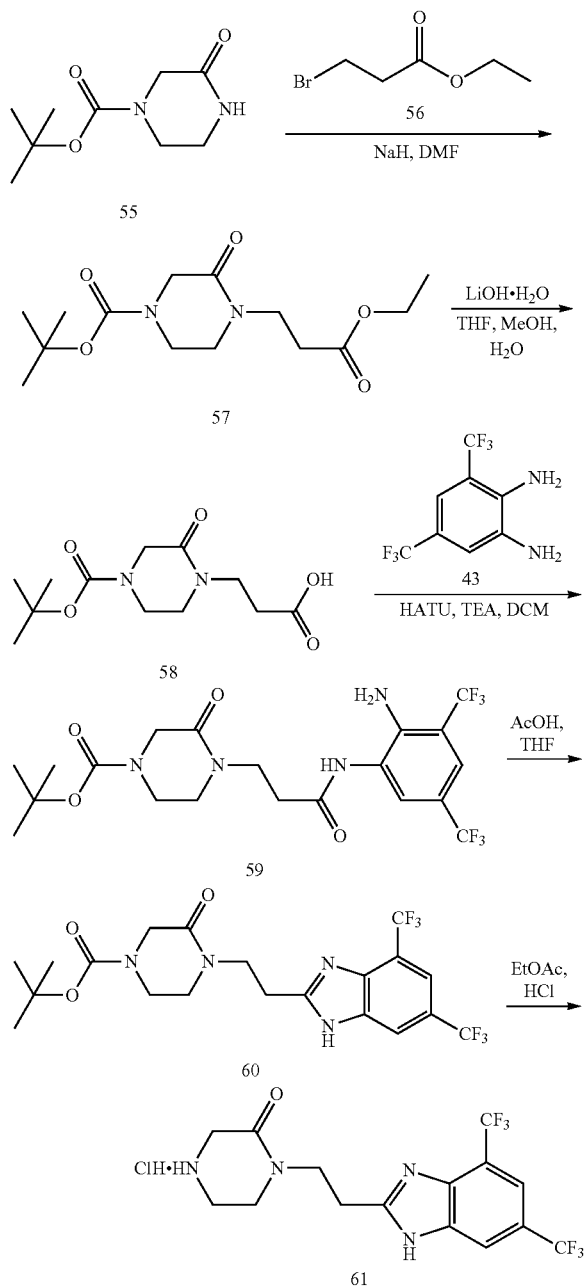

Synthesis of tert-butyl 4-(3-ethoxy-3-oxopropyl)-3-oxopiperazine-1-carboxylate (57)

tert-Butyl 3-oxopiperazine-1-carboxylate (55) (4.0 g, 20 mmol) was stirred in dry DMF at room temperature under Ar. NaH (60% dispersion in mineral oil) (960 mg, 24 mmol) was added, and the reaction stirred for 30 minutes. Ethyl bromopropionate (56) (2.55 mL, 20 mmol) was added in one portion, and stirring continued for 14 hours. The reaction was partitioned between EtOAc and H$_2$O. The organics were separated, dried (Na$_2$SO$_4$), and concentrated in vacuo to give tert-butyl 4-(3-ethoxy-3-oxopropyl)-3-oxopiperazine-1-carboxylate (57) as a crude residue, which was used in the subsequent reaction without additional purification. The product was confirmed with LCMS (positive ion mode).

Synthesis of 3-(4-(tert-butoxycarbonyl)-2-oxopiperazin-1-yl)propanoic acid (58)

tert-Butyl 4-(3-ethoxy-3-oxopropyl)-3-oxopiperazine-1-carboxylate (57); as the crude residue from the previous step) and H$_2$O (1.26 g, 30 mmol) were stirred in THF/H$_2$O/MeOH (40/40/15 mL) at room temperature for 16 hours. The resultant solution was filtered to remove solid precipitation. The organic solvent was removed in vacuo, and the solution was acidified with 1M HCl. The reaction was extracted with EtOAc (3×75 mL), and the organics were dried (Na$_2$SO$_4$) and concentrated in vacuo to give 3-(4-(tert-butoxycarbonyl)-2-oxopiperazin-1-yl)propanoic acid (58) (4.4 g, 81% from tert-Butyl 3-oxopiperazine-1-carboxylate (55). The product was confirmed by LCMS (negative ion mode).

Synthesis of tert-butyl 4-(3-((2-amino-3,5-bis(trifluoromethyl)phenyl)amino)-3-oxopropyl)-3-oxopiperazine-1-carboxylate (59)

3-(4-(tert-Butoxycarbonyl)-2-oxopiperazin-1-yl)propanoic acid (58) (1.52 g, 5.6 mmol), 3,5 bis(trifluoromethyl)-O-phenylenediamine (1) (1.36 g, 5.6 mmol), HATU (2.91 g, 7.84 mmol) and TEA (1.56 mL, 11.8 mmol) were stirred in DCM (50 mL) at room temperature for 14 hours. The reaction was diluted with DCM (100 mL), washed sequentially with NH$_4$Cl (saturated solution), NaHCO$_3$ (saturated solution) and brine, the organics separated, dried (Na$_2$SO$_4$), and concentrated in vacuo. The residue was purified by automated column chromatography (100% EtOAc/PE) to give tert-butyl 4-(3-((2-amino-3,5-bis(trifluoromethyl)phenyl)amino)-3-oxopropyl)-3-oxopiperazine-1-carboxylate (59) (2.64 g, 95%; confirmed by LCMS (positive ion mode)).

Synthesis of 1-(2-(4,6-bis(trifluoromethyl)-1H-benzo[d]imidazol-2-yl)ethyl)piperazin-2-one hydrochloride (61)

tert-Butyl 4-(3-((2-amino-3,5-bis(trifluoromethyl)phenyl)amino)-3-oxopropyl)-3-oxopiperazine-1-carboxylate (59) (500 mg, 1.0 mmol) was heated in THF/AcOH (95:5, 2 mL) using a microwave at 140° C. for 2.5 hours. The residue was concentrated in vacuo to give crude tert-butyl 4-(2-(4,6-bis(trifluoromethyl)-1H-benzo[d]imidazol-2-yl)ethyl)-3-oxopiperazine-1-carboxylate (60). The crude material was taken up in EtOAc, and the solution flushed with HCl (g) for 5 minutes. The suspension was stirred at room temperature for 20 minutes and concentrated in vacuo. The residue was purified by reverse phase HPLC to give 1-(2-(4,6-bis(trifluoromethyl)-1H-benzo[d]imidazol-2-yl)ethyl)piperazin-2-one hydrochloride (61).

Example 17

Synthesis of 2-(4,6-bis(trifluoromethyl)-1H-benzo[d]imidazol-2-yl)-1-(piperazin-1-yl)ethanone (68)

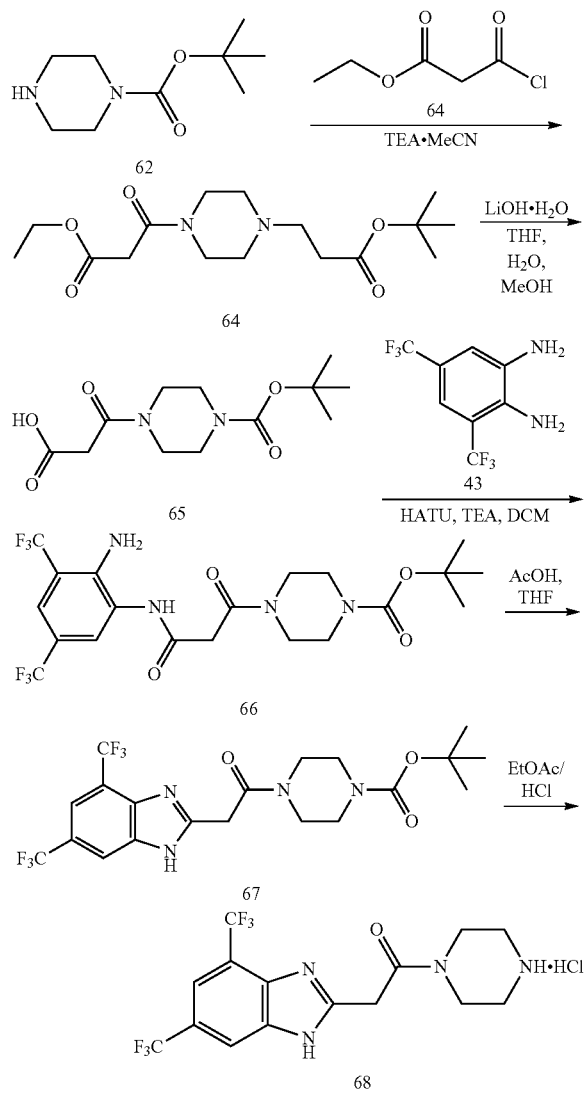

Synthesis of tert-butyl 4-(3-ethoxy-3-oxopropanoyl)piperazine-1-carboxylate (64)

tert-Butyl piperazine-1-carboxylate (62) (1 g, 5.4 mmol) and TEA (837 μL, 6.0 mmol) were stirred in DCM at room temperature. Ethyl malonyl chloride (63) (810 μL, 5.4 mmol) was added in one portion, and the reaction stirred at room temperature for 1 hour. The reaction was diluted with DCM and washed sequentially with NH₄Cl (saturated solution) and NaHCO₃ (saturated solution). The organics were separated, dried (Na₂SO₄), and concentrated in vacuo. The residue was purified by automated column chromatography (100% EtOAc) to give tert-butyl 4-(3-ethoxy-3-oxopropanoyl)piperazine-1-carboxylate (64) (1.24 g, 77%). The product was confirmed by LCMS (positive ion mode).

Synthesis of 3-(4-(tert-butoxycarbonyl)piperazin-1-yl)-3-oxopropanoic acid (65)

tert-Butyl 4-(3-ethoxy-3-oxopropanoyl)piperazine-1-carboxylate (64) (1.24 g, 2.8 mmol) and LiOH.H₂O (176 mg, 4.2 mmol) was stirred in THF/H₂O/MeOH (30/30/10 mL) at room temperature for 14 hours. The organic solvents were removed in vacuo, and the solution was acidified with 1 M HCl and extracted with EtOAc. The organics were separated, dried (Na₂SO₄), and concentrated in vacuo to give 3-(4-(tert-butoxycarbonyl)piperazin-1-yl)-3-oxopropanoic acid (65) in a quantitative fashion. The product was confirmed by LCMS (negative ion mode) and was used in the subsequent reaction without additional purification

Synthesis of tert-butyl 4-(3-((2-amino-3, 5-bis(trifluoromethyl)phenyl)amino)-3-oxopropanoyl)piperazine-1-carboxylate (66)

3-(4-(tert-Butoxycarbonyl)piperazin-1-yl)-3-oxopropanoic acid (65) (761 mg, 2.8 mmol), 3,5-bis(trifluoromethyl)benzene-1,2-diamine (43) (744 m g, 3.05 mmol), HATU (1.6 g, 4.27 mmol), and TEA (906 μL, 6.5 mmol) were stirred in DCM at room temperature for 14 hours. The precipitate was removed by filtration. The filtrate was diluted with DCM and washed sequentially with NH₄Cl (saturated solution) and NaHCO₃ (saturated solution). The organics were separated, dried (Na₂SO₄), and concentrated in vacuo. The residue was purified by automated column chromatography (EtOAc/PE, 50/50) to give tert-butyl 4-(3-((2-amino-3,5-bis(trifluoromethyl)phenyl)amino)-3-oxopropanoyl)piperazine-1-carboxylate (66) (650 mg, 42%). The product was confirmed by LCMS (positive ion mode).

Synthesis of 2-(4,6-bis(trifluoromethyl)-1H-benzo[d]imidazol-2-yl)-1-(piperazin-1-yl)ethanone hydrochloride (68)

tert-Butyl 4-(3-((2-amino-3,5-bis(trifluoromethyl)phenyl)amino)-3-oxopropanoyl)piperazine-1-carboxylate (66) (650 mg, 1.31 mmol) was heated in THF/AcOH (95:5, 2 mL) using a microwave at 140° C. for 2.5 hours. The residue was concentrated in vacuo to give crude tert-butyl 4-(2-(4,6-bis(trifluoromethyl)-1H-benzo[d]imidazol-2-yl)acetyl)piperazine-1-carboxylate (67). The crude was taken up in EtOAc, and the solution was flushed with HCl (g) for 5 minutes. The suspension was stirred at room temperature for 20 minutes and concentrated in vacuo. The residue was purified by reverse phase HPLC to give 2-(4,6-bis(trifluoromethyl)-1H-benzo[d]imidazol-2-yl)-1-(piperazin-1-yl)ethanone hydrochloride (68).

Example 18

Synthesis of 1-((1-(2-hydroxy-2-methylpropyl)-4,6-bis(trifluoromethyl)-1H-benzo[d]imidazol-2-yl)methyl)piperazin-2-one (30)

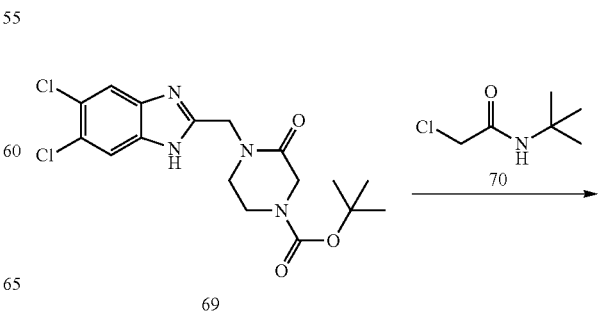

54

Example 19

Synthesis of 1-((4,6-dichloro-1-(2-hydroxy-2-methylpropyl)-1H-benzo[d]imidazol-2-yl)methyl)piperazin-2-one (33)

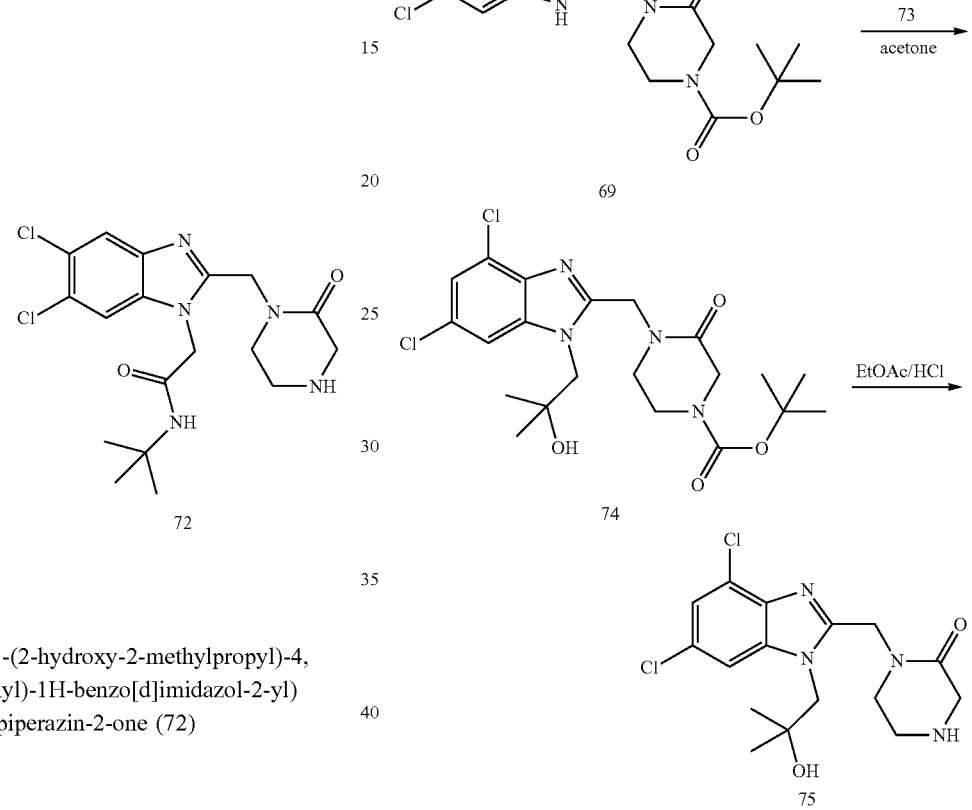

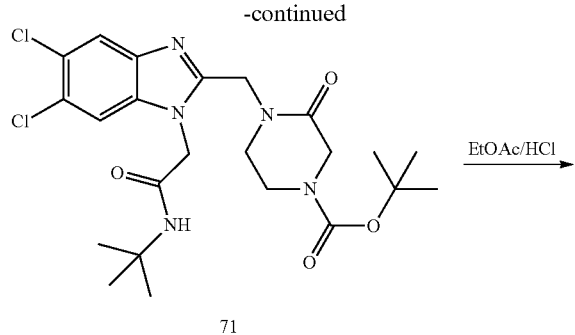

Preparation of 1-((1-(2-hydroxy-2-methylpropyl)-4,6-bis(trifluoromethyl)-1H-benzo[d]imidazol-2-yl)methyl)piperazin-2-one (72)

tert-Butyl-4-((5,6-dichloro-1H-benzo[d]imidazol-2-yl)methyl)-3-oxopiperazine-1-carboxylate (69) (0.50 g, 1.25 mmol) and N-(tert-butyl)-2-chloroacetamide (70) (0.20 g, 1.3 mmol) were dissolved in acetone (10 mL). The resultant solution was stirred at reflux for 48 hours, cooled to room temperature, and poured into water (60 mL). The aqueous mixture was extracted with ethyl acetate (3×50 mL). The combined organic fractions were dried with anhydrous sodium sulfate, filtered, then condensed in vacuo to give the Boc-protected product (71) (0.60 g, 93%), which was confirmed by LCMS (positive ion mode). A portion of this material (100 mg, 0.20 mmol) was taken up into ethyl acetate (20 mL). HCl gas was bubbled through this solution for one minute. The reaction was then stirred at room temperature for 30 minutes and concentrated in vacuo. The resulting residue was purified by automated flash chromatography to afford the desired free amine (72). The product was confirmed by LCMS (positive ion mode).

Preparation of 1-((4,6-dichloro-1-(2-hydroxy-2-methylpropyl)-1H-benzo[d]imidazol-2-yl)methyl)piperazin-2-one (75)

tert-Butyl-4-((4,6-dichloro-1H-benzo[d]imidazol-2-yl)methyl)-3-oxopiperazine-1-carboxylate (300 mg, 0.75 mmol) (69), 2,2-dimethyloxirane (73) (0.67 mL, 542 mg, 7.5 mmol), and potassium carbonate (1.04 g, 7.5 mmol) were taken up in acetone (5 mL). The reaction was heated at 110° C. by microwave irradiation for 1 hour. The solution was concentrated in vacuo, and the residue containing the Boc-protected product (74) was taken up in ethyl acetate. HCl gas was bubbled through this solution for 1 minute. The solution was then stirred for 30 minutes at room temperature and concentrated in vacuo. The resulting residue was purified by automated flash chromatography to afford the desired free amine (75). The product was confirmed by LCMS (positive ion mode).

Following the general procedures as set forth in exemplary synthetic procedures above, the following compounds listed in Table 1 were prepared. Mass spectrometry was employed with final compounds and at various stages throughout the synthesis as a confirmation of the identity of the product obtained (M+1). For the mass spectrometric analysis, samples were prepared at an approximate concentration of 1 μmg/mL in acetonitrile with 0.1% formic acid. Samples were manually infused into an Applies Biosystems API3000 triple quadrupole mass spectrometer and scanned in Q1 in the range of 50 to 700 m/z.

TABLE 1

| No. | Structure | Mol. Wt. | Chemical Name |
|---|---|---|---|
| 1 | 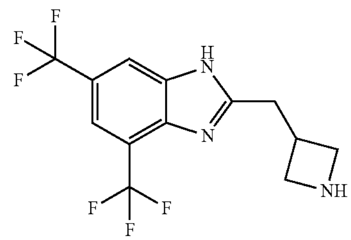 [SMILES: FC(F)(F)c1cc(C(F)(F)F)c2nc(CC3CNC3)[nH]c2c1] | 323.237 | 2-(azetidin-3-ylmethyl)-4,6-bis(trifluoromethyl)-1H-benzo[d]imidazole |
| 2 | 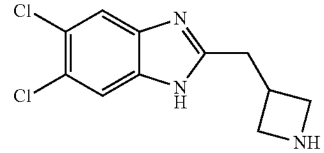 [SMILES: Clc1cc2nc(CC3CNC3)[nH]c2cc1Cl] | 256.131 | 2-(azetidin-3-ylmethyl)-5,6-dichloro-1H-benzo[d]imidazole |
| 3 | 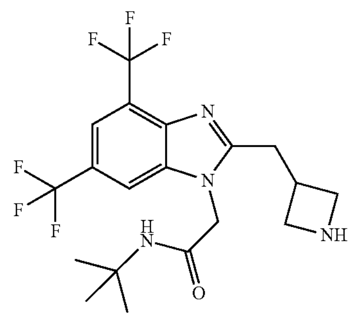 [SMILES: CC(C)(C)NC(=O)Cn1c(CC2CNC2)nc2c(C(F)(F)F)cc(C(F)(F)F)cc21] | 436.395 | 2-(2-(azetidin-3-ylmethyl)-4,6-bis(trifluoromethyl)-1H-benzo[d]imidazol-1-yl)-N-(tert-butyl)acetamide |
| 4 | 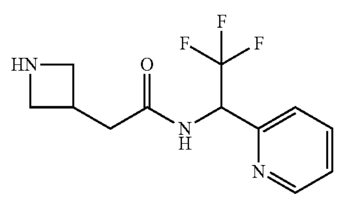 [SMILES: O=C(CC1CNC1)NC(c1ccccn1)C(F)(F)F] | 273.254 | 2-(azetidin-3-yl)-N-(2,2,2-trifluoro-1-(52yridine-2-yl)ethyl)acetamide |
| 5 | 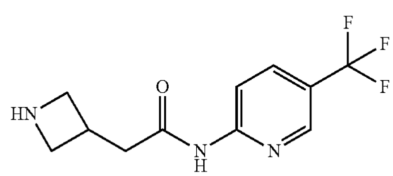 [SMILES: O=C(CC1CNC1)Nc1ccc(C(F)(F)F)cn1] | 259.228 | 2-(azetidin-3-yl)-N-(5-(trifluoromethyl)52yridine-2-yl)acetamide |
| 6 | 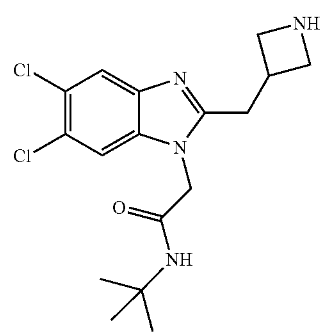 [SMILES: CC(C)(C)NC(=O)Cn1c(CC2CNC2)nc2cc(Cl)c(Cl)cc21] | 369.289 | 2-(2-(azetidin-3-ylmethyl)-5,6-dichloro-1H-benzo[d]imidazol-1-yl)-N-(tert-butyl)acetamide |

TABLE 1-continued

| No. | Structure | Mol. Wt. | Chemical Name |
|---|---|---|---|
| 7 | 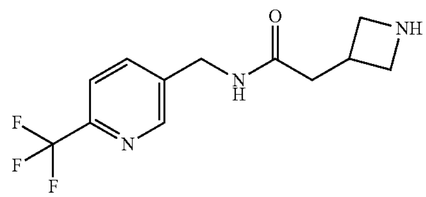 [SMILES: O=C(CC1CNC1)NCc1ccc(C(F)(F)F)nc1] | 273.254 | 2-(azetidin-3-yl)-N-((6-(trifluoromethyl)52yridine-3-yl)methyl)acetamide |
| 8 | 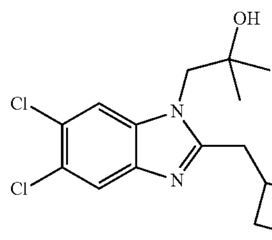 | 328.237 | 1-(2-(azetidin-3-ylmethyl)-5,6-dichloro-1H-benzo[d]imidazol-1-yl)-2-methylpropan-2-ol |
| 9 | 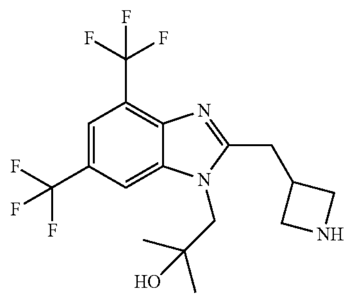 [SMILES: CC(C)(O)Cn1c(CC2CNC2)nc2c(C(F)(F)F)cc(C(F)(F)F)cc21] | 395.343 | 1-(2-(azetidin-3-ylmethyl)-4,6-bis(trifluoromethyl)-1H-benzo[d]imidazol-1-yl)-2-methylpropan-2-ol |
| 10 | 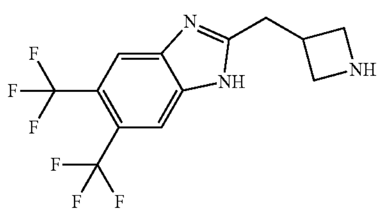 [SMILES: FC(F)(F)c1cc2nc(CC3CNC3)[nH]c2cc1C(F)(F)F] | 323.237 | 2-(azetidin-3-ylmethyl)-5,6-bis(trifluoromethyl)-1H-benzo[d]imidazole |
| 11 | 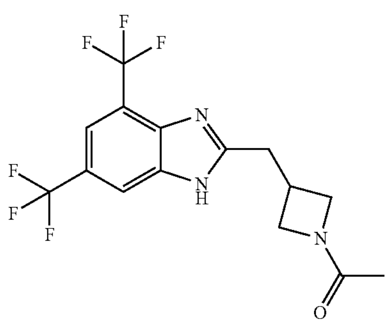 [SMILES: CC(=O)N1CC(Cc2nc3c(C(F)(F)F)cc(C(F)(F)F)cc3[nH]2)C1] | 365.274 | 1-(3-((4,6-bis(trifluoromethyl)-1H-benzo[d]imidazol-2-yl)methyl)azetidin-1-yl)ethanone |
| 12 | 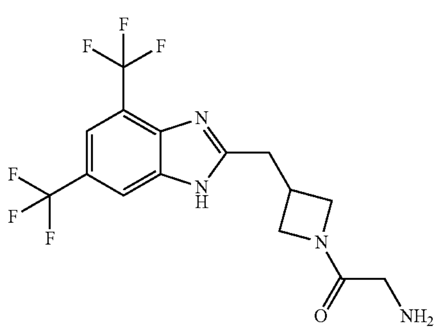 [SMILES: NCC(=O)N1CC(Cc2nc3c(C(F)(F)F)cc(C(F)(F)F)cc3[nH]2)C1] | 380.288 | 2-amino-1-(3-((4,6-bis(trifluoromethyl)-1H-benzo[d]imidazol-2-yl)methyl)azetidin-1-yl)ethanone |

TABLE 1-continued

| No. | Structure | Mol. Wt. | Chemical Name |
|---|---|---|---|
| 13 | 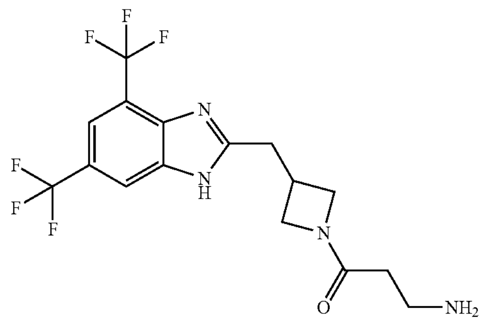 [SMILES: NCCC(=O)N1CC(Cc2nc3c(C(F)(F)F)cc(C(F)(F)F)cc3[nH]2)C1] | 394.315 | 3-amino-1-(3-((4,6-bis(trifluoromethyl)-1H-benzo[d]imidazol-2-yl)methyl)azetidin-1-yl)propan-1-one |
| 14 | 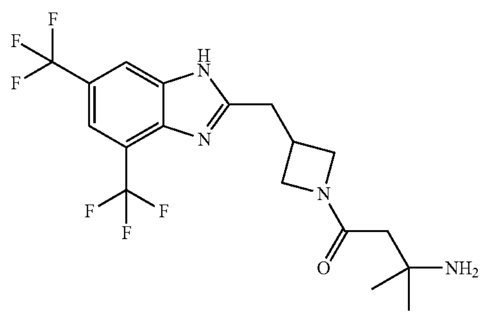 [SMILES: CC(C)(N)CC(=O)N1CC(Cc2nc3c(C(F)(F)F)cc(C(F)(F)F)cc3[nH]2)C1] | 422.368 | 3-amino-1-(3-((4,6-bis(trifluoromethyl)-1H-benzo[d]imidazol-2-yl)methyl)azetidin-1-yl)-3-methylbutan-1-one |
| 15 | 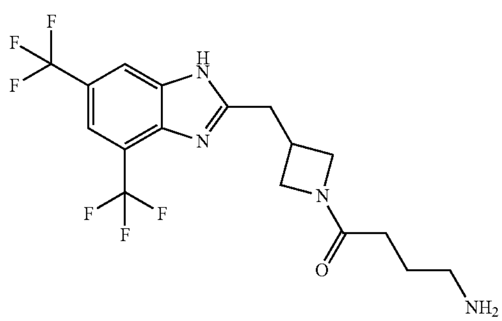 [SMILES: NCCCC(=O)N1CC(Cc2nc3c(C(F)(F)F)cc(C(F)(F)F)cc3[nH]2)C1] | 408.341 | 4-amino-1-(3-((4,6-bis(trifluoromethyl)-1H-benzo[d]imidazol-2-yl)methyl)azetidin-1-yl)butan-1-one |
| 16 | 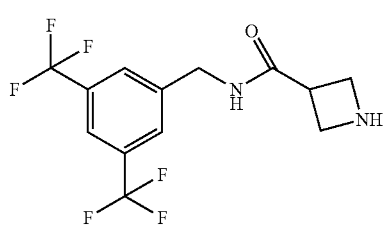 [SMILES: O=C(NCc1cc(C(F)(F)F)cc(C(F)(F)F)c1)C1CNC1] | 326.238 | N-(3,5-bis(trifluoromethyl)benzyl)azetidine-3-carboxamide |
| 17 | 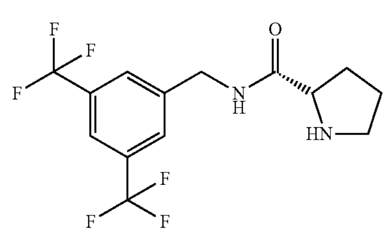 | 340.264 | (S)-N-(3,5-bis(trifluoromethyl)benzyl)pyrrolidine-2-carboxamide |

TABLE 1-continued

| No. | Structure | Mol. Wt. | Chemical Name |
|---|---|---|---|
| 18 | 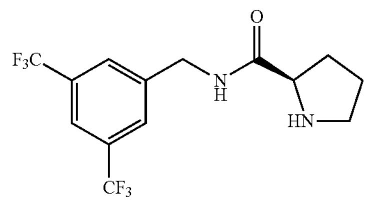 [SMILES: O=C(NCc1cc(C(F)(F)F)cc(C(F)(F)F)c1)[C@H]1CCCN1] | 340.264 | ®-N-(3,5-bis(trifluoromethyl)benzyl)pyrrolidine-2-carboxamide |
| 19 | 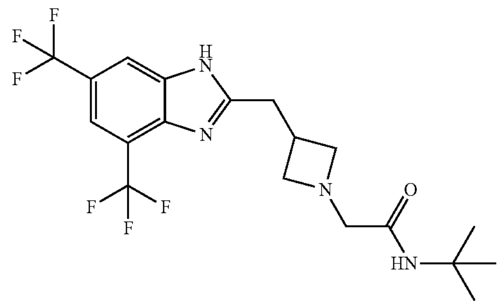 [SMILES: CC(C)(C)NC(=O)CN1CC(Cc2nc3c(C(F)(F)F)cc(C(F)(F)F)cc3[nH]2)C1] | 436.395 | 2-(3-((4,6-bis(trifluoromethyl)-1H-benzo[d]imidazol-2-yl)methyl)azetidin-1-yl)-N-(tert-butyl)acetamide |
| 20 | 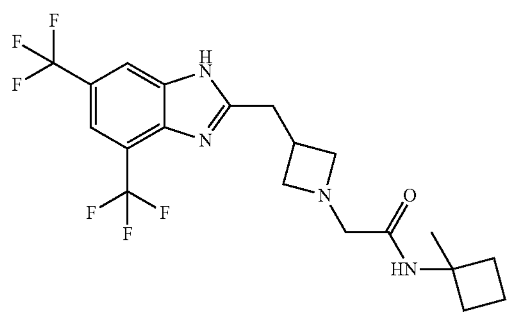 [SMILES: CC1(NC(=O)CN2CC(Cc3nc4c(C(F)(F)F)cc(C(F)(F)F)cc4[nH]3)C2)CCC1] | 448.405 | 2-(3-((4,6-bis(trifluoromethyl)-1H-benzo[d]imidazol-2-yl)methyl)azetidin-1-yl)-N-(1-methylcyclobutyl)acetamide |
| 21 | 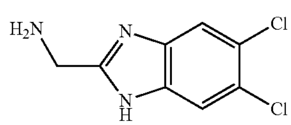 [SMILES: NCc1nc2cc(Cl)c(Cl)cc2[nH]1] | 216.067 | (5,6-dichloro-1H-benzo[d]imidazol-2-yl)methanamine |
| 22 | 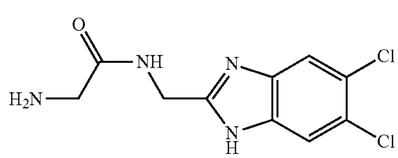 [SMILES: NCC(=O)NCc1nc2cc(Cl)c(Cl)cc2[nH]1] | 273.119 | 2-amino-N-((5,6-dichloro-1H-benzo[d]imidazol-2-yl)methyl)acetamide |
| 23 | 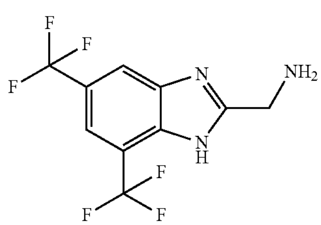 [SMILES: NCc1nc2cc(C(F)(F)F)cc(C(F)(F)F)c2[nH]1] | 283.173 | (5,7-bis(trifluoromethyl)-1H-benzo[d]imidazol-2-yl)methanamine |
| 24 | 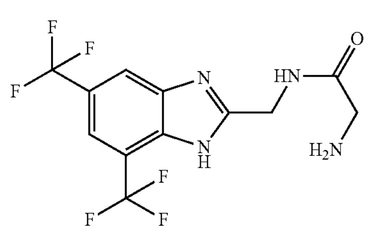 [SMILES: NCC(=O)NCc1nc2cc(C(F)(F)F)cc(C(F)(F)F)c2[nH]1] | 340.224 | 2-amino-N-((5,7-bis(trifluoromethyl)-1H-benzo[d]imidazol-2-yl)methyl)acetamide |

TABLE 1-continued

| No. | Structure | Mol. Wt. | Chemical Name |
|---|---|---|---|
| 25 | 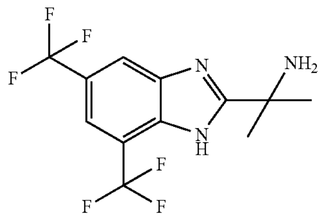 [SMILES: CC(C)(N)c1nc2cc(C(F)(F)F)cc(C(F)(F)F)c2[nH]1] | 311.226 | 2-(5,7-bis(trifluoromethyl)-1H-benzo[d]imidazol-2-yl)propan-2-amine |
| 26 | 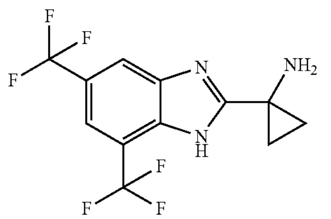 [SMILES: NC1(c2nc3cc(C(F)(F)F)cc(C(F)(F)F)c3[nH]2)CC1] | 309.21 | 1-(5,7-bis(trifluoromethyl)-1H-benzo[d]imidazol-2-yl)cyclopropanamine |
| 27 | 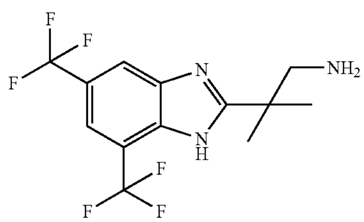 [SMILES: CC(C)(CN)c1nc2cc(C(F)(F)F)cc(C(F)(F)F)c2[nH]1] | 325.253 | 2-(5,7-bis(trifluoromethyl)-1H-benzo[d]imidazol-2-yl)-2-methylpropan-1-amine |
| 28 | 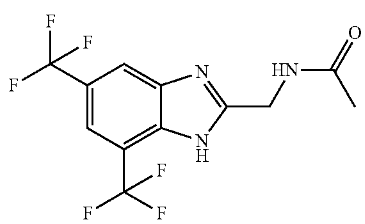 [SMILES: CC(=O)NCc1nc2cc(C(F)(F)F)cc(C(F)(F)F)c2[nH]1] | 325.21 | N-((5,7-bis(trifluoromethyl)-1H-benzo[d]imidazol-2-yl)methyl)acetamide |
| 29 | 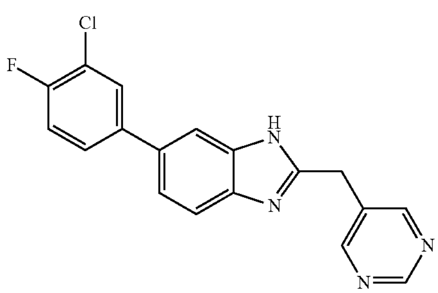 [SMILES: Fc1ccc(-c2ccc3nc(Cc4cncnc4)[nH]c3c2)cc1Cl] | 338.766 | 6-(3-chloro-4-fluorophenyl)-2-(pyrimidin-5-ylmethyl)-1H-benzo[d]imidazole |
| 30 | 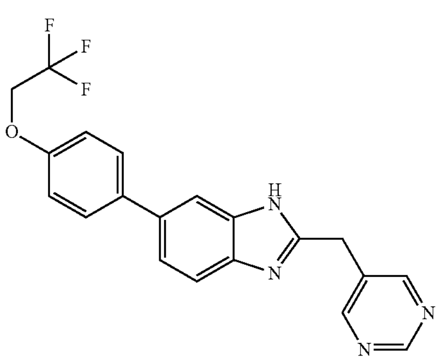 [SMILES: FC(F)(F)COc1ccc(-c2ccc3nc(Cc4cncnc4)[nH]c3c2)cc1] | 384.355 | 2-(pyrimidin-5-ylmethyl)-6-(4-(2,2,2-trifluoroethoxy)phenyl)-1H-benzo[d]imidazole |

TABLE 1-continued

| No. | Structure | Mol. Wt. | Chemical Name |
|---|---|---|---|
| 31 | 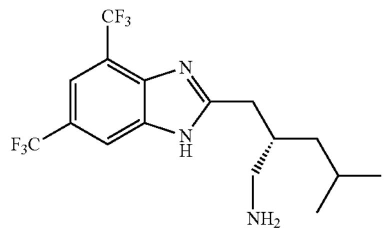 [SMILES: CC(C)C[C@H](CN)Cc1nc2c(C(F)(F)F)cc(C(F)(F)F)cc2[nH]1] | 367.333 | (S)-2-((4,6-bis(trifluoromethyl)-1H-benzo[d]imidazol-2-yl)methyl)-4-methylpentan-1-amine |
| 32 | 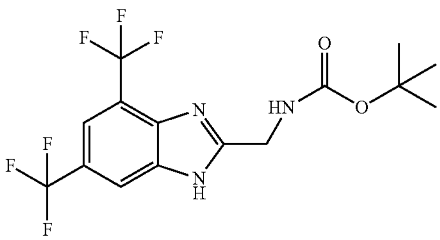 [SMILES: CC(C)(C)OC(=O)NCc1nc2c(C(F)(F)F)cc(C(F)(F)F)cc2[nH]1] | 383.289 | tert-butyl ((4,6-bis(trifluoromethyl)-1H-benzo[d]imidazol-2-yl)methyl)carbamate |
| 33 | 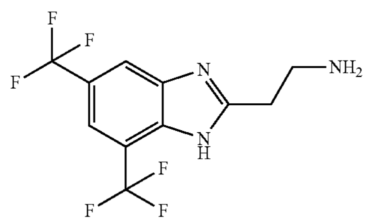 [SMILES: NCCc1nc2cc(C(F)(F)F)cc(C(F)(F)F)c2[nH]1] | 297.2 | 2-(5,7-bis(trifluoromethyl)-1H-benzo[d]imidazol-2-yl)ethanamine |
| 34 | 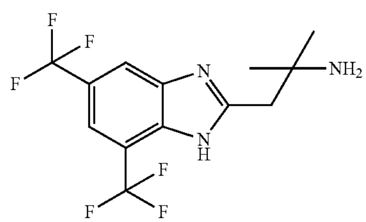 [SMILES: CC(C)(N)Cc1nc2cc(C(F)(F)F)cc(C(F)(F)F)c2[nH]1] | 325.253 | 1-(5,7-bis(trifluoromethyl)-1H-benzo[d]imidazol-2-yl)-2-methylpropan-2-amine |
| 35 | 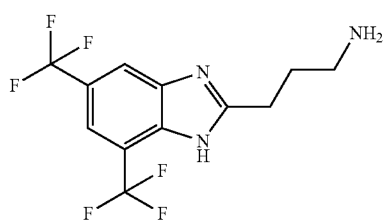 [SMILES: NCCCc1nc2cc(C(F)(F)F)cc(C(F)(F)F)c2[nH]1] | 311.226 | 3-(5,7-bis(trifluoromethyl)-1H-benzo[d]imidazol-2-yl)propan-1-amine |
| 36 | 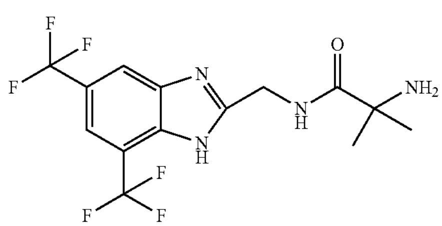 [SMILES: CC(C)(N)C(=O)NCc1nc2cc(C(F)(F)F)cc(C(F)(F)F)c2[nH]1] | 368.278 | 2-amino-N-((5,7-bis(trifluoromethyl)-1H-benzo[d]imidazol-2-yl)methyl)-2-methylpropanamide |
| 37 | 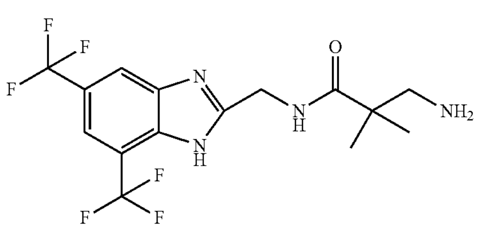 [SMILES: CC(C)(CN)C(=O)NCc1nc2cc(C(F)(F)F)cc(C(F)(F)F)c2[nH]1] | 382.304 | 3-amino-N-((5,7-bis(trifluoromethyl)-1H-benzo[d]imidazol-2-yl)methyl)-2,2-dimethylpropanamide |

TABLE 1-continued

| No. | Structure | Mol. Wt. | Chemical Name |
|---|---|---|---|
| 38 | 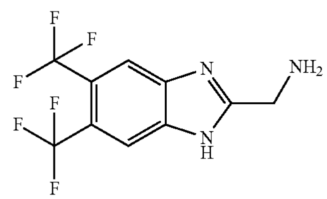 [SMILES: NCc1nc2cc(C(F)(F)F)c(C(F)(F)F)cc2[nH]1] | 283.173 | (5,6-bis(trifluoromethyl)-1H-benzo[d]imidazol-2-yl)methanamine |
| 39 | 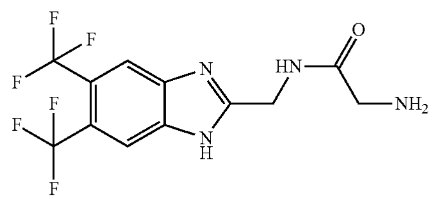 [SMILES: NCC(=O)NCc1nc2cc(C(F)(F)F)c(C(F)(F)F)cc2[nH]1] | 340.224 | 2-amino-N-((5,6-bis(trifluoromethyl)-1H-benzo[d]imidazol-2-yl)methyl)acetamide |
| 40 | 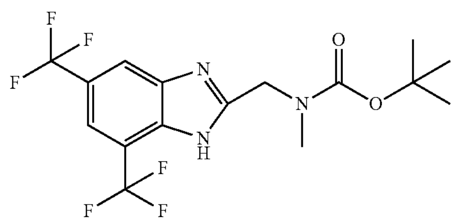 [SMILES: CN(Cc1nc2cc(C(F)(F)F)cc(C(F)(F)F)c2[nH]1)C(=O)OC(C)(C)C] | 397.315 | tert-butyl ((5,7-bis(trifluoromethyl)-1H-benzo[d]imidazol-2-yl)methyl)(methyl)carbamate |
| 41 | 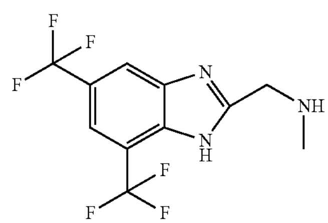 [SMILES: CNCc1nc2cc(C(F)(F)F)cc(C(F)(F)F)c2[nH]1] | 297.2 | 1-(5,7-bis(trifluoromethyl)-1H-benzo[d]imidazol-2-yl)-N-methylmethanamine |
| 42 | 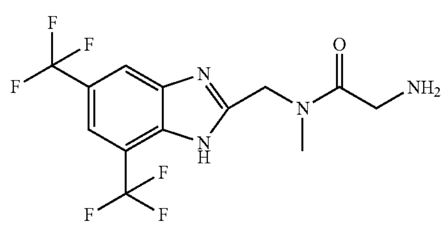 [SMILES: CN(Cc1nc2cc(C(F)(F)F)cc(C(F)(F)F)c2[nH]1)C(=O)CN] | 354.251 | 2-amino-N-((5,7-bis(trifluoromethyl)-1H-benzo[d]imidazol-2-yl)methyl)-N-methylacetamide |
| 43 | 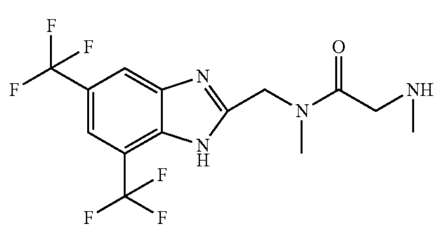 [SMILES: CNCC(=O)N(C)Cc1nc2cc(C(F)(F)F)cc(C(F)(F)F)c2[nH]1] | 368.278 | N-((5,7-bis(trifluoromethyl)-1H-benzo[d]imidazol-2-yl)methyl)-N-methyl-2-(methylamino)acetamide |
| 44 | 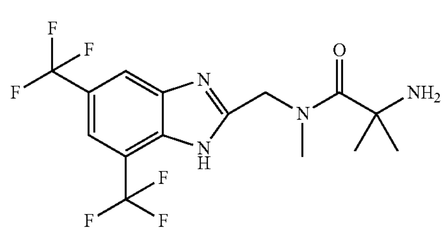 [SMILES: CN(Cc1nc2cc(C(F)(F)F)cc(C(F)(F)F)c2[nH]1)C(=O)C(C)(C)N] | 382.304 | 2-amino-N-((5,7-bis(trifluoromethyl)-1H-benzo[d]imidazol-2-yl)methyl)-N,2-dimethylpropanamide |

TABLE 1-continued

| No. | Structure | Mol. Wt. | Chemical Name |
|---|---|---|---|
| 45 | 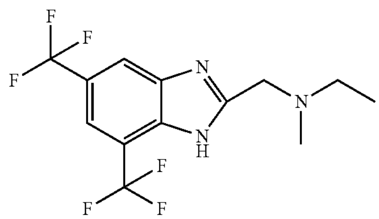 [SMILES: CCN(C)Cc1nc2cc(C(F)(F)F)cc(C(F)(F)F)c2[nH]1] | 325.253 | N-((5,7-bis(trifluoromethyl)-1H-benzo[d]imidazol-2-yl)methyl)-N-methylethanamine |
| 46 | 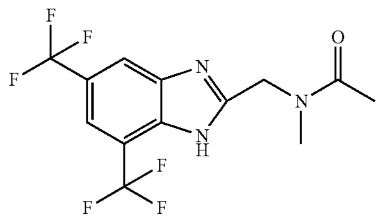 [SMILES: CC(=O)N(C)Cc1nc2cc(C(F)(F)F)cc(C(F)(F)F)c2[nH]1] | 339.236 | N-((5,7-bis(trifluoromethyl)-1H-benzo[d]imidazol-2-yl)methyl)-N-methylacetamide |
| 47 | 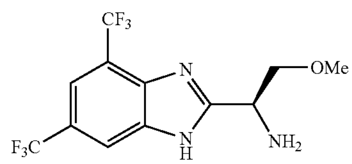 [SMILES: COC[C@@H](N)c1nc2c(C(F)(F)F)cc(C(F)(F)F)cc2[nH]1] | 327.226 | (S)-1-(4,6-bis(trifluoromethyl)-1H-benzo[d]imidazol-2-yl)-2-methoxyethanamine |
| 48 | 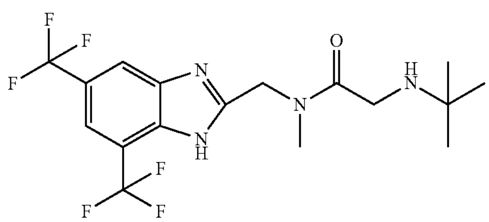 [SMILES: CN(Cc1nc2cc(C(F)(F)F)cc(C(F)(F)F)c2[nH]1)C(=O)CNC(C)(C)C] | 410.357 | N-((5,7-bis(trifluoromethyl)-1H-benzo[d]imidazol-2-yl)methyl)-2-(tert-butylamino)-N-methylacetamide |
| 49 | 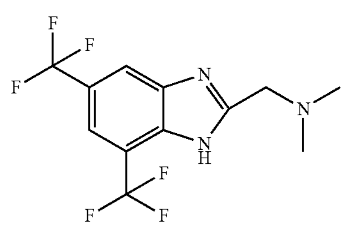 [SMILES: CN(C)Cc1nc2cc(C(F)(F)F)cc(C(F)(F)F)c2[nH]1] | 311.226 | 1-(5,7-bis(trifluoromethyl)-1H-benzo[d]imidazol-2-yl)-N,N-dimethylmethanamine |
| 50 | 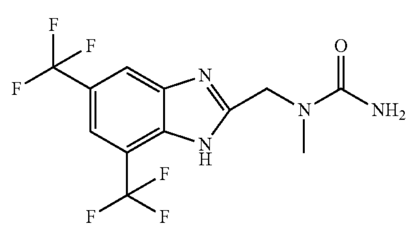 [SMILES: CN(Cc1nc2cc(C(F)(F)F)cc(C(F)(F)F)c2[nH]1)C(N)=O] | 340.224 | 1-((5,7-bis(trifluoromethyl)-1H-benzo[d]imidazol-2-yl)methyl)-1-methylurea |
| 51 | 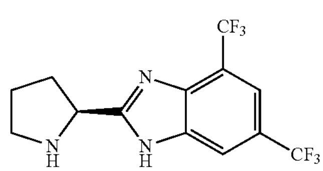 [SMILES: FC(F)(F)c1cc(C(F)(F)F)c2nc([C@@H]3CCCN3)[nH]c2c1] | 323.237 | (S)-2-(pyrrolidin-2-yl)-4,6-bis(trifluoromethyl)-1H-benzo[d]imidazole |
| 52 | 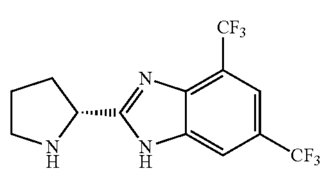 [SMILES: FC(F)(F)c1cc(C(F)(F)F)c2nc([C@H]3CCCN3)[nH]c2c1] | 323.237 | (R)-2-(pyrrolidin-2-yl)-4,6-bis(trifluoromethyl)-1H-benzo[d]imidazole |

TABLE 1-continued

| No. | Structure | Mol. Wt. | Chemical Name |
|---|---|---|---|
| 53 | 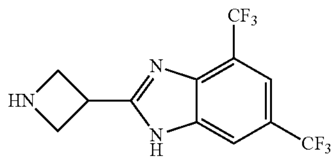 [SMILES: FC(F)(F)c1cc(C(F)(F)F)c2nc(C3CNC3)[nH]c2c1] | 309.21 | 2-(azetidin-3-yl)-4,6-bis(trifluoromethyl)-1H-benzo[d]imidazole |
| 54 | 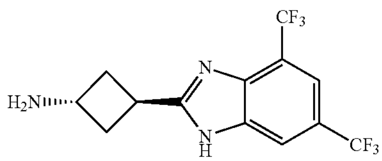 [SMILES: N[C@H]1C[C@H](c2nc3c(C(F)(F)F)cc(C(F)(F)F)cc3[nH]2)C1] | 323.237 | (1r,3r)-3-(4,6-bis(trifluoromethyl)-1H-benzo[d]imidazol-2-yl)cyclobutanamine |
| 55 | 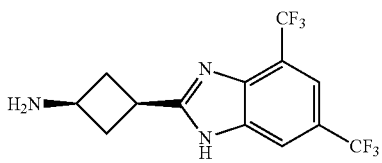 [SMILES: N[C@H]1C[C@@H](c2nc3c(C(F)(F)F)cc(C(F)(F)F)cc3[nH]2)C1] | 323.237 | (1s,3s)-3-(4,6-bis(trifluoromethyl)-1H-benzo[d]imidazol-2-yl)cyclobutanamine |
| 56 | 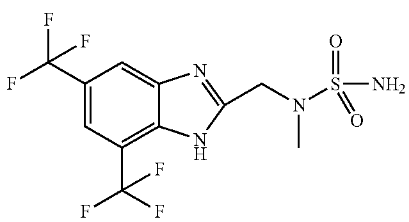 [SMILES: CN(Cc1nc2cc(C(F)(F)F)cc(C(F)(F)F)c2[nH]1)S(N)(=O)=O] | 376.278 | N-{[4,6-bis(trifluoromethyl)-1H-benzimidazol-2-yl]methyl}-N-methylsulfuric diamide |
| 57 | 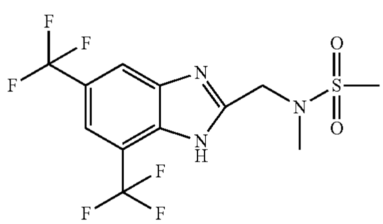 [SMILES: CN(Cc1nc2cc(C(F)(F)F)cc(C(F)(F)F)c2[nH]1)S(C)(=O)=O] | 375.29 | N-((5,7-bis(trifluoromethyl)-1H-benzo[d]imidazol-2-yl)methyl)-N-methylmethanesulfonamide |
| 58 | 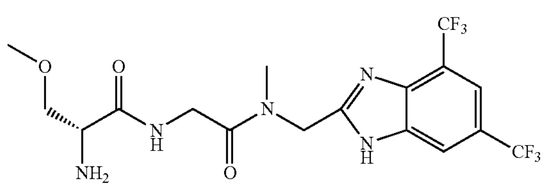 [SMILES: COC[C@@H](N)C(=O)NCC(=O)N(C)Cc1nc2c(C(F)(F)F)cc(C(F)(F)F)cc2[nH]1] | 455.355 | (R)-2-amino-N-(2-(((4,6-bis(trifluoromethyl)-1H-benzo[d]imidazol-2-yl)methyl)(methyl)amino)-2-oxoethyl)-3-methoxypropanamide |
| 59 | 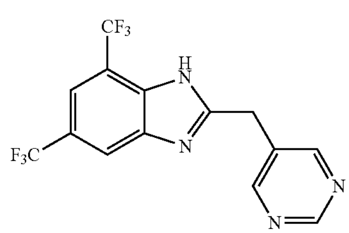 [SMILES: FC(F)(F)c1cc(C(F)(F)F)c2[nH]c(Cc3cncnc3)nc2c1] | 346.231 | 2-(pyrimidin-5-ylmethyl)-5,7-bis(trifluoromethyl)-1H-benzo[d]imidazole |
| 60 | 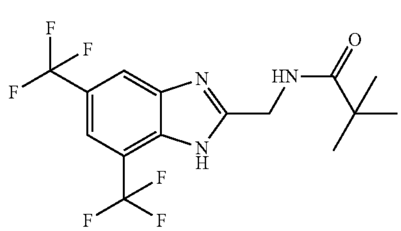 [SMILES: CC(C)(C)C(=O)NCc1nc2cc(C(F)(F)F)cc(C(F)(F)F)c2[nH]1] | 367.29 | N-((5,7-bis(trifluoromethyl)-1H-benzo[d]imidazol-2-yl)methyl)pivalamide |

TABLE 1-continued

| No. | Structure | Mol. Wt. | Chemical Name |
|---|---|---|---|
| 61 | 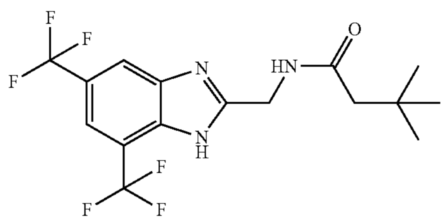 [SMILES: CC(C)(C)CC(=O)NCc1nc2cc(C(F)(F)F)cc(C(F)(F)F)c2[nH]1] | 381.316 | N-((5,7-bis(trifluoromethyl)-1H-benzo[d]imidazol-2-yl)methyl)-3,3-dimethylbutanamide |
| 62 | 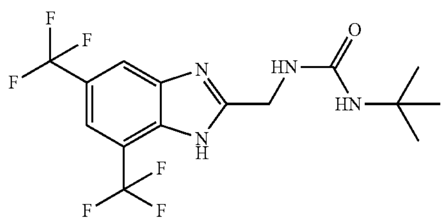 [SMILES: CC(C)(C)NC(=O)NCc1nc2cc(C(F)(F)F)cc(C(F)(F)F)c2[nH]1] | 382.304 | 1-((5,7-bis(trifluoromethyl)-1H-benzo[d]imidazol-2-yl)methyl)-3-(tert-butyl)urea |
| 63 | 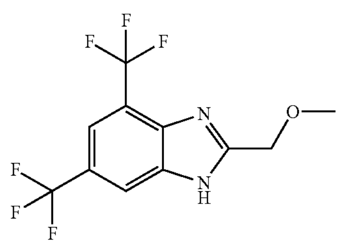 [SMILES: COCc1nc2c(C(F)(F)F)cc(C(F)(F)F)cc2[nH]1] | 298.184 | 2-(methoxymethyl)-4,6-bis(trifluoromethyl)-1H-benzo[d]imidazole |
| 64 | 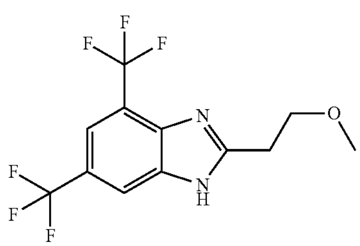 [SMILES: COCCc1nc2c(C(F)(F)F)cc(C(F)(F)F)cc2[nH]1] | 312.211 | 2-(2-metboxyethyl)-4,6-bis(trifluoromethyl)-1H-benzo[d]imidazole |
| 65 | 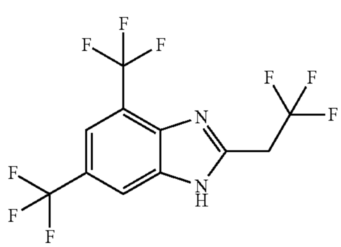 [SMILES: FC(F)(F)Cc1nc2c(C(F)(F)F)cc(C(F)(F)F)cc2[nH]1] | 336.156 | 2-(2,2,2-trifluoroethyl)-4,6-bis(trifluoromethyl)-1H-benzo[d]imidazole |
| 66 | 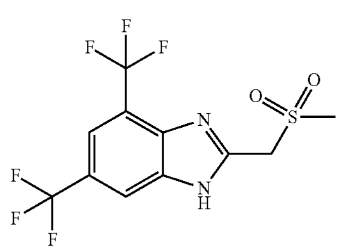 [SMILES: CS(=O)(=O)Cc1nc2c(C(F)(F)F)cc(C(F)(F)F)cc2[nH]1] | 346.249 | 2-((methylsulfonyl)methyl)-4,6-bis(trifluoromethyl)-1H-benzo[d]imidazole |

TABLE 1-continued

| No. | Structure | Mol. Wt. | Chemical Name |
| --- | --- | --- | --- |
| 67 | 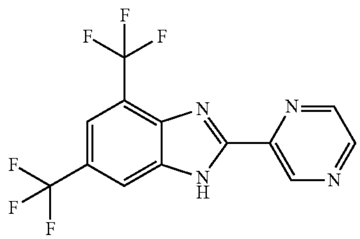 [SMILES: FC(F)(F)c1cc(C(F)(F)F)c2nc(-c3cnccn3)[nH]c2c1] | 332.204 | 2-(pyrazin-2-yl)-4,6-bis(trifluoromethyl)-1H-benzo[d]imidazole |
| 68 | 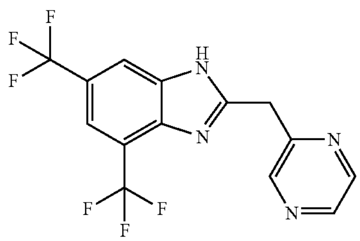 [SMILES: FC(F)(F)c1cc(C(F)(F)F)c2nc(Cc3cnccn3)[nH]c2c1] | 346.231 | 2-(pyrazin-2-ylmethyl)-4,6-bis(trifluoromethyl)-1H-benzo[d]imidazole |
| 69 | 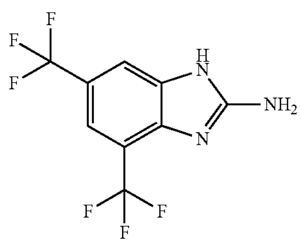 [SMILES: Nc1nc2c(C(F)(F)F)cc(C(F)(F)F)cc2[nH]1] | 269.147 | 4,6-bis(trifluoromethyl)-1H-benzo[d]imidazol-2-amine |
| 70 | 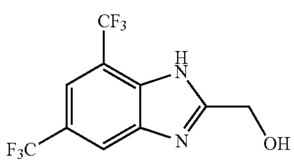 | 284.158 | (5,7-bis(trifluoromethyl)-1H-benzo[d]imidazol-2-yl)methanol |
| 71 | 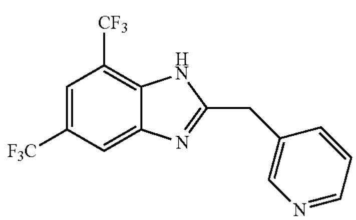 [SMILES: FC(F)(F)c1cc(C(F)(F)F)c2[nH]c(Cc3cccnc3)nc2c1] | 345.242 | 2-(pyridin-3-ylmethyl)-5,7-bis(trifluoromethyl)-1H-benzo[d]imidazole |
| 72 | 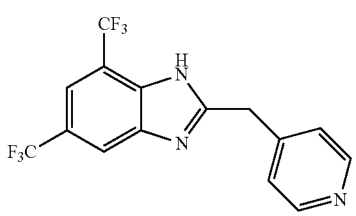 [SMILES: FC(F)(F)c1cc(C(F)(F)F)c2[nH]c(Cc3ccncc3)nc2c1] | 345.242 | 2-(pyridin-4-ylmethyl)-5,7-bis(trifluoromethyl)-1H-benzo[d]imidazole |
| 73 | 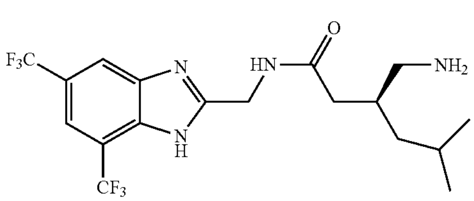 [SMILES: CC(C)C[C@H](CN)CC(=O)NCc1nc2cc(C(F)(F)F)cc(C(F)(F)F)c2[nH]1] | 424.384 | (S)-3-(aminomethyl)-N-((5,7-bis(trifluoromethyl)-1H-benzo[d]imidazol-2-yl)methyl)-5-methylhexanamide |

TABLE 1-continued

| No. | Structure | Mol. Wt. | Chemical Name |
|-----|-----------|----------|---------------|
| 74 | 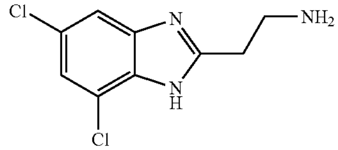 [SMILES: NCCc1nc2cc(Cl)cc(Cl)c2[nH]1] | 230.094 | 2-(5,7-dichloro-1H-benzo[d]imidazol-2-yl)ethanamine |
| 75 | 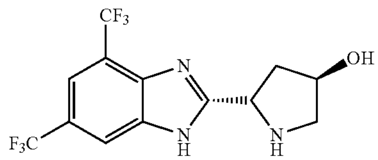 | 339.236 | (3R,5S)-5-(5,7-bis(trifluoromethyl)-1H-benzo[d]imidazol-2-yl)pyrrolidin-3-ol |
| 76 | 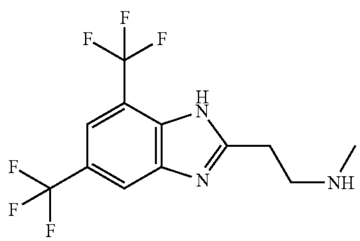 [SMILES: CNCCc1nc2cc(C(F)(F)F)cc(C(F)(F)F)c2[nH]1] | 311.226 | 2-(5,7-bis(trifluoromethyl)-1H-benzo[d]imidazol-2-yl)-N-methylethanamine |
| 77 | 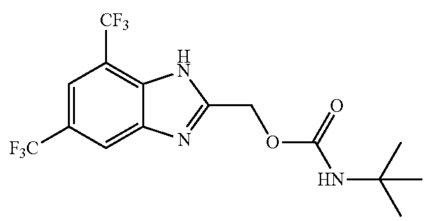 [SMILES: CC(C)(C)NC(=O)OCc1nc2cc(C(F)(F)F)cc(C(F)(F)F)c2[nH]1] | 383.289 | (5,7-bis(trifluoromethyl)-1H-benzo[d]imidazol-2-yl)methyl tert-butylcarbamate |
| 78 | 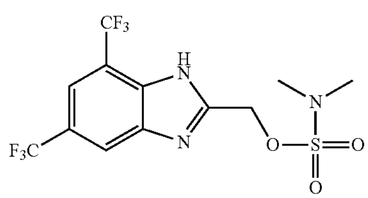 [SMILES: CN(C)S(=O)(=O)OCc1nc2cc(C(F)(F)F)cc(C(F)(F)F)c2[nH]1] | 391.289 | (5,7-bis(trifluoromethyl)-1H-benzo[d]imidazol-2-yl)methyl dimethylsulfamate |
| 79 | 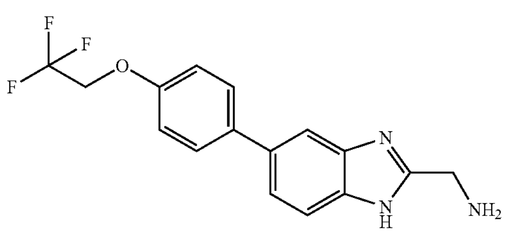 [SMILES: NCc1nc2cc(-c3ccc(OCC(F)(F)F)cc3)ccc2[nH]1] | 321.297 | (5-(4-(2,2,2-trifluoroethoxy)phenyl)-1H-benzo[d]imidazol-2-yl)methanamine |
| 80 | 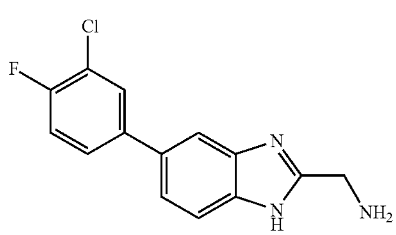 [SMILES: NCc1nc2cc(-c3ccc(F)c(Cl)c3)ccc2[nH]1] | 275.709 | (5-(3-chloro-4-fluorophenyl)-1H-benzo[d]imidazol-2-yl)methanamine |

TABLE 1-continued

| No. | Structure | Mol. Wt. | Chemical Name |
|---|---|---|---|
| 81 | 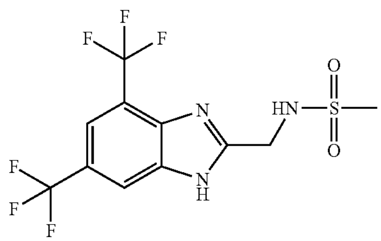 [SMILES: CS(=O)(=O)NCc1nc2c(C(F)(F)F)cc(C(F)(F)F)cc2[nH]1] | 361.263 | N-((4,6-bis(trifluoromethyl)-1H-benzo[d]imidazol-2-yl)methyl)methanesulfonamide |
| 82 | 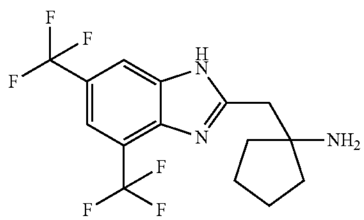 [SMILES: NC1(Cc2nc3c(C(F)(F)F)cc(C(F)(F)F)cc3[nH]2)CCCC1] | 351.29 | 1-((4,6-bis(trifluoromethyl)-1H-benzo[d]imidazol-2-yl)methyl)cyclopentanamine |
| 83 | 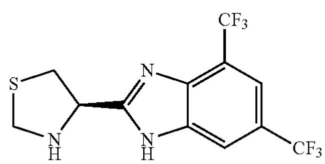 [SMILES: FC(F)(F)c1cc(C(F)(F)F)c2nc([C@@H]3CSCN3)[nH]c2c1] | 341.275 | (R)-4-(4,6-bis(trifluoromethyl)-1H-benzo[d]imidazol-2-yl)thiazolidine |
| 84 | 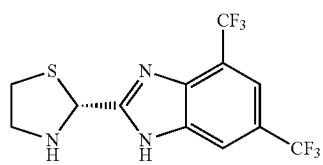 [SMILES: FC(F)(F)c1cc(C(F)(F)F)c2nc([C@@H]3NCCS3)[nH]c2c1] | 341.275 | (R)-2-(4,6-bis(trifluoromethyl)-1H-benzo[d]imidazol-2-yl)thiazolidine |
| 85 | 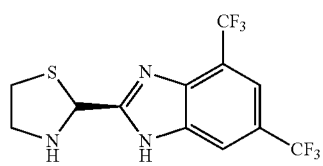 | 341.275 | (S)-2-(4,6-bis(trifluoromethyl)-1H-benzo[d]imidazol-2-yl)thiazolidine |
| 86 | 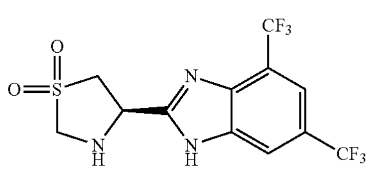 [SMILES: O=S1(=O)CN[C@H](c2nc3c(C(F)(F)F)cc(C(F)(F)F)cc3[nH]2)C1] | 373.274 | (R)-4-(4,6-bis(trifluoromethyl)-1H-benzo[d]imidazol-2-yl)thiazolidine 1,1-dioxide |
| 87 | 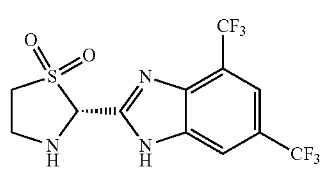 [SMILES: O=S1(=O)CCN[C@H]1c1nc2c(C(F)(F)F)cc(C(F)(F)F)cc2[nH]1] | 373.274 | (R)-2-(4,6-bis(trifluoromethyl)-1H-benzo[d]imidazol-2-yl)thiazolidine 1,1-dioxide |
| 88 | 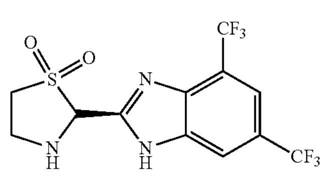 | 373.274 | (S)-2-(4,6-bis(trifluoromethyl)-1H-benzo[d]imidazol-2-yl)thiazolidine 1,1-dioxide |

TABLE 1-continued

| No. | Structure | Mol. Wt. | Chemical Name |
|---|---|---|---|
| 89 | 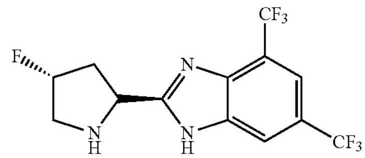 | 341.227 | 2-((2S,4R)-4-fluoropyrrolidin-2-yl)-4,6-bis(trifluoromethyl)-1H-benzo[d]imidazole |
| 90 | 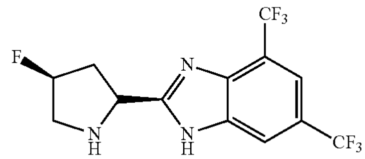 | 341.227 | 2-((2S,4S)-4-fluoropyrrolidin-2-yl)-4,6-bis(trifluoromethyl)-1H-benzo[d]imidazole |
| 91 | 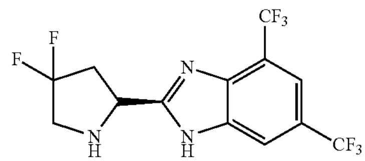 | 359.218 | (S)-2-(4,4-difluoropyrrolidin-2-yl)-4,6-bis(trifluoromethyl)-1H-benzo[d]imidazole |
| 92 | 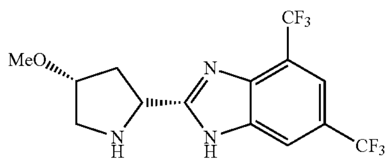 | 353.263 | 2-((2R,4R)-4-methoxypyrrolidin-2-yl)-4,6-bis(trifluoromethyl)-1H-benzo[d]imidazole |
| 93 | 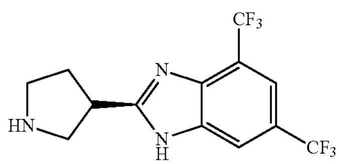 | 323.237 | (R)-2-(pyrrolidin-3-yl)-4,6-bis(trifluoromethyl)-1H-benzo[d]imidazole |
| 94 | 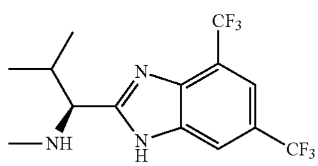 [SMILES: CN[C@H](c1nc2c(C(F)(F)F)cc(C(F)(F)F)cc2[nH]1)C(C)C] | 339.279 | (S)-1-(4,6-bis(trifluoromethyl)-1H-benzo[d]imidazol-2-yl)-N,2-dimethylpropan-1-amine |
| 95 | 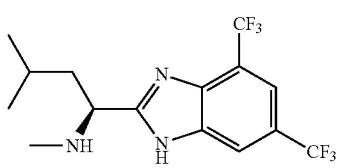 [SMILES: CN[C@@H](CC(C)C)c1nc2c(C(F)(F)F)cc(C(F)(F)F)cc2[nH]1] | 353.306 | (S)-1-(4,6-bis(trifluoromethyl)-1H-benzo[d]imidazol-2-yl)-N,3-dimethylbutan-1-amine |
| 96 | 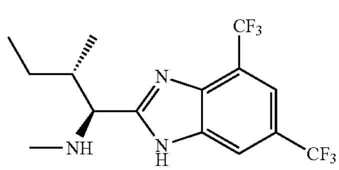 [SMILES: CC[C@H](C)[C@H](NC)c1nc2c(C(F)(F)F)cc(C(F)(F)F)cc2[nH]1] | 353.306 | (1S,2S)-1-(4,6-bis(trifluoromethyl)-1H-benzo[d]imidazol-2-yl)-N,2-dimethylbutan-1-amine |
| 97 | 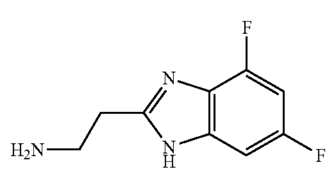 [SMILES: NCCc1nc2c(F)cc(F)cc2[nH]1] | 197.185 | 2-(4,6-difluoro-1H-benzo[d]imidazol-2-yl)ethanamine |

TABLE 1-continued

| No. | Structure | Mol. Wt. | Chemical Name |
|---|---|---|---|
| 98 | 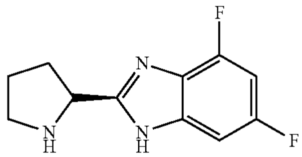 | 223.222 | (S)-4,6-difluoro-2-(pyrrolidin-2-yl)-1H-benzo[d]imidazole |
| 99 | 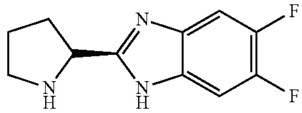 | 223.222 | (S)-5,6-difluoro-2-(pyrrolidin-2-yl)-1H-benzo[d]imidazole |
| 100 | 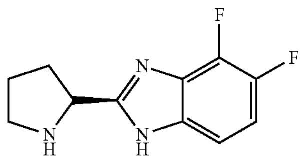 | 223.222 | (S)-4,5-difluoro-2-(pyrrolidin-2-yl)-1H-benzo[d]imidazole |
| 101 | 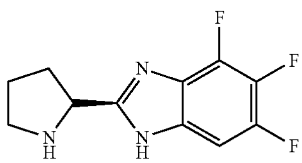 | 241.212 | (S)-4,5,6-trifluoro-2-(pyrrolidin-2-yl)-1H-benzo[d]imidazole |
| 102 | 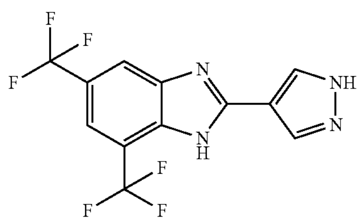 [SMILES: FC(F)(F)c1cc(C(F)(F)F)c2[nH]c(-c3cn[nH]c3)nc2c1] | 320.19 | 2-(1H-pyrazol-4-yl)-5,7-bis(trifluoromethyl)-1H-benzo[d]imidazole |
| 103 | 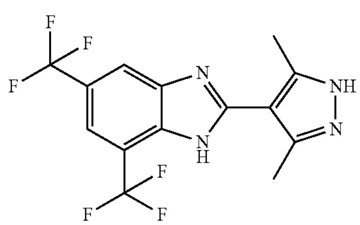 [SMILES: Cc1n[nH]c(C)c1-c1nc2cc(C(F)(F)F)cc(C(F)(F)F)c2[nH]1] | 348.25 | 2-(3,5-(3,5-1H-pyrazol-4-yl)-5,7-bis(trifluoromethyl)-1H-benzo[d]imidazole |
| 104 | 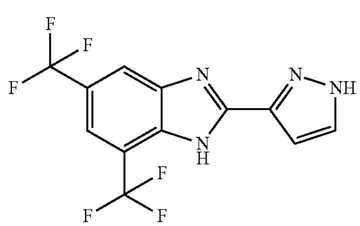 [SMILES: FC(F)(F)c1cc(C(F)(F)F)c2[nH]c(-c3cc[nH]n3)nc2c1] | 320.19 | 2-(1H-pyrazol-3-yl)-5,7-bis(trifluoromethyl)-1H-benzo[d]imidazole |
| 105 | 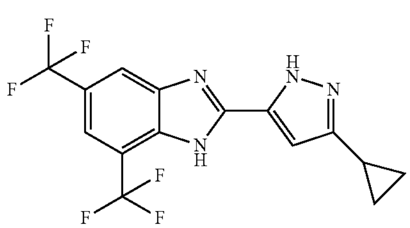 [SMILES: FC(F)(F)c1cc(C(F)(F)F)c2[nH]c(-c3cc(C4CC4)n[nH]3)nc2c1] | 360.26 | 2-(3-cyclopropyl-1H-pyrazol-5-yl)-5,7-bis(trifluoromethyl)-1H-benzo[d]imidazole |

TABLE 1-continued

| No. | Structure | Mol. Wt. | Chemical Name |
|---|---|---|---|
| 106 | 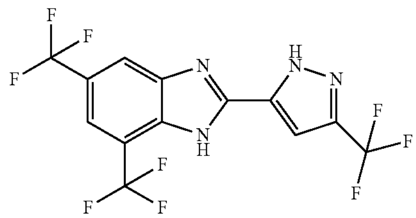 [SMILES: FC(F)(F)c1cc(C(F)(F)F)c2[nH]c(-c3cc(C(F)(F)F)n[nH]3)nc2c1] | 388.19 | 5,7-bis(trifluoromethyl)-2-(3-(trifluoromethyl)-1H-pyrazol-5-yl)-1H-benzo[d]imidazole |
| 107 | 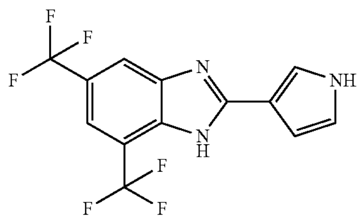 [SMILES: FC(F)(F)c1cc(C(F)(F)F)c2[nH]c(-c3cc[nH]c3)nc2c1] | 319.21 | 2-(1H-pyrrol-3-yl)-5,7-bis(trifluoromethyl)-1H-benzo[d]imidazole |
| 108 | 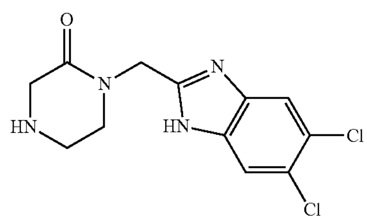 [SMILES: O=C1CNCCN1Cc1nc2cc(Cl)c(Cl)cc2[nH]1] | 299.156 | 1-((5,6-dichloro-1H-benzo[d]imidazol-2-yl)methyl)piperazin-2-one |
| 109 | 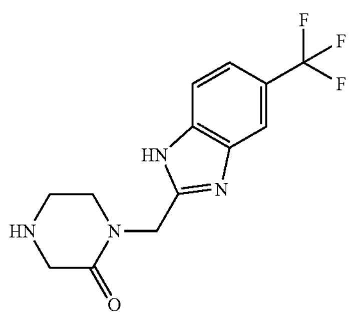 [SMILES: O=C1CNCCN1Cc1nc2cc(C(F)(F)F)ccc2[nH]1] | 298.264 | 1-((5-(trifluoromethyl)-1H-benzo[d]imidazol-2-yl)methyl)piperazin-2-one |
| 110 | 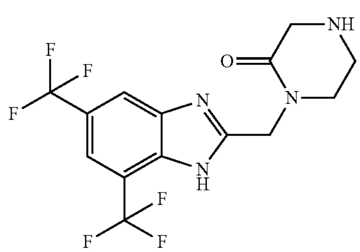 [SMILES: O=C1CNCCN1Cc1nc2cc(C(F)(F)F)cc(C(F)(F)F)c2[nH]1] | 366.262 | 1-((5,7-bis(trifluoromethyl)-1H-benzo[d]imidazol-2-yl)methyl)piperazin-2-one |
| 111 | 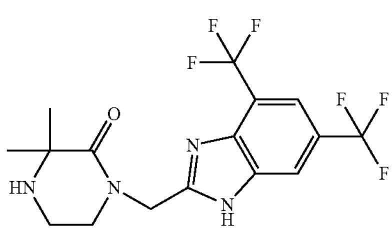 [SMILES: CC1(C)NCCN(Cc2nc3c(C(F)(F)F)cc(C(F)(F)F)cc3[nH]2)C1=O] | 394.315 | 1-((4,6-bis(trifluoromethyl)-1H-benzo[d]imidazol-2-yl)methyl)-3,3-dimethylpiperazin-2-one |

TABLE 1-continued

| No. | Structure | Mol. Wt. | Chemical Name |
|---|---|---|---|
| 112 | 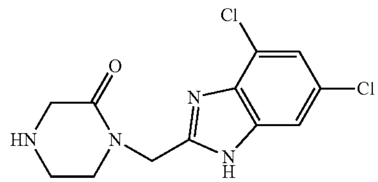 [SMILES: O=C1CNCCN1Cc1nc2c(Cl)cc(Cl)cc2[nH]1] | 299.156 | 1-((4,6-dichloro-1H-benzo[d]imidazol-2-yl)methyl)piperazin-2-one |
| 113 | 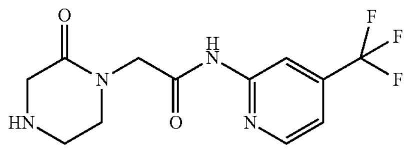 [SMILES: O=C(CN1CCNCC1=O)Nc1cc(C(F)(F)F)ccn1] | 302.252 | 2-(2-oxopiperazin-1-yl)-N-(4-(trifluoromethyl)66yridine-2-yl)acetamide |
| 114 | 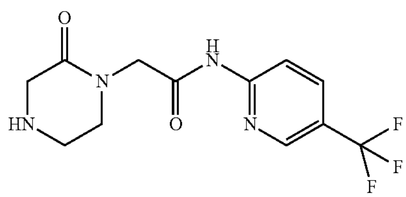 [SMILES: O=C(CN1CCNCC1=O)Nc1ccc(C(F)(F)F)cn1] | 302.252 | 2-(2-oxopiperazin-1-yl)-N-(5-(trifluoromethyl)66yridine-2-yl)acetamide |
| 115 | 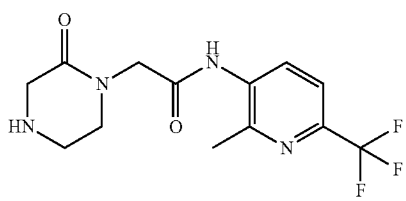 [SMILES: Cc1nc(C(F)(F)F)ccc1NC(=O)CN1CCNCC1=O] | 316.279 | N-(2-methyl-6-(trifluoromethyl)66yridine-3-yl)-2-(2-oxopiperazin-1-yl)acetamide |
| 116 | 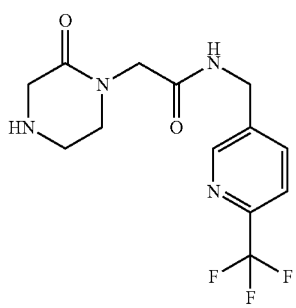 [SMILES: O=C(CN1CCNCC1=O)NCc1ccc(C(F)(F)F)nc1] | 316.279 | 2-(2-oxopiperazin-1-yl)-N-((6-(trifluoromethyl)67yridine-3-yl)methyl)acetamide |
| 117 | 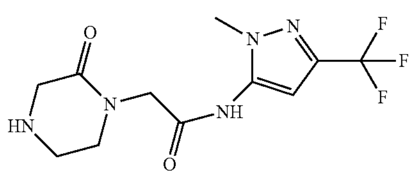 [SMILES: Cn1nc(C(F)(F)F)cc1NC(=O)CN1CCNCC1=O] | 305.256 | N-(1-methyl-3-(trifluoromethyl)-1H-pyrazol-5-yl)-2-(2-oxopiperazin-1-yl)acetamide |
| 118 | 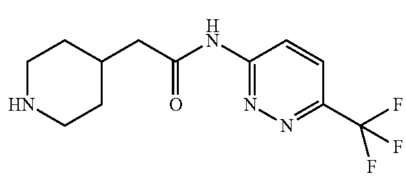 [SMILES: O=C(CC1CCNCC1)Nc1ccc(C(F)(F)F)nn1] | 287.281 | 2-(piperidin-4-yl)-N-(5-(trifluoromethyl)67yridine-2-yl)acetamide |
| 119 | 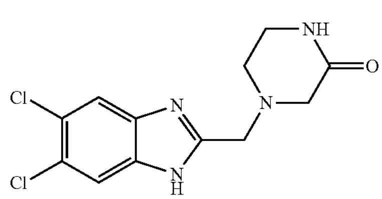 [SMILES: O=C1CN(Cc2nc3cc(Cl)c(Cl)cc3[nH]2)CCN1] | 299.156 | 4((5,6-dichloro-1H-benzo[d]imidazol-2-yl)methyl)piperazin-2-one |

TABLE 1-continued

| No. | Structure | Mol. Wt. | Chemical Name |
|---|---|---|---|
| 120 | 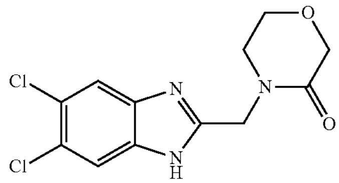 [SMILES: O=C1COCCN1Cc1nc2cc(Cl)c(Cl)cc2[nH]1] | 300.141 | 4-((5,6-dichloro-1H-benzo[d]imidazol-2-yl)methyl)morpholin-3-one |
| 121 | 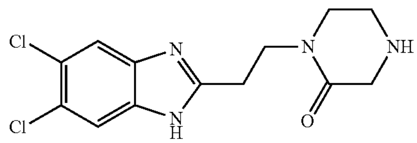 [SMILES: O=C1CNCCN1CCc1nc2cc(Cl)c(Cl)cc2[nH]1] | 313.182 | 1-(2-(5,6-dichloro-1H-benzo[d]imidazol-2-yl)ethyl)piperazin-2-one |
| 122 | 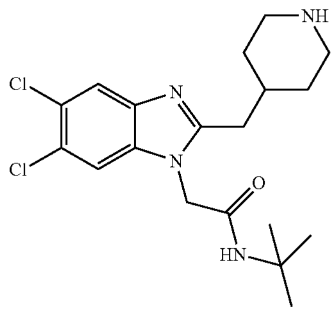 [SMILES: CC(C)(C)NC(=O)Cn1c(CC2CCNCC2)nc2cc(Cl)c(Cl)cc21] | 397.342 | N-(tert-butyl)-2-(5,6-dichloro-2-(piperidin-4-ylmethyl)-1H-benzo[d]imidazol-1-yl)acetamide |
| 123 | 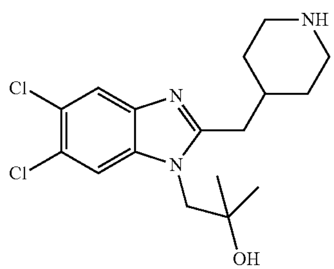 [SMILES: CC(C)(O)Cn1c(CC2CCNCC2)nc2cc(Cl)c(Cl)cc21] | 356.29 | 1-(5,6-dichloro-2-(piperidin-4-ylmethyl)-1H-benzo[d]imidazol-1-yl)-2-methylpropan-2-ol |
| 124 | 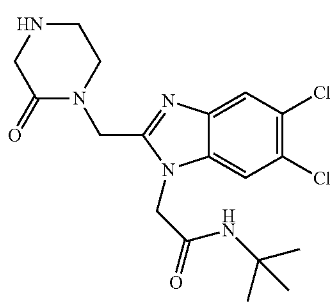 [SMILES: CC(C)(C)NC(=O)Cn1c(CN2CCNCC2=O)nc2cc(Cl)c(Cl)cc21] | 412.314 | N-(tert-butyl)-2-(5,6-dichloro-2-((2-oxopiperazin-1-yl)methyl)-1H-benzo[d]imidazol-1-yl)acetamide |
| 125 | 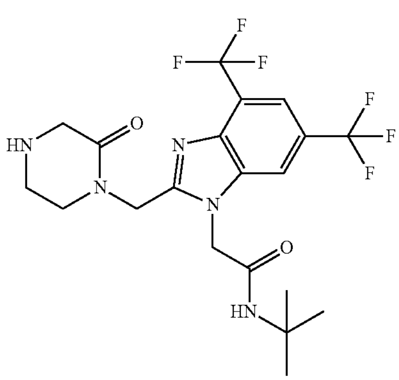 [SMILES: CC(C)(C)NC(=O)Cn1c(CN2CCNCC2=O)nc2c(C(F)(F)F)cc(C(F)(F)F)cc21] | 479.419 | N-(tert-butyl)-2-(2-((2-oxopiperazin-1-yl)methyl)-4,6-bis(trifluoromethyl)-1H-benzo[d]imidazol-1-yl)acetamide |

TABLE 1-continued

| No. | Structure | Mol. Wt. | Chemical Name |
|---|---|---|---|
| 126 | 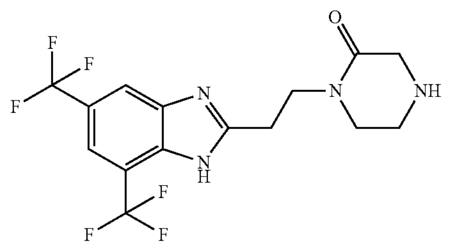 [SMILES: O=C1CNCCN1CCc1nc2cc(C(F)(F)F)cc(C(F)(F)F)c2[nH]1] | 380.288 | 1-(2-(5,7-bis(trifluoromethyl)-1H-benzo[d]imidazol-2-yl)ethyl)piperazin-2-one |
| 127 | 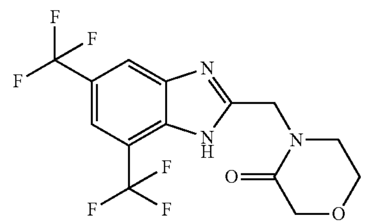 [SMILES: O=C1COCCN1Cc1nc2cc(C(F)(F)F)cc(C(F)(F)F)c2[nH]1] | 367.246 | 4-((5,7-bis(trifluoromethyl)-1H-benzo[d]imidazol-2-yl)methyl)morpholin-3-one |
| 128 | 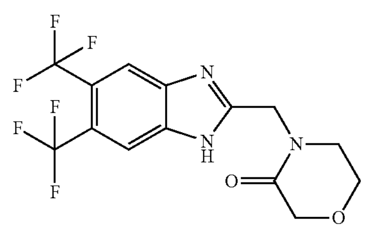 [SMILES: O=C1COCCN1Cc1nc2cc(C(F)(F)F)c(C(F)(F)F)cc2[nH]1] | 367.246 | 4-((5,6-bis(trifluoromethyl)-1H-benzo[d]imidazol-2-yl)methyl)morpholin-3-one |
| 129 | 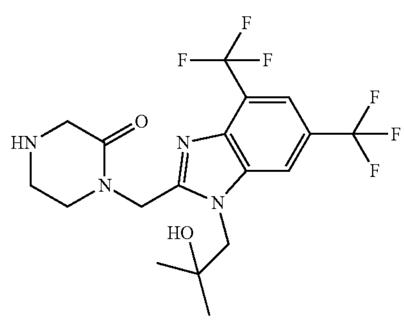 [SMILES: CC(C)(O)Cn1c(CN2CCNCC2=O)nc2c(C(F)(F)F)cc(C(F)(F)F)cc21] | 438.367 | 1-((1-(2-hydroxy-2-methylpropyl)-4,6-bis(trifluoromethyl)-1H-benzo[d]imidazol-2-yl)methyl)piperazin-2-one |
| 130 | 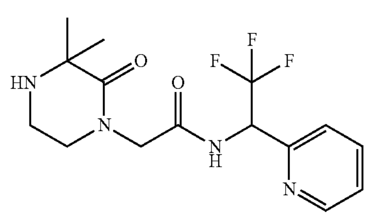 [SMILES: CC1(C)NCCN(CC(=O)NC(c2ccccn2)C(F)(F)F)C1=O] | 344.332 | 2-(3,3-dimethyl-2-oxopiperazin-1-yl)-N-(2,2,2-trifluoro-1-(69yridine-2-yl)ethyl)acetamide |
| 131 | 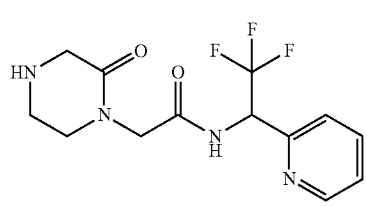 [SMILES: O=C(CN1CCNCC1=O)NC(c1ccccn1)C(F)(F)F] | 316.279 | 2-(2-oxopiperazin-1-yl)-N-(2,2,2-trifluoro-1-(69yridine-2-yl)ethyl)acetamide |

TABLE 1-continued

| No. | Structure | Mol. Wt. | Chemical Name |
|---|---|---|---|
| 132 | 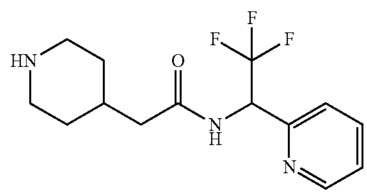 [SMILES: O=C(CC1CCNCC1)NC(c1ccccn1)C(F)(F)F] | 301.307 | 2-(piperidin-4-yl)-N-(2,2,2-trifluoro-1-(69yridine-2-yl)ethyl)acetamide |
| 133 | 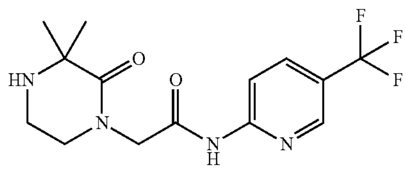 [SMILES: CC1(C)NCCN(CC(=O)Nc2ccc(C(F)(F)F)cn2)C1=O] | 330.306 | 2-(3,3-dimethyl-2-oxopiperazin-1-yl)-N-(5-(trifluoromethyl)69yridine-2-yl)acetamide |
| 134 | 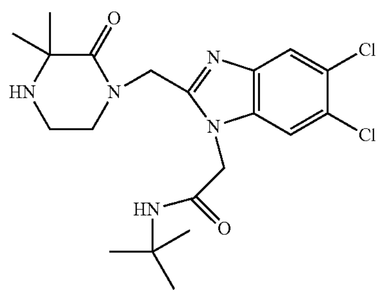 [SMILES: CC(C)(C)NC(=O)Cn1c(CN2CCNC(C)(C)C2=O)nc2cc(Cl)c(Cl)cc21] | 440.367 | N-(tert-butyl)-2-(5,6-dichloro-2-((3,3-dimethyl-2-oxopiperazin-1-yl)methyl)-1H-benzo[d]imidazol-1-yl)acetamide |
| 135 | 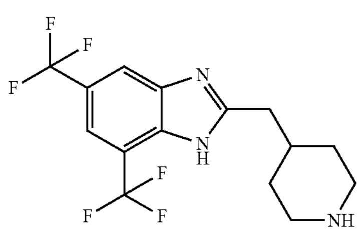 [SMILES: FC(F)(F)c1cc(C(F)(F)F)c2[nH]c(CC3CCNCC3)nc2c1] | 351.29 | 2-(piperidin-4-ylmethyl)-4,6-bis(trifluoromethyl)-1H-benzo[d]imidazole |
| 136 | 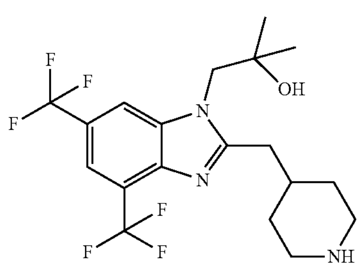 [SMILES: CC(C)(O)Cn1c(CC2CCNCC2)nc2c(C(F)(F)F)cc(C(F)(F)F)cc21] | 423.396 | 2-methyl-1-(2-(piperidin-4-ylmethyl)-4,6-bis(trifluoromethyl)-1H-benzo[d]imidazol-1-yl)propan-2-ol |
| 137 | 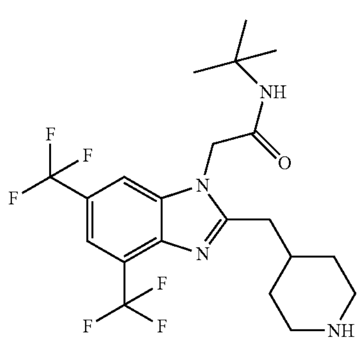 [SMILES: CC(C)(C)NC(=O)Cn1c(CC2CCNCC2)nc2c(C(F)(F)F)cc(C(F)(F)F)cc21] | 464.448 | N-(tert-butyl)-2-(2-(piperidin-4-ylmethyl)-4,6-bis(trifluoromethyl)-1H-benzo[d]imidazol-1-yl)acetamide |

TABLE 1-continued

| No. | Structure | Mol. Wt. | Chemical Name |
|---|---|---|---|
| 138 | 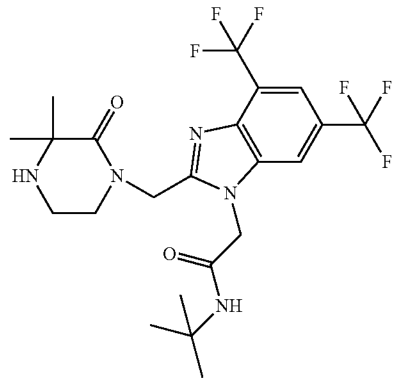 [SMILES: CC(C)(C)NC(=O)Cn1c(CN2CCNC(C)(C)C2=O)nc2c(C(F)(F)F)cc(C(F)(F)F)cc21] | 507.472 | N-(tert-butyl)-2-(2-((3,3-dimethyl-2-oxopiperazin-1-yl)methyl)-4,6-bis(trifluoromethyl)-1H-benzo[d]imidazol-1-yl)acetamide |
| 139 | 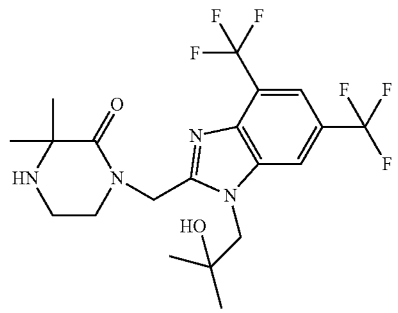 [SMILES: CC(C)(O)Cn1c(CN2CCNC(C)(C)C2=O)nc2c(C(F)(F)F)cc(C(F)(F)F)cc21] | 466.421 | 1-((1-(2-hydroxy-2-methylpropyl)-4,6-bis(trifluoromethyl)-1H-benzo[d]imidazol-2-yl)methyl)-3,3-dimethylpiperazin-2-one |
| 140 | 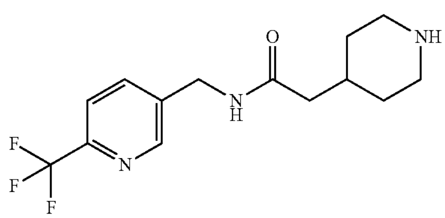 [SMILES: O=C(CC1CCNCC1)NCc1ccc(C(F)(F)F)nc1] | 301.307 | 2-(piperidin-4-yl)-N-((6-(trifluoromethyl)70yridine-3-yl)methyl)acetamide |
| 141 | 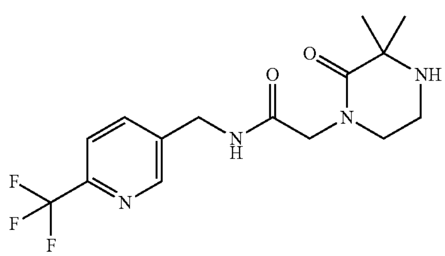 [SMILES: CC1(C)NCCN(CC(=O)NCc2ccc(C(F)(F)F)nc2)C1=O] | 344.332 | 2-(3,3-dimethyl-2-oxopiperazin-1-yl)-N-((6-(trifluoromethyl)71yridine-3-yl)methyl)acetamide |
| 142 | 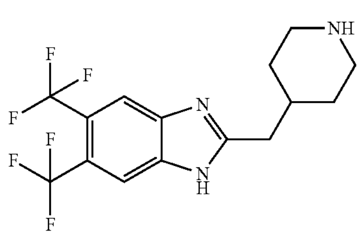 [SMILES: FC(F)(F)c1cc2nc(CC3CCNCC3)[nH]c2cc1C(F)(F)F] | 351.29 | 2-(piperidin-4-ylmethyl)-5,6-bis(trifluoromethyl)-1H-benzo[d]imidazole |

TABLE 1-continued

| No. | Structure | Mol. Wt. | Chemical Name |
|---|---|---|---|
| 143 | 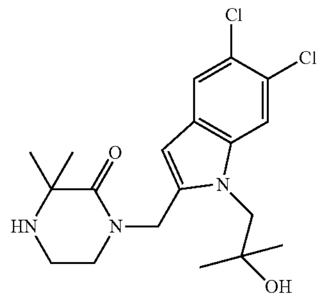 [SMILES: CC(C)(O)Cn1c(CN2CCNC(C)(C)C2=O)cc2cc(Cl)c(Cl)cc21] | 399.315 | 1-((5,6-dichloro-1-(2-hydroxy-2-methylpropyl)-1H-benzo[d]imidazol-2-yl)methyl)-3,3-dimethylpiperazin-2-one |
| 144 | 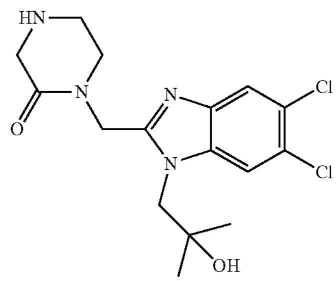 [SMILES: CC(C)(O)Cn1c(CN2CCNCC2=O)nc2cc(Cl)c(Cl)cc21] | 371.262 | 1-((5,6-dichloro-1-(2-hydroxy-2-methylpropyl)-1H-benzo[d]imidazol-2-yl)methyl)piperazin-2-one |
| 145 | 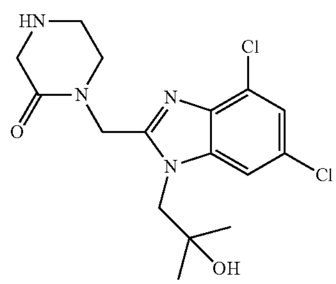 [SMILES: CC(C)(O)Cn1c(CN2CCNCC2=O)nc2c(Cl)cc(Cl)cc21] | 371.262 | 1-((4,6-dichloro-1-(2-hydroxy-2-methylpropyl)-1H-benzo[d]imidazol-2-yl)methyl)piperazin-2-one |
| 146 | 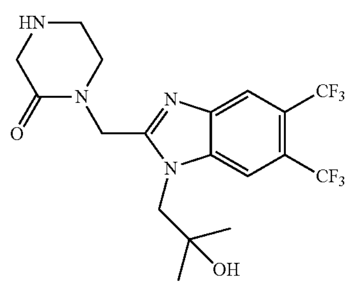 [SMILES: CC(C)(O)Cn1c(CN2CCNCC2=O)nc2cc(C(F)(F)F)c(C(F)(F)F)cc21] | 438.367 | 1-((1-(2-hydroxy-2-methylpropyl)-5,6-bis(trifluoromethyl)-1H-benzo[d]imidazol-2-yl)methyl)piperazin-2-one |
| 147 | 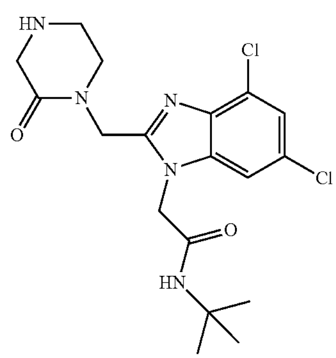 [SMILES: CC(C)(C)NC(=O)Cn1c(CN2CCNCC2=O)nc2c(Cl)cc(Cl)cc21] | 412.314 | N-(tert-butyl)-2-(4,6-dichloro-2-((2-oxopiperazin-1-yl)methyl)-1H-benzo[d]imidazol-1-yl)acetamide |

TABLE 1-continued

| No. | Structure | Mol. Wt. | Chemical Name |
|---|---|---|---|
| 148 | 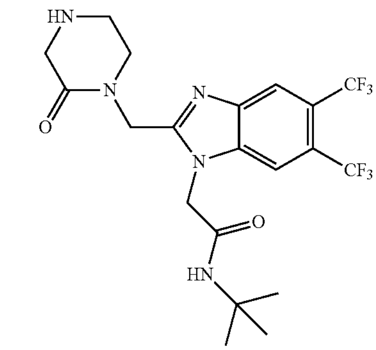 [SMILES: CC(C)(C)NC(=O)Cn1c(CN2CCNCC2=O)nc2cc(C(F)(F)F)c(C(F)(F)F)cc21] | 479.419 | N-(tert-butyl)-2-(2-((2-oxopiperazin-1-yl)methyl)-5,6-bis(trifluoromethyl)-1H-benzo[d]imidazol-1-yl)acetamide |
| 149 | 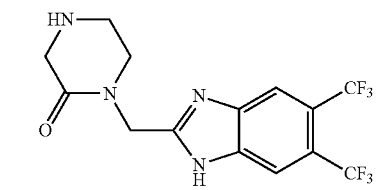 [SMILES: O=C1CNCCN1Cc1nc2cc(C(F)(F)F)c(C(F)(F)F)cc2[nH]1] | 366.262 | 1-((5,6-bis(trifluoromethyl)-1H-benzo[d]imidazol-2-yl)methyl)piperazin-2-one |
| 150 | 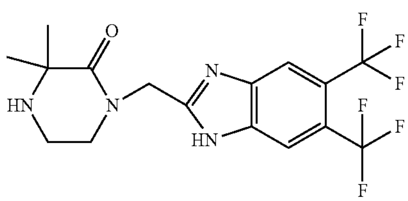 [SMILES: CC1(C)NCCN(Cc2nc3cc(C(F)(F)F)c(C(F)(F)F)cc3[nH]2)C1=O] | 394.315 | 1-((5,6-bis(trifluoromethyl)-1H-benzo[d]imidazol-2-yl)methyl)-3,3-dimethylpiperazin-2-one |
| 151 | 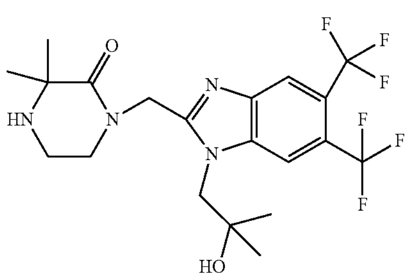 [SMILES: CC(C)(O)Cn1c(CN2CCNC(C)(C)C2=O)nc2cc(C(F)(F)F)c(C(F)(F)F)cc21] | 466.421 | 1-((1-(2-hydroxy-2-methylpropyl)-5,6-bis(trifluoromethyl)-1H-benzo[d]imidazol-2-yl)methyl)-3,3-dimethylpiperazin-2-one |
| 152 | 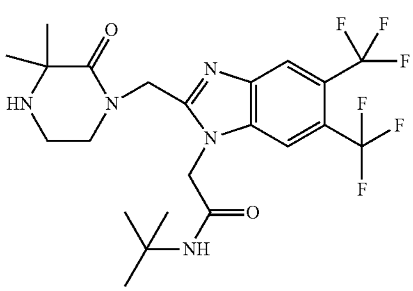 [SMILES: CC(C)(C)NC(=O)Cn1c(CN2CCNC(C)(C)C2=O)nc2cc(C(F)(F)F)c(C(F)(F)F)cc21] | 507.472 | N-(tert-butyl)-2-(2-((3,3-dimethyl-2-oxopiperazin-1-yl)methyl)-5,6-bis(trifluoromethyl)-1H-benzo[d]imidazol-1-yl)acetamide |
| 153 | 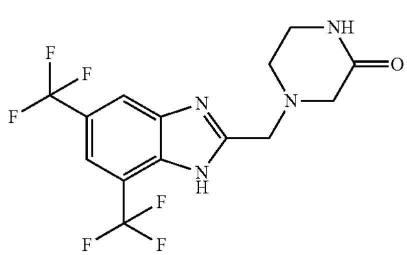 [SMILES: O=C1CN(Cc2nc3cc(C(F)(F)F)cc(C(F)(F)F)c3[nH]2)CCN1] | 366.262 | 4-((5,7-bis(trifluoromethyl)-1H-benzo[d]imidazol-2-yl)methyl)piperazin-2-one |

TABLE 1-continued

| No. | Structure | Mol. Wt. | Chemical Name |
|---|---|---|---|
| 154 | 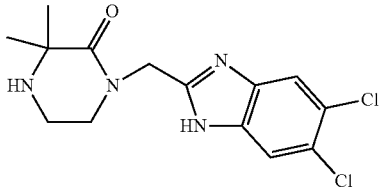 [SMILES: CC1(C)NCCN(Cc2nc3cc(Cl)c(Cl)cc3[nH]2)C1=O] | 327.209 | 1-((5,6-dichloro-1H-benzo[d]imidazol-2-yl)methyl)-3,3-dimethylpiperazin-2-one |
| 155 | 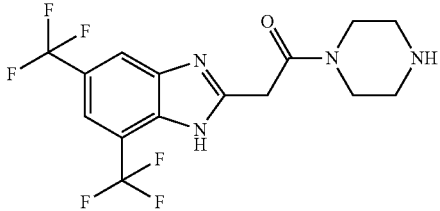 [SMILES: O=C(Cc1nc2cc(C(F)(F)F)cc(C(F)(F)F)c2[nH]1)N1CCNCC1] | 380.288 | 2-(5,7-bis(trifluoromethyl)-1H-benzo[d]imidazol-2-yl)-1-(piperazin-1-yl)ethanone |
| 156 | 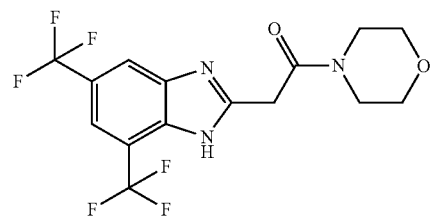 [SMILES: O=C(Cc1nc2cc(C(F)(F)F)cc(C(F)(F)F)c2[nH]1)N1CCOCC1] | 381.273 | 2-(5,7-bis(trifluoromethyl)-1H-benzo[d]imidazol-2-yl)-1-morpholinoethanone |
| 157 | 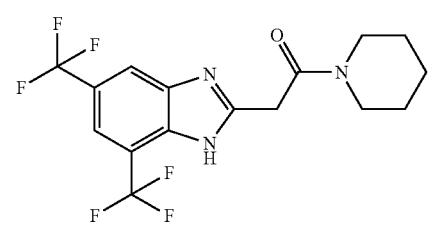 [SMILES: O=C(Cc1nc2cc(C(F)(F)F)cc(C(F)(F)F)c2[nH]1)N1CCCCC1] | 379.3 | 2-(5,7-bis(trifluoromethyl)-1H-benzo[d]imidazol-2-yl)-1-(piperidin-1-yl)ethanone |
| 158 | 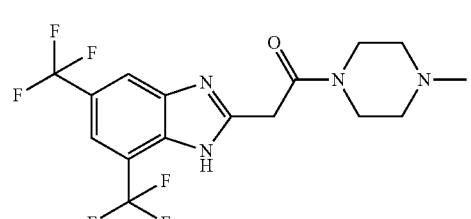 | 394.315 | 2-(5,7-bis(trifluoromethyl)-1H-benzo[d]imidazol-2-yl)-1-(4-methylpiperazin-1-yl)ethanone |
| 159 | 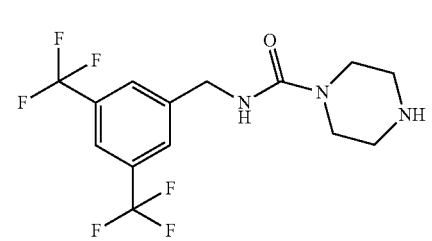 [SMILES: O=C(NCc1cc(C(F)(F)F)cc(C(F)(F)F)c1)N1CCNCC1] | 369.262 | N-(3,5-bis(trifluoromethyl)benzyl)-2-oxopiperazine-1-carboxamide |
| 160 | 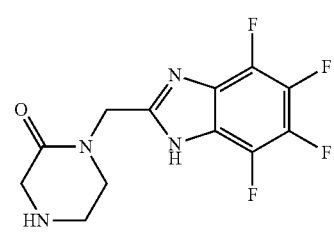 [SMILES: O=C1CNCCN1Cc1nc2c(F)c(F)c(F)c(F)c2[nH]1] | 302.228 | 1-((4,5,6,7-tetrafluoro-1H-benzo[d]imidazol-2-yl)methyl)piperazin-2-one |

TABLE 1-continued

| No. | Structure | Mol. Wt. | Chemical Name |
|---|---|---|---|
| 161 | 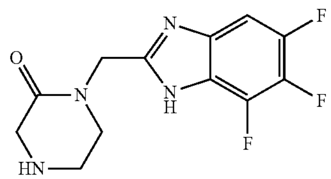 [SMILES: O=C1CNCCN1Cc1nc2cc(F)c(F)c(F)c2[nH]1] | 284.237 | 1-((5,6,7-trifluoro-1H-benzo[d]imidazol-2-yl)methyl)piperazin-2-one |
| 162 | 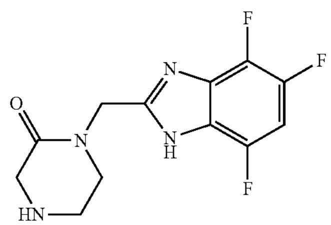 [SMILES: O=C1CNCCN1Cc1nc2c(F)c(F)cc(F)c2[nH]1] | 284.237 | 1-((4,5,7-trifluoro-1H-benzo[d]imidazol-2-yl)methyl)piperazin-2-one |
| 163 | 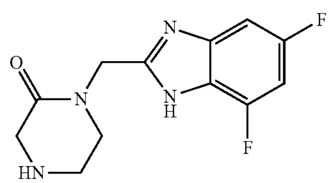 [SMILES: O=C1CNCCN1Cc1nc2cc(F)cc(F)c2[nH]1] | 266.247 | 1-((5,7-difluoro-1H-benzo[d]imidazol-2-yl)methyl)piperazin-2-one |
| 164 | 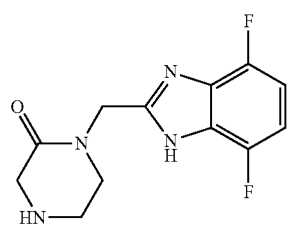 [SMILES: O=C1CNCCN1Cc1nc2c(F)ccc(F)c2[nH]1] | 266.247 | 1-((4,7-difluoro-1H-benzo[d]imidazol-2-yl)methyl)piperazin-2-one |
| 165 | 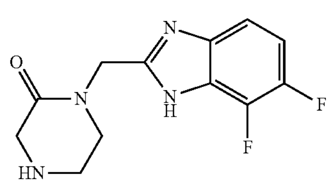 [SMILES: O=C1CNCCN1Cc1nc2ccc(F)c(F)c2[nH]1] | 266.247 | 1-((6,7-difluoro-1H-benzo[d]imidazol-2-yl)methyl)piperazin-2-one |
| 166 | 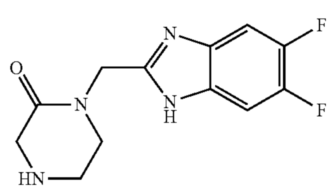 [SMILES: O=C1CNCCN1Cc1nc2cc(F)c(F)cc2[nH]1] | 266.247 | 1-((5,6-difluoro-1H-benzo[d]imidazol-2-yl)methyl)piperazin-2-one |
| 167 | 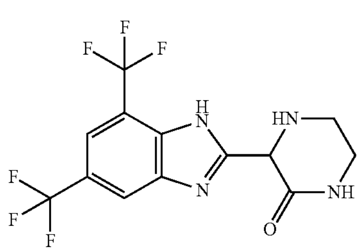 [SMILES: O=C1NCCNC1c1nc2cc(C(F)(F)F)cc(C(F)(F)F)c2[nH]1] | 352.235 | 3-(5,7-bis(trifluoromethyl)-1H-benzo[d]imidazol-2-yl)piperazin-2-one |

TABLE 1-continued

| No. | Structure | Mol. Wt. | Chemical Name |
|---|---|---|---|
| 168 | 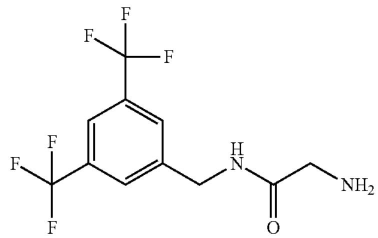 [SMILES: NCC(=O)NCc1cc(C(F)(F)F)cc(C(F)(F)F)c1] | 300.2 | 2-amino-N-(3,5-bis(trifluoromethyl)benzyl)acetamide |
| 169 | 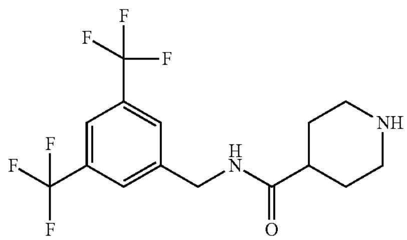 [SMILES: O=C(NCc1cc(C(F)(F)F)cc(C(F)(F)F)c1)C1CCNCC1] | 354.291 | N-(3,5-bis(trifluoromethyl)benzyl)piperidine-4-carboxamide |
| 170 | 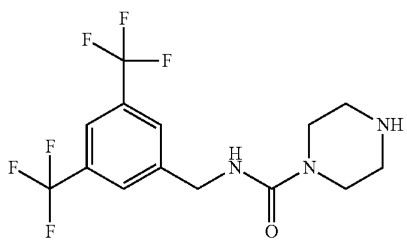 [SMILES: O=C(NCc1cc(C(F)(F)F)cc(C(F)(F)F)c1)N1CCNCC1] | 355.279 | N-(3,5-bis(trifluoromethyl)benzyl)piperazine-1-carboxamide |
| 171 | 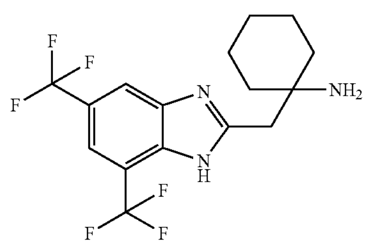 [SMILES: NC1(Cc2nc3cc(C(F)(F)F)cc(C(F)(F)F)c3[nH]2)CCCCC1] | 365.317 | 1-((5,7-bis(trifluoromethyl)-1H-benzo[d]imidazol-2-yl)methyl)cyclohexanamine |
| 172 | 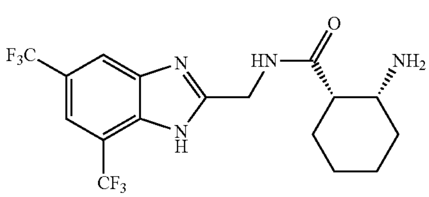 [SMILES: N[C@@H]1CCCC[C@@H]1C(=O)NCc1nc2cc(C(F)(F)F)cc(C(F)(F)F)c2[nH]1] | 408.341 | (1S,2R)-2-amino-N-((5,7-bis(trifluoromethyl)-1H-benzo[d]imidazol-2-yl)methyl)cyclohexanecarboxamide |
| 173 | 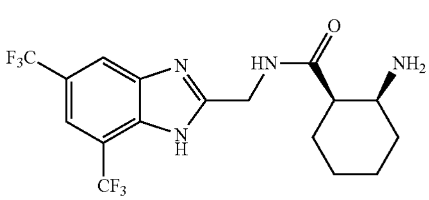 [SMILES: N[C@H]1CCCC[C@H]1C(=O)NCc1nc2cc(C(F)(F)F)cc(C(F)(F)F)c2[nH]1] | 408.341 | (1R,2S)-2-amino-N-((5,7-bis(trifluoromethyl)-1H-benzo[d]imidazol-2-yl)methyl)cyclohexanecarboxamide |
| 174 | 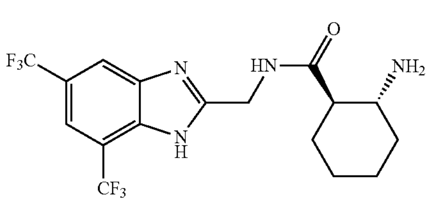 [SMILES: N[C@@H]1CCCC[C@H]1C(=O)NCc1nc2cc(C(F)(F)F)cc(C(F)(F)F)c2[nH]1] | 408.341 | (1R,2R)-2-amino-N--((5,7-bis(trifluoromethyl)-1H-benzo[d]imidazol-2-yl)methyl)cyclohexanecarboxamide |

TABLE 1-continued

| No. | Structure | Mol. Wt. | Chemical Name |
|---|---|---|---|
| 175 | 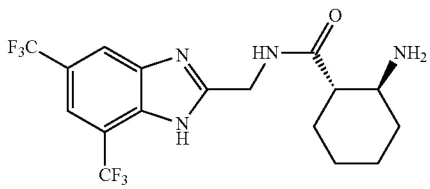 [SMILES: N[C@H]1CCCC[C@@H]1C(=O)NCc1nc2cc(C(F)(F)F)cc(C(F)(F)F)c2[nH]1] | 408.341 | (1S,2S)-2-amino-N-((5,7-bis(trifluoromethyl)-1H-benzo[d]imidazol-2-yl)methyl)cyclohexanecarboxamide |
| 176 | 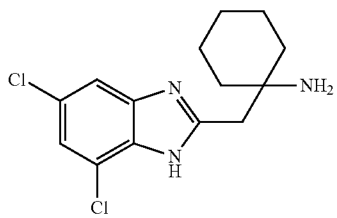 [SMILES: NC1(Cc2nc3cc(Cl)cc(Cl)c3[nH]2)CCCCC1] | 298.211 | 1-(5,7-dichloro-1H-benzo[d]imidazol-2-yl)methyl)cyclohexamine |
| 177 | 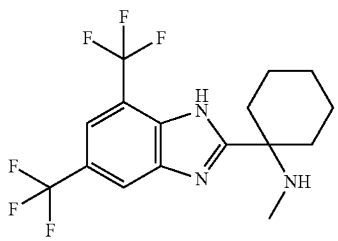 [SMILES: CNC1(c2nc3cc(C(F)(F)F)cc(C(F)(F)F)c3[nH]2)CCCCC1] | 365.317 | 1-(5,7-bis(trifluoromethyl)-1H-benzo[d]imidazol-2-yl)-N-methylcyclohexanamine |
| 178 | 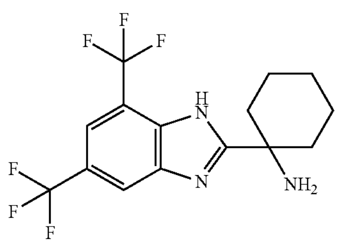 [SMILES: NC1(c2nc3cc(C(F)(F)F)cc(C(F)(F)F)c3[nH]2)CCCCC1] | 351.29 | 1-(5,7-bis(trifluoromethyl)-1H-benzo[d]imidazol-2-yl)cyclohexanamine |
| 179 | 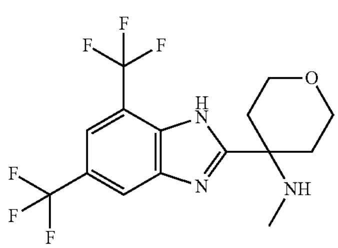 [SMILES: CNC1(c2nc3cc(C(F)(F)F)cc(C(F)(F)F)c3[nH]2)CCOCC1] | 367.29 | 4-(5,7-bis(trifluoromethyl)-1H-benzo[d]imidazol-2-yl)-N-methyltetrahydro-2H-pyran-4-amine |
| 180 | 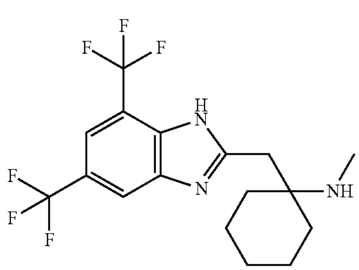 [SMILES: CNC1(Cc2nc3cc(C(F)(F)F)cc(C(F)(F)F)c3[nH]2)CCCCC1] | 379.343 | 1-((5,7-bis(trifluoromethyl)-1H-benzo[d]imidazol-2-yl)methyl)-N-methylcyclohexanamine |

TABLE 1-continued

| No. | Structure | Mol. Wt. | Chemical Name |
|---|---|---|---|
| 181 | 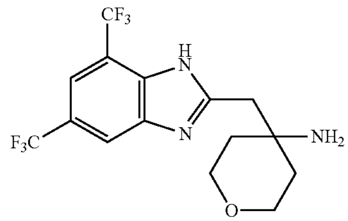 [SMILES: NC1(Cc2nc3cc(C(F)(F)F)cc(C(F)(F)F)c3[nH]2)CCOCC1] | 367.29 | 4-((5,7-bis(trifluoromethyl)-1H-benzo[d]imidazol-2-yl)methyl)tetrahydro-2H-pyran-4-amine |
| 182 | 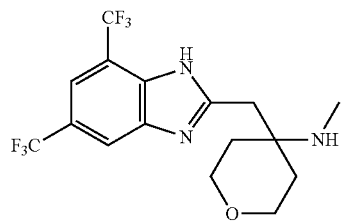 [SMILES: CNC1(Cc2nc3cc(C(F)(F)F)cc(C(F)(F)F)c3[nH]2)CCOCC1] | 381.316 | 4-((5,7-bis(trifluoromethyl)-1H-benzo[d]imidazol-2-yl)methyl)-N-methyltetrahydro-2H-pyran-4-amine |
| 183 | 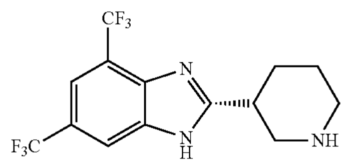 | 337.264 | (R)-2-(piperidin-3-yl)-4,6-bis(trifluoromethyl)-1H-benzo[d]imidazole |
| 184 | 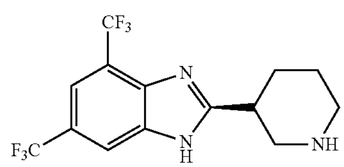 | 337.264 | (S)-2-(piperidin-3-yl)-4,6-bis(trifluoromethyl)-1H-benzo[d]imidazole |
| 185 | 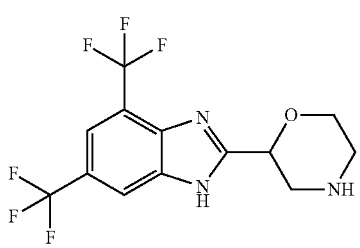 [SMILES: FC(F)(F)c1cc(C(F)(F)F)c2nc(C3CNCCO3)[nH]c2c1] | 339.236 | 2-(4,6-bis(trifluoromethyl)-1H-benzo[d]imidazol-2-yl)morpholine |
| 186 | 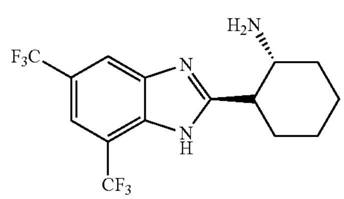 | 351.29 | (1R,2R)-2-(5,7-bis(trifluoromethyl)-1H-benzo[d]imidazol-2-yl)cyclohexanamine |
| 187 | 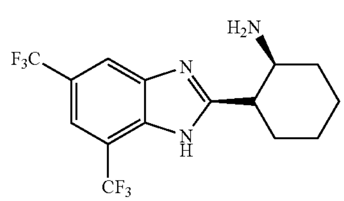 | 351.29 | (1S,2R)-2-(5,7-bis(trifluoromethyl)-1H-benzo[d]imidazol-2-yl)cyclohexanamine |

TABLE 1-continued

| No. | Structure | Mol. Wt. | Chemical Name |
|---|---|---|---|
| 188 | 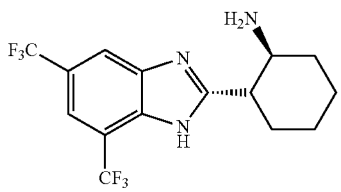 | 351.29 | (1S,2S)-2-(5,7-bis(trifluoromethyl)-1H-benzo[d]imidazol-2-yl)cyclohexanamine |
| 189 | 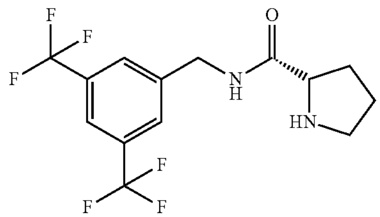 | 340.264 | (S)-N-(3,5-bis(trifluoromethyl)benzyl)pyrrolidine-2-carboxamide |
| 190 | 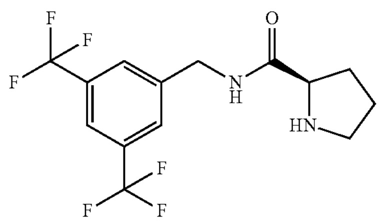 [SMILES: O=C(NCc1cc(C(F)(F)F)cc(C(F)(F)F)c1)[C@H]1CCCN1] | 340.264 | (R)-N-(3,5-bis(trifluoromethyl)benzyl)pyrrolidine-2-carboxamide |
| 191 | 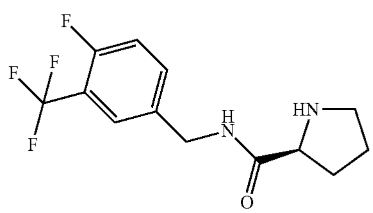 [SMILES: O=C(NCc1ccc(F)c(C(F)(F)F)c1)[C@@H]1CCCN1] | 290.257 | (S)-N-(4-fluoro-3-(trifluoromethyl)benzyl)pyrrolidine-2-carboxamide |
| 192 | 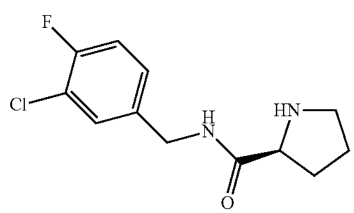 [SMILES: O=C(NCc1ccc(F)c(Cl)c1)[C@@H]1CCCN1] | 256.704 | (S)-N-(3-chloro-4-fluorobenzyl)pyrrolidine-2-carboxamide |
| 193 | 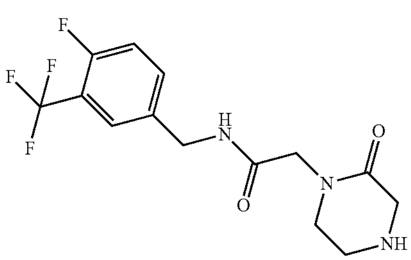 [SMILES: O=C(CN1CCNCC1=O)NCc1ccc(F)c(C(F)(F)F)c1] | 333.281 | N-(4-fluoro-3-(trifluoromethyl)benzyl)-2-(2-oxopiperazin-1-yl)acetamide |
| 194 | 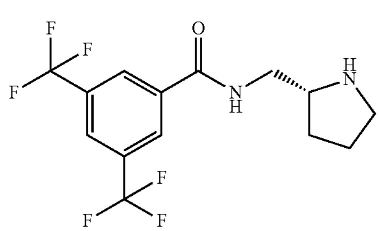 [SMILES: O=C(NC[C@H]1CCCN1)c1cc(C(F)(F)F)cc(C(F)(F)F)c1] | 340.264 | (R)-N-(pyrrolidin-2-ylmethyl)-3,5-bis(trifluoromethyl)benzamide |

TABLE 1-continued

| No. | Structure | Mol. Wt. | Chemical Name |
|---|---|---|---|
| 195 | 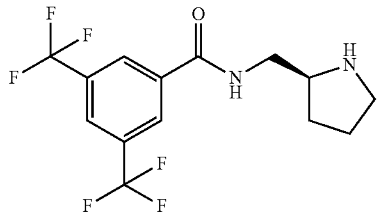 [SMILES: O=C(NC[C@@H]1CCCN1)c1cc(C(F)(F)F)cc(C(F)(F)F)c1] | 340.264 | (S)-N-(pyrrolidin-2-ylmethyl)-3,5-bis(trifluoromethyl)benzamide |
| 196 | 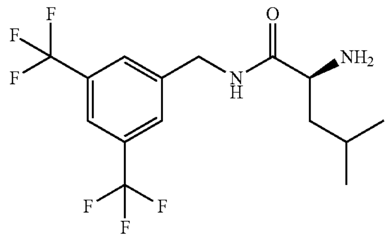 [SMILES: CC(C)C[C@H](N)C(=O)NCc1cc(C(F)(F)F)cc(C(F)(F)F)c1] | 356.307 | (S)-2-amino-N-(3,5-bis(trifluoromethyl)benzyl)-4-methylpentanamide |
| 197 | 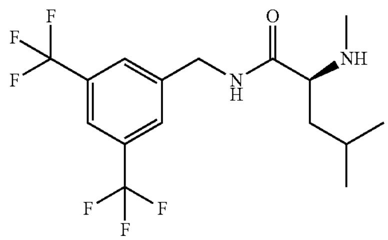 [SMILES: CN[C@@H](CC(C)C)C(=O)NCc1cc(C(F)(F)F)cc(C(F)(F)F)c1] | 370.333 | (S)-N-(3,5-bis(trifluoromethyl)benzyl)-4-methyl-2-(methylamino)pentanamide |
| 198 | 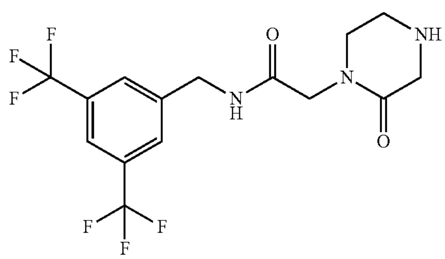 [SMILES: O=C(CN1CCNCC1=O)NCc1cc(C(F)(F)F)cc(C(F)(F)F)c1] | 383.289 | N-(3,5-bis(trifluoromethyl)benzyl)-2-(2-oxopiperazin-1-yl)acetamide |
| 199 | 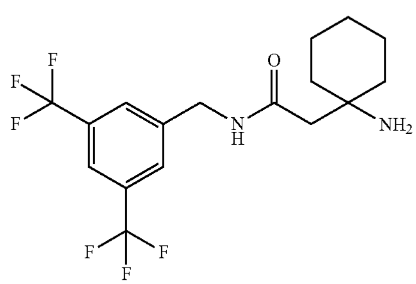 [SMILES: NC1(CC(=O)NCc2cc(C(F)(F)F)cc(C(F)(F)F)c2)CCCCC1] | 382.344 | 2-(1-aminocyclohexyl)-N-(3,5-bis(trifluoromethyl)benzyl)acetamide |
| 200 | 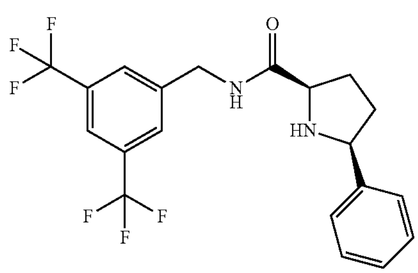 [SMILES: O=C(NCc1cc(C(F)(F)F)cc(C(F)(F)F)c1)[C@H]1CC[C@@H](c2ccccc2)N1] | 416.36 | (2R,5S)-N-(3,5-bis(trifluoromethyl)benzyl)-5-phenylpyrrolidine-2-carboxamide |

TABLE 1-continued

| No. | Structure | Mol. Wt. | Chemical Name |
|---|---|---|---|
| 201 | 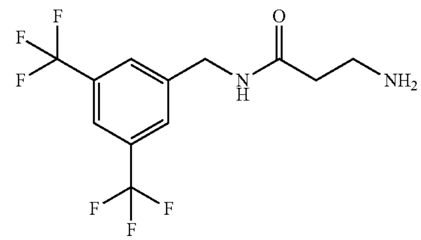 [SMILES: NCCC(=O)NCc1cc(C(F)(F)F)cc(C(F)(F)F)c1] | 314.227 | 3-amino-N-(3,5-bis(trifluoromethyp benzyl)propanamide |
| 202 | 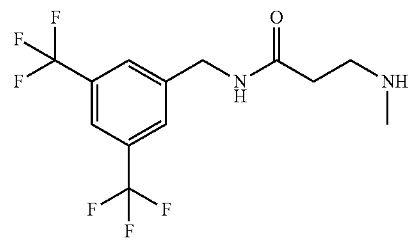 [SMILES: CNCCC(=O)NCc1cc(C(F)(F)F)cc(C(F)(F)F)c1] | 328.253 | N-(3,5-bis(trifluoromethyl)benzyl)-3-(methylamino)propanamide |
| 203 | 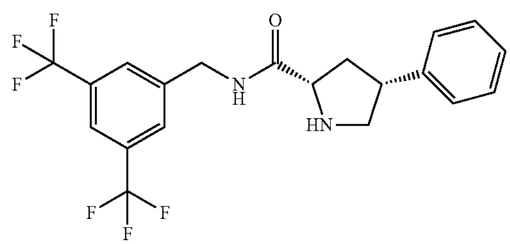 [SMILES: O=C(NCc1cc(C(F)(F)F)cc(C(F)(F)F)c1)[C@@H]1C[C@H](c2ccccc2)CN1] | 416.36 | (2S,4R)-N-(3,5-(trifluoromethyl)benzyl)-4-phenylpyrrolidine-2-carboxamide |
| 204 | 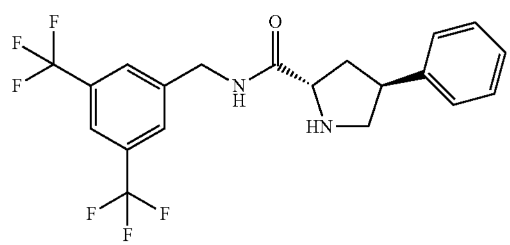 [SMILES: O=C(NCc1cc(C(F)(F)F)cc(C(F)(F)F)c1)[C@@H]1C[C@@H](c2ccccc2)CN1] | 416.36 | (2S,4S)-N-(3,5-bis(trifluoromethyl)benzyl)-4-phenylpyrrolidine-2-carboxamide |
| 205 | 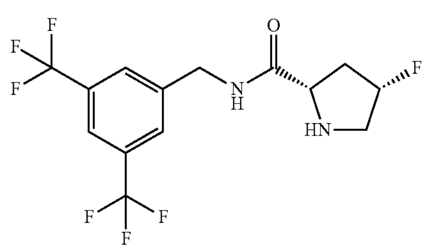 [SMILES: O=C(NCc1cc(C(F)(F)F)cc(C(F)(F)F)c1)[C@@H]1C[C@H](F)CN1] | 358.255 | (2S,4S)-N-(3,5-(trifluoromethyl)benzyl)-4-fluoropyrrolidine-2-carboxamide |
| 206 | 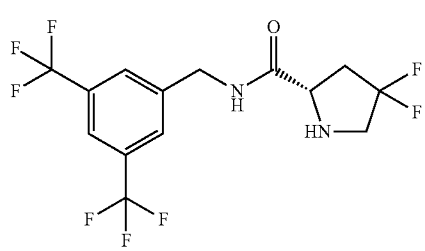 [SMILES: O=C(NCc1cc(C(F)(F)F)cc(C(F)(F)F)c1)[C@@H]1CC(F)(F)CN1] | 376.245 | (S)-N-(3,5-bis(trifluoromethyl)benzyl)-4,4-difluoropyrrolidine-2-carboxamide |

TABLE 1-continued

| No. | Structure | Mol. Wt. | Chemical Name |
|---|---|---|---|
| 207 | 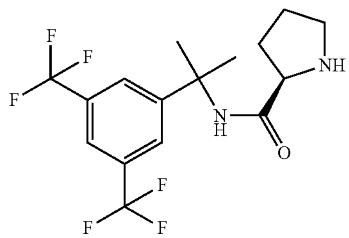 [SMILES: CC(C)(NC(=O)[C@H]1CCCN1)c1cc(C(F)(F)F)cc(C(F)(F)F)c1] | 368.317 | (R)-N-(2-(3,5-bis(trifluoromethyl)phenyl)propan-2-yl)pyrrolidine-2-carboxamide |
| 208 | 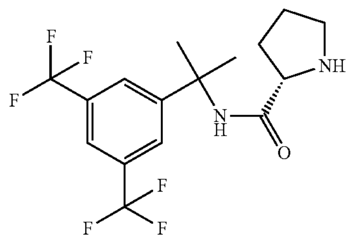 [SMILES: CC(C)(NC(=O)[C@@H]1CCCN1)c1cc(C(F)(F)F)cc(C(F)(F)F)c1] | 368.317 | (S)-N-(2-(3,5-bis(trifluoromethyl)phenyl)propan-2-yl)pyrrolidine-2-carboxamide |
| 209 | 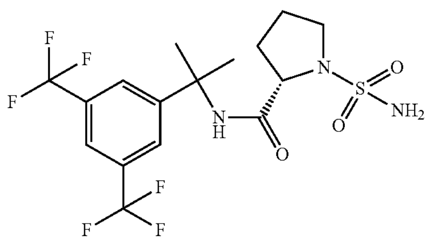 [SMILES: CC(C)(NC(=O)[C@@H]1CCCN1S(N)(=O)=O)c1cc(C(F)(F)F)cc(C(F)(F)F)c1] | 447.396 | (S)-N-(2-(3,5-bis(trifluoromethyl)phenyl)propan-2-yl)-1-sulfamoylpyrrolidine-2-carboxamide |
| 210 | 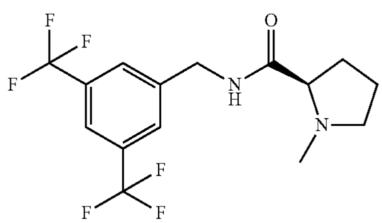 [SMILES: CN1CCC[C@@H]1C(=O)NCc1cc(C(F)(F)F)cc(C(F)(F)F)c1] | 354.291 | (R)-N-(3,5-bis(trifluoromethyl)benzyl)-1-methylpyrrolidine-2-carboxamide |
| 211 | 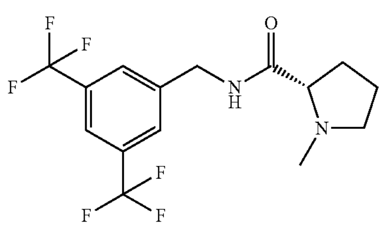 [SMILES: CN1CCC[C@H]1C(=O)NCc1cc(C(F)(F)F)cc(C(F)(F)F)c1] | 354.291 | (S)-N-(3,5-bis(trifluoromethyl)benzyl)-1-methylpyrrolidine-2-carboxamide |
| 212 | 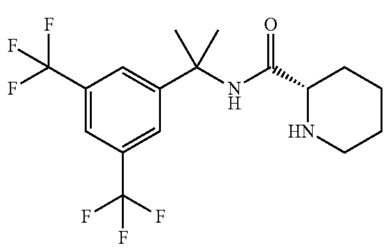 [SMILES: CC(C)(NC(=O)[C@@H]1CCCCN1)c1cc(C(F)(F)F)cc(C(F)(F)F)c1] | 382.344 | (S)-N-(2-(3,5-bis(trifluoromethyl)phenyl)propan-2-yl)piperidine-2-carboxamide |

TABLE 1-continued

| No. | Structure | Mol. Wt. | Chemical Name |
|---|---|---|---|
| 213 | 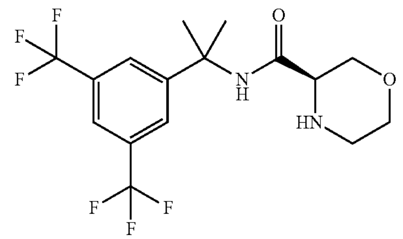 [SMILES: CC(C)(NC(=O)[C@H]1COCCN1)c1cc(C(F)(F)F)cc(C(F)(F)F)c1] | 384.317 | (R)-N-(2-(3,5-bis(trifluoromethyl)phenyl)propan-2-yl)morpholine-3-carboxamide |
| 214 | 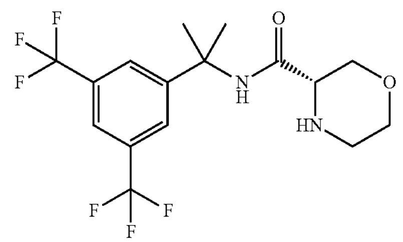 [SMILES: CC(C)(NC(=O)[C@@H]1COCCN1)c1cc(C(F)(F)F)cc(C(F)(F)F)c1] | 384.317 | (S)-N-(2-(3,5-bis(trifluoromethyl)phenyl)propan-2-yl)morpholine-3-carboxamide |
| 215 | 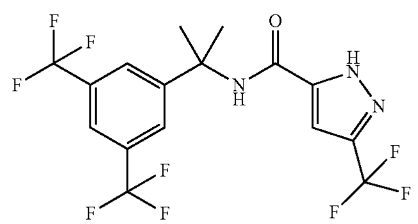 [SMILES: CC(C)(NC(=O)c1cc(C(F)(F)F)n[nH]1)c1cc(C(F)(F)F)cc(C(F)(F)F)c1] | 433.272 | N-(2-(3,5-bis(trifluoromethyl)phenyl)propan-2-yl)-3-(trifluoromethyl)-1H-pyrazole-5-carboxamide |
| 216 | 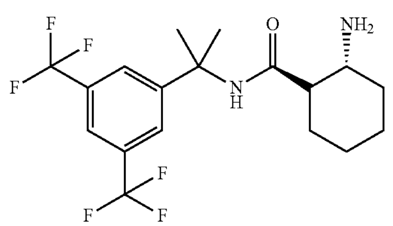 | 396.37 | (1S,2R)-2-amino-N-(2-(3,5-bis(trifluoromethyl)phenyl)propan-2-yl)cyclohexanecarboxamide |
| 217 | 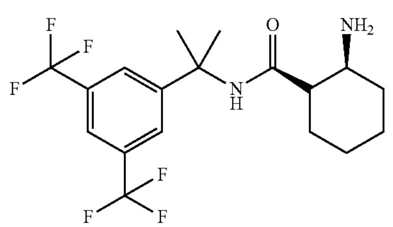 | 396.37 | (1S,2S)-2-amino-N-(2-(3,5-bis(trifluoromethyl)phenyl)propan-2-yl)cyclohexanecarboxamide |
| 218 | 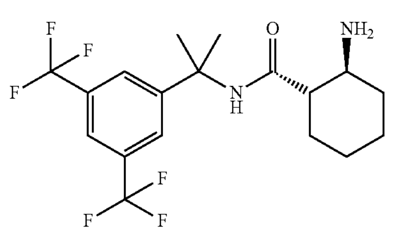 | 396.37 | (1S,2S)-2-amino-N-(2-(3,5-bis(trifluoromethyl)phenyl)propan-2-yl)cyclohexanecarboxamide |

TABLE 1-continued

| No. | Structure | Mol. Wt. | Chemical Name |
|---|---|---|---|
| 219 | 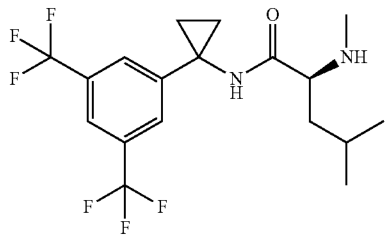 [SMILES: CN[C@@H](CC(C)C)C(=O)NC1(c2cc(C(F)(F)F)cc(C(F)(F)F)c2)CC1] | 396.37 | (S)-N-(1-(3,5-bis(trifluoromethyl)phenyl)cyclopropyl)-4-methyl-2-(methylamino)pentanamide |
| 220 | 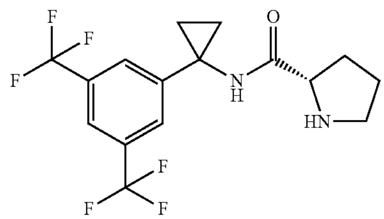 [SMILES: O=C(NC1(c2cc(C(F)(F)F)cc(C(F)(F)F)c2)CC1)[C@@H]1CCCN1] | 366.301 | (S)-N-(1-(3,5-bis(trifluoromethyl)phenyl)cyclopropyl)pyrrolidine-2-carboxamide |
| 221 | 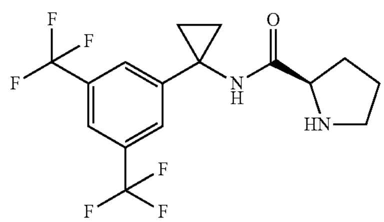 [SMILES: O=C(NC1(c2cc(C(F)(F)F)cc(C(F)(F)F)c2)CC1)[C@H]1CCCN1] | 366.301 | (R)-N-(1-(3,5-bis(trifluoromethyl)phenyl)cyclopropyl)pyrrolidine-2-carboxamide |
| 222 | 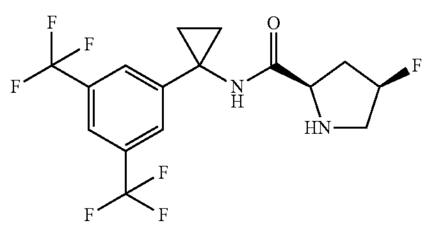 [SMILES: O=C(NC1(c2cc(C(F)(F)F)cc(C(F)(F)F)c2)CC1)[C@H]1C[C@@H](F)CN1] | 384.292 | (2R,4R)-N-(1-(3,5-bis(trifluoromethyl)phenyl)cyclopropyl)-4-fluoropyrrolidine-2-carboxamide |
| 223 | 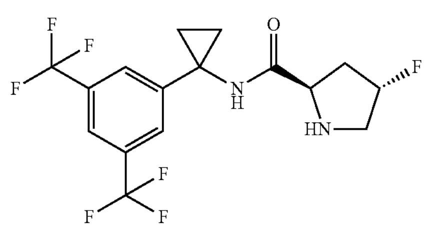 [SMILES: O=C(NC1(c2cc(C(F)(F)F)cc(C(F)(F)F)c2)CC1)[C@H]1C[C@H](F)CN1] | 384.292 | (2R,4S)-N-(1-(3,5-bis(trifluoromethyl)phenyl)cyclopropyl)-4-fluoropyrrolidine-2-carboxamide |
| 224 | 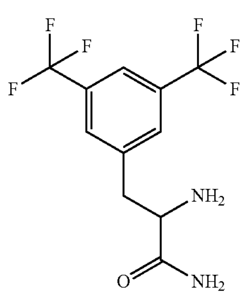 [SMILES: NC(=O)C(N)Cc1cc(C(F)(F)F)cc(C(F)(F)F)c1] | 300.2 | 2-amino-3-(3,5-bis(trifluoromethyl)phenyl)propanamide |

TABLE 1-continued

| No. | Structure | Mol. Wt. | Chemical Name |
|---|---|---|---|
| 225 | 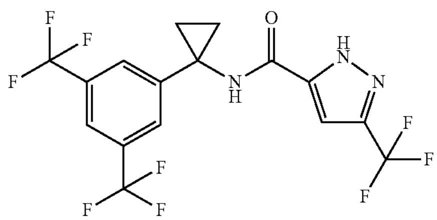 [SMILES: O=C(NC1(c2cc(C(F)(F)F)cc(C(F)(F)F)c2)CC1)c1cc(C(F)(F)F)n[nH]1] | 431.256 | N-(1-(3,5-bis(trifluoromethyl)phenyl)cyclopropyl)-3-(trifluoromethyl)-1H-pyrazole-5-carboxamide |
| 226 | 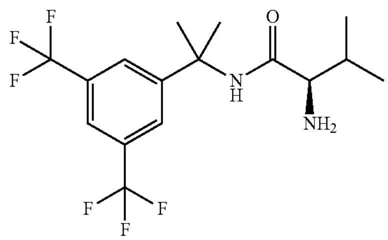 [SMILES: CC(C)[C@@H](N)C(=O)NC(C)(C)c1cc(C(F)(F)F)cc(C(F)(F)F)c1] | 370.333 | (R)-2-amino-N-(2-(3,5-bis(trifluoromethyl)phenyl)propan-2-yl)-3-methylbutanamide |
| 227 | 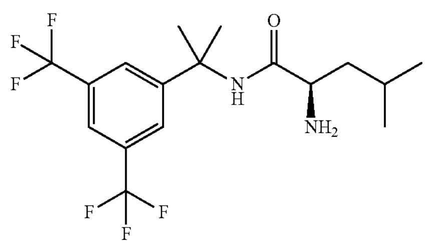 [SMILES: CC(C)C[C@@H](N)C(=O)NC(C)(C)c1cc(C(F)(F)F)cc(C(F)(F)F)c1] | 384.36 | (R)-2-amino-N-(2-(3,5-bis(trifluoromethyl)phenyl)propan-2-yl)-4-methylpentanamide |
| 228 | 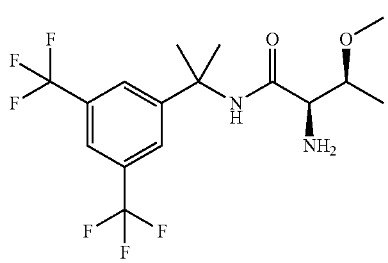 [SMILES: CO[C@@H](C)[C@@H](N)C(=O)NC(C)(C)c1cc(C(F)(F)F)cc(C(F)(F)F)c1] | 386.333 | (2R,3S)-2-amino-N-(2-(3,5-bis(trifluoromethyl)phenyl)propan-2-yl)-3-methoxybutanamide |
| 229 | 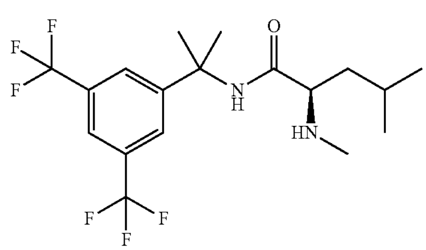 [SMILES: CN[C@H](CC(C)C)C(=O)NC(C)(C)c1cc(C(F)(F)F)cc(C(F)(F)F)c1] | 398.386 | (R)-N-(2-(3,5-bis(trifluoromethyl)phenyl)propan-2-yl)-4-methyl-2-(methylamino)pentanamide |
| 230 | 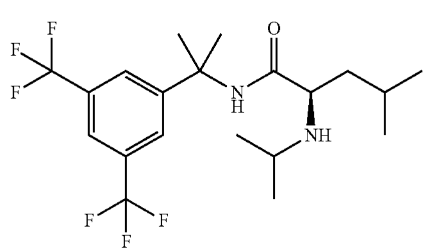 [SMILES: CC(C)C[C@@H](NC(C)C)C(=O)NC(C)(C)c1cc(C(F)(F)F)cc(C(F)(F)F)c1] | 426.44 | (R)-N-(2-(3,5-bis(trifluoromethyl)phenyl)propan-2-yl)-2-(isopropylamino)-4-methylpentanamide |

TABLE 1-continued

| No. | Structure | Mol. Wt. | Chemical Name |
|---|---|---|---|
| 231 | 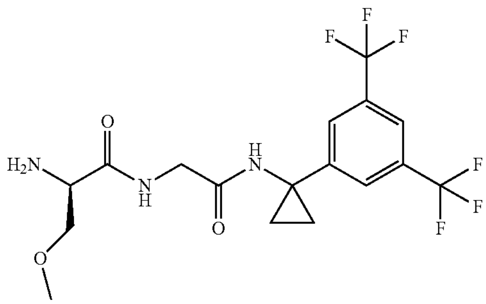 [SMILES: COC[C@@H](N)C(=O)NCC(=O)NC1(c2cc(C(F)(F)F)cc(C(F)(F)F)c2)CC1] | 427.341 | (R)-2-amino-N-(2-((1-(3,5-bis(trifluoromethyl)phenyl)cyclopropyl)amino)-2-oxoethyl)-3-methoxypropanamide |
| 232 | 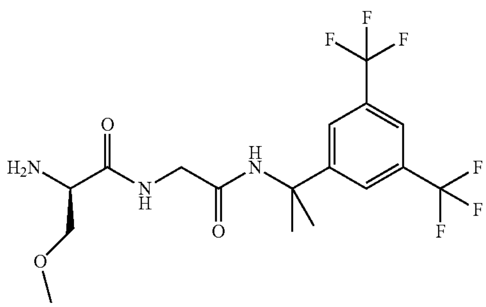 [SMILES: COC[C@@H](N)C(=O)NCC(=O)NC(C)(C)c1cc(C(F)(F)F)cc(C(F)(F)F)c1] | 429.357 | (R)-2-amino-N-(2-((2-(3,5-bis(trifluoromethyl)phenyl)propan-2-yl)amino)-2-oxoethyl)-3-methoxypropanamide |
| 233 | 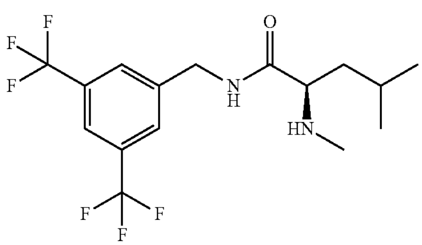 [SMILES: CN[C@H](CC(C)C)C(=O)NCc1cc(C(F)(F)F)cc(C(F)(F)F)c1] | 370.333 | (R)-N-(3,5-(trifluoromethyl)benzyl)-4-methyl-2-(methylamino)pentanamide |
| 234 | 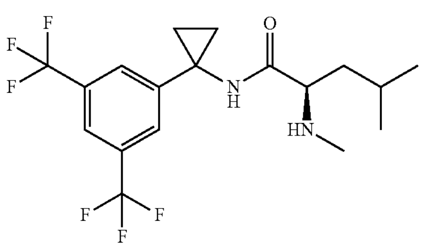 [SMILES: CN[C@H](CC(C)C)C(=O)NC1(c2cc(C(F)(F)F)cc(C(F)(F)F)c2)CC1] | 396.37 | (R)-N-(1-(3,5-bis(trifluoromethyl)phenyl)cyclopropyl)-4-methyl-2-(methylamino)pentanamide |
| 235 | 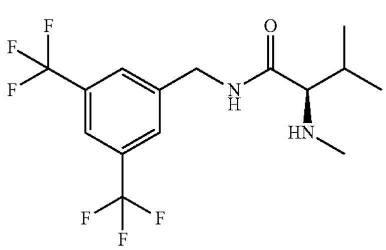 [SMILES: CN[C@@H](C(=O)NCc1cc(C(F)(F)F)cc(C(F)(F)F)c1)C(C)C] | 356.307 | (R)-N-(3,5-bis(trifluoromethyl)benzyl)-3-methyl-2-(methylamino)butanamide |

TABLE 1-continued

| No. | Structure | Mol. Wt. | Chemical Name |
|---|---|---|---|
| 236 | 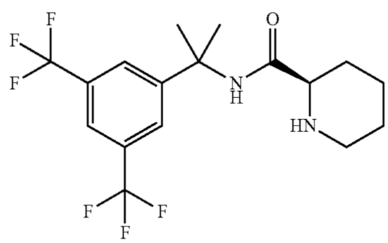 [SMILES: CC(C)(NC(=O)[C@H]1CCCCN1)c1cc(C(F)(F)F)cc(C(F)(F)F)c1] | 382.348 | (R)-N-(2-(3,5-bis(trifluoromethyl)phenyl)propan-2-yl)piperidine-2-carboxamide |

Example 20

Ion Channel Studies

The generation of a HEK 293F cell line stably expressing human $Na_v1.7$ was achieved by co-transfecting human SCN9A and human SCN1B cDNAs, subcloned into plasmid vectors and utilizing standard transfection techniques. Clones were selected using appropriate selection agents (0.3 mg/mL Zeocin and 0.8 mg/mL Geneticin) and maintained in Dulbecco's Modified Eagle medium, 10% fetal bovine serum, 1% non essential amino acids to ~80% confluence at 37° C. in a humidified incubator with 95% atmosphere and 5% $CO_2$.

On the day of each experiment, cells that were grown to 80% confluence in a T75 flask were harvested for use on PatchXpress (Molecular Devices, CA, USA). Following a recovery period at 37° C. in a humidified incubator with 95% atmosphere and 5% $CO_2$ in Dulbecco's Modified Eagle Medium, the media was replaced with an external recording solution containing (in mM): 90 TEACl, 50 NaCl, 1.8 $CaCl_2$, 1 $MgCl_2$, 10 HEPES, 10 glucose, adjusted to pH 7.4 with TEAOH and 300 mOsm with sucrose. The internal recording solution contained (in mM): 129 CsF, 2 $MgCl_2$, 11 EGTA, 10 HEPES, 6 NaCl, 3 $Na_2ATP$ adjusted to pH 7.2 with CsOH and 280 mOsm with sucrose. The automated liquid handling facility of PatchXpress dispensed cells and added compound.

Modulation of $Na_v1.7$ channels by compounds was assessed by promoting the channels into the inactivated state using a conditioning voltage pulse of variable amplitude, followed by a brief hyperpolarizing pulse with a subsequent depolarized voltage step to measure the current amplitude in the presence and absence of compound. Exemplary data are provided in FIG. 1.

Example 21

Assays

Modulation of Ion Channel Activity

The compounds described herein can also be assayed for modulation of other voltage gated channels (e.g., other $Na^+$ channel isoforms or $Ca^{2+}$ channels such as $Ca_v3.2$ T-type channels). Additional methods are known in the art. Exemplary data obtained according to these methods are also shown in FIG. 1.

$Na_v1.5$ Assay

Inhibition of the TTX-resistant $Na_v1.5$ sodium channel, a key cardiac ion channel, can have profound effects on the duration and amplitude of the cardiac action potential and can result in arrhythmias and other heart malfunctions. To assess the potential cardiac liability of compounds at an early stage in the drug discovery process, a $Na_v1.5$ sodium channel screening assay was be performed on Molecular Device's PatchXpress™ automated electrophysiology platform. Under voltage-clamp conditions, $Na_v1.5$ currents were recorded from HEK cells expressing the human Nav1.5 channel in the absence and presence of increasing concentrations of the test compound to obtain an $IC_{50}$ value. The external recording solution contained (in mM): 90 TEACl, 50 NaCl, 1.8 CaCl, 1 $MgCl_2$, 10 HEPES, 10 glucose, adjusted to pH 7.4 with TEA-OH and to 300 mOsm with sucrose (if necessary), while the internal patch pipette solution contained (in mM): 129 CsF, 2 $MgCl_2$, 11 EGTA, 10 HEPES, 3 $Na_2ATP$ adjusted to pH 7.2 with CsOH and to 290 mOsm with sucrose (if necessary). $Na_v1.5$ channel currents were evoked using a cardiac action potential waveform at 1 Hz, digitized at 31.25 kHz and low-pass filtered at 12 kHz.

Voltage-Gated $Ca^{2+}$ Channels

The compounds described herein can also be studied as modulators of voltage-gated $Ca^{2+}$ channels (e.g., $Ca_v1.2$, $Ca_v2.2$, $Ca_v3.1$, or $Ca_v3.2$ channels). Exemplary methods are described herein.

A. Patch Clamp Methods

To record currents from $Ca_v3.2$ T-type $Ca^{2+}$ channels expressed in HEK cells, the culture media can be replaced with extracellular solution (ECS) containing (in mM): 142 CsCl, 10 D-glucose, 2 $CaCl_2$, 1 $MgCl_2$, 10 HEPES, pH adjusted to 7.4 with CsOH. Borosilicate glass patch pipettes, pulled on a P-97 micropipette puller (Sutter Instruments, Novato, Calif.) with typical resistances of 2-4 MW, can be backfilled with intracellular solution containing (in mM): 126.5 Cs-methanesulphonate, 2 $MgCl_2$, 10 HEPES, 11 EGTA, 2 Na-ATP, pH adjusted to 7.3 CsOH. Voltages were recorded in the whole-cell configuration at room temperature (~21° C.) using an Axopatch 200B (Molecular Devices, Sunnyvale, Calif.) patch-clamp amplifier. Recordings can be low-pass filtered at 1 kHz (−3 dB 4-pole Bessel filter), digitized at 2 kHz with a Digidata 1322A interface (Molecular Devices), and acquired using pClamp 9.2 (Molecular Devices), with no leak subtraction being used. Test compounds, prepared as 30 mM stock solutions in DMSO and diluted in extracellular buffer, can be applied through a gravity driven multi-barrelled array of capillaries (24 gauge) connected to reservoirs controlled by solenoid valves. The effects of compounds on $Ca_v3.2$ slow and fast inactivation can then be evaluated using different voltage protocols. The voltage dependence of fast and slow channel inactivation can be examined using a two pulse protocol. Data were analyzed and fitted using OriginPro v.7.5 (OriginLab, Northampton, Mass.) software.

B. High-Throughput $Ca_v2.2/K_{ir}2.3$ T-Type Fluorescent Assay

Cells were plated in 384-well, clear-bottom, black-walled, poly-D-lysine coated plates (Becton Dickinson, Franklin Lake, N.J.) 2 days prior to use in the FLIPR assay. 100 µL of cells ($1.4 \times 10^6$ cell/mL) containing doxycyline (Sigma-Aldrich, 1.5 µg/mL; to induce channel expression) were added to each well using a Multidrop (Thermo Scientific, Waltham, Mass.) and were maintained in 5% $CO_2$ incubator at 37° C. On the morning of the assay, cells were transferred to a 5% $CO_2$ incubator at 29° C.

Cells can then be washed with a wash buffer containing (in mM): 118 NaCl, 18.4 HEPES, 11.7 D-glucose, 2 $CaCl_2$, 0.5 $MgSO_4$, 4.7 KCl, 1.2 $KH_2PO_4$, pH adjusted to 7.2 with NaOH. 4.4 µM of the fluorescent indicator dye, Fluo-4 (Invitrogen), prepared in pluronic acid (Sigma-Aldrich), were loaded into the wells and incubated for 45 minutes at 29° C. in 5% $CO_2$. Cells were then rinsed with either a 2 mM KCl closed-state buffer (in mM: 138.5 NaCl, 10 HEPES, 10 D-glucose, 1 $CaCl_2$, and 2 KCl, with the pH adjusted to 7.4 with NaOH) when performing the closed-state assay or 12.5 mM KCl inactivated-state buffer (in mM: 128 NaCl, 10 HEPES, 10 D-glucose, 1 $CaCl_2$, and 12.5 mM KCl, with the pH adjusted to 7.4 with NaOH) when performing the inactivated-state assay.

Concentration-dependent response curves were generated from 5 mM stock solutions prepared in DMSO (Sigma-Aldrich) and diluted in either the 2 mM KCl buffer or 12.5 mM KCl buffer and incubated for 20 minutes at 29° C. in 5% $CO_2$. Calcium entry was evoked with an addition of 130 mM KCl stimulation buffer (in mM: 10.5 NaCl, 10 HEPES, 10 D-glucose, 1 $CaCl_2$, and 130 KCl, with the pH adjusted to 7.4 with NaOH) for both the closed-state or inactivated-state assay. A change in the Fluo-4 fluorescence signal was assessed using FLIPR$^{TETRA\text{™}}$ instrument (Molecular Devices, Sunnyvale, Calif.) for 3 minutes following the elevation of extracellular KCl using an illumination wavelength of 470-495 nm with emissions recorded at 515-575 nm.

Concentration-dependent response curves were obtained by comparing the fluorescence signal in the presence of compound and fitted with a logistic function (1) to obtain the concentration that inhibited 50% ($IC_{50}$) of the RLU signal using OriginPro v.7.5 software (OriginLab, Northampton, Mass.).

$$y = \left[ \frac{\max - \min}{1 + \left( \frac{[\text{drug}]}{IC_{50}} \right)^{n_H}} \right] + \min \quad (1)$$

To assess the quality of the FLIPR assays the Z-factor (2) were used to quantify the suitability of the assay conditions using the following equation:

$$Z = 1 - \frac{3SD_{sample} + 3SD_{control}}{mean_{sample} - mean_{control}} \quad (2)$$

Data were expressed as mean and standard deviation (SD).

C. High-Throughput $Ca_v3.1$ T-Type Fluorescent Assay

Cells were plated in 384-well, clear-bottom, black-walled, poly-D-lysine coated plates (Becton Dickinson, Franklin Lake, N.J.) 2 days prior to use in the FLIPR assay. 100 µL of cells ($2.0 \times 10^6$ cell/mL) containing doxycyline (Sigma-Aldrich, 1.5 µg/mL; to induce channel expression) were added to each well using a Multidrop (Thermo Scientific, Waltham, Mass.) and were maintained in 5% $CO_2$ incubator at 37° C. On the morning of the assay, cells were transferred to a 5% $CO_2$ incubator at 29° C.

Cells were washed with a wash buffer containing (in mM): 118 NaCl, 18.4 HEPES, 11.7 D-glucose, 0.05 $CaCl_2$, 0.5 $MgSO_4$, 1 KCl, and 1.2 $KH_2PO_4$, with the pH adjusted to 7.2 with NaOH. 4.4 µM of the fluorescent indicator dye, Fluo-4 (Invitrogen), prepared in pluronic acid (Sigma-Aldrich), were loaded into the wells and incubated for 45 minutes at 29° C. in 5% $CO_2$. Cells were then rinsed with the following low $Ca^{2+}$ buffer (in mM): 0.34 $Na_2HPO_4$, 4.2 $NaHCO_3$, 0.44 $KH_2PO_4$, 0.41 $MgSO_4$, 0.49 $MgCl_2\text{-}6H_2O$, 20 HEPES, 5.5 D-Glucose, 137 NaCl, 5.3 KCl, and 0.001 $CaCl_2$, with 0.1% BSA and the pH adjusted to 7.2 with NaOH. Concentration-dependent response curves were generated from 5 mM stock solutions prepared in DMSO (Sigma-Aldrich) and diluted in the buffer containing low $Ca^{2+}$ and incubated for 20 minutes at 29° C. in 5% $CO_2$ Calcium entry was evoked with an addition of (in mM): 0.34 $Na_2HPO_4$, 4.2 $NaHCO_3$, 0.44 $KH_2PO_4$, 0.41 $MgSO_4$, 0.49 $MgCl_2\text{-}6H_2O$, 20 HEPES, 5.5 D-Glucose, 137 NaCl, 5.3 KCl, and 6 $CaCl_2$, with 0.1% BSA and the pH adjusted to 7.2 with NaOH. A change in the Fluo-4 fluorescence signal was assessed using FLIPR$^{TETRA\text{™}}$ instrument (Molecular Devices, Sunnyvale, Calif.) for 3 minutes following the elevation of extracellular KCl using an illumination wavelength of 470-495 nm with emissions recorded at 515-575 nm.

Concentration-dependent response curves were obtained by comparing the fluorescence signal in the presence of compound and fitted with a logistic function (1) to obtain the concentration that inhibited 50% ($IC_{50}$) of the RLU signal using OriginPro v.7.5 software (OriginLab, Northampton, Mass.).

$$y = \left[ \frac{\max - \min}{1 + \left( \frac{[\text{drug}]}{IC_{50}} \right)^{n_H}} \right] + \min \quad (1)$$

To assess the quality of the FLIPR assays, the Z-factor (2) was used to quantify the suitability of the assay conditions using the following equation:

$$Z = 1 - \frac{3SD_{sample} + 3SD_{control}}{mean_{sample} - mean_{control}} \quad (2)$$

Data were expressed as mean and standard deviation (SD).

D. High-Throughput $Ca_v3.2/K_{ir}2.3$ T-Type Fluorescent Assay

Cells were plated in 384-well, clear-bottom, black-walled, poly-D-lysine coated plates (Becton Dickinson, Franklin Lake, N.J.) 2 days prior to use in the FLIPR assay. 100 µL of cells ($1.2 \times 10^6$ cell/mL) containing doxycyline (Sigma-Aldrich, 1.5 µg/mL; to induce channel expression) were added to each well using a Multidrop (Thermo Scientific, Waltham, Mass.) and were maintained in 5% $CO_2$ incubator at 37° C. On the morning of the assay, cells were transferred to a 5% $CO_2$ incubator at 29° C.

Cells were washed with a wash buffer containing (in mM): 118 NaCl, 18.4 HEPES, 11.7 D-glucose, 2 $CaCl_2$, 0.5 $MgSO_4$, 4.7 KCl, and 1.2 $KH_2PO_4$, with the pH adjusted to 7.2 with NaOH. 4.4 µM of the fluorescent indicator dye Fluo-4 (Invitrogen) prepared in pluronic acid (Sigma-Aldrich) were loaded into the wells and incubated for 45 minutes at 29° C. in 5% $CO_2$. Cells were then rinsed with either a 2 mM KCl closed-state buffer (in mM: 138.5 NaCl, 10 HEPES, 10 D-glucose, 1 $CaCl_2$, and 2 KCl, with the pH adjusted to 7.4 with NaOH) when performing the closed-state assay or 7.6 mM KCl inactivated-state buffer (in mM: 130.9 NaCl, 10 HEPES, 10 D-glucose, 1 $CaCl_2$, and 7.6 mM KCl, with the pH adjusted to 7.4 with NaOH) when performing the inactivated-state assay. Concentration-dependent response curves were generated from 5 mM stock solutions prepared in DMSO (Sigma-Aldrich), diluted in either the 2 mM KCl buffer or 7.6 mM KCl buffer, and incubated for 20 minutes at 29° C. in 5% $CO_2$. Calcium entry was evoked with an addition of either 12 mM KCl stimulation buffer (in mM: 128.5 NaCl, 10 HEPES, 10 D-glucose, 1 $CaCl_2$, and 12 KCl, with the pH adjusted to 7.4 with NaOH) or 14.5 mM KCl stimulation buffer (in mM: 126 NaCl, 10 HEPES, 10 D-glucose, 1 $CaCl_2$, and 14.5 KCl, with the pH adjusted to 7.4 with NaOH) for the closed-state or inactivated-state assay respectively. A change in the Fluo-4 fluorescence signal was assessed using FLIPR$^{TETRA™}$ instrument (Molecular Devices, Sunnyvale, Calif.) for 3 minutes following the elevation of extracellular KCl using an illumination wavelength of 470-495 nm with emissions recorded at 515-575 nm.

Concentration-dependent response curves were obtained by comparing the fluorescence signal in the presence of compound and fitted with a logistic function (1) to obtain the concentration that inhibited 50% ($IC_{50}$) of the RLU signal using OriginPro v.7.5 software (OriginLab, Northampton, Mass.).

$$y = \left[ \frac{\max - \min}{1 + \left(\frac{[\text{drug}]}{IC_{50}}\right)^{n_H}} \right] + \min \quad (1)$$

To assess the quality of the FLIPR assays, the Z-factor (2) was used to quantify the suitability of the assay conditions using the following equation:

$$Z = 1 - \frac{3SD_{sample} + 3SD_{control}}{mean_{sample} - mean_{control}} \quad (2)$$

Data were expressed as mean and standard deviation (SD).

E. High-Throughput $Ca_v1.2/K_{ir}2.3$ T-Type Fluorescent Assay

Cells were plated in 384-well, clear-bottom, black-walled, poly-D-lysine coated plates (Becton Dickinson, Franklin Lake, N.J.) 2 days prior to use in the FLIPR assay. 100 µL of cells (1.2×10$^6$ cell/mL) containing doxycyline (Sigma-Aldrich, 1.5 µg/mL; to induce channel expression) were added to each well using a Multidrop (Thermo Scientific, Waltham, Mass.) and were maintained in 5% $CO_2$ incubator at 37° C. On the morning of the assay, cells were transferred to a 5% $CO_2$ incubator at 29° C.

Cells were washed with a wash buffer containing (in mM): 118 NaCl, 18.4 HEPES, 11.7 D-glucose, 2 $CaCl_2$, 0.5 $MgSO_4$, 4.7 KCl, and 1.2 $KH_2PO_4$, with the pH adjusted to 7.2 with NaOH. 4.4 µM of the fluorescent indicator dye Fluo-4 (Invitrogen) prepared in pluronic acid (Sigma-Aldrich) were loaded into the wells and incubated for 45 minutes at 29° C. in 5% $CO_2$. Cells were then rinsed with either a 2 mM KCl closed-state buffer (in mM: 138.5 NaCl, 10 HEPES, 10 D-glucose, 1 $CaCl_2$, and 2 KCl, with the pH adjusted to 7.4 with NaOH) when performing the closed-state assay or 30 mM KCl inactivated-state buffer (in mM: 110.5 NaCl, 10 HEPES, 10 D-glucose, 1 $CaCl_2$, and 30 mM KCl, with the pH adjusted to 7.4 with NaOH) when performing the inactivated-state assay. Concentration-dependent response curves were generated from 5 mM stock solutions prepared in DMSO (Sigma-Aldrich), diluted in either the 2 mM KCl buffer or 30 mM KCl buffer, and incubated for 20 minutes at 29° C. in 5% $CO_2$. Calcium entry was evoked with an addition of 130 mM KCl stimulation buffer (in mM: 10.5 NaCl, 10 HEPES, 10 D-glucose, 1 $CaCl_2$, and 130 KCl, with the pH adjusted to 7.4 with NaOH). A change in the Fluo-4 fluorescence signal was assessed using FLIPR$^{TETRA™}$ instrument (Molecular Devices, Sunnyvale, Calif.) for 3 minutes following the elevation of extracellular KCl using an illumination wavelength of 470-495 nm with emissions recorded at 515-575 nm.

Concentration-dependent response curves were obtained by comparing the fluorescence signal in the presence of compound and fitted with a logistic function (1) to obtain the concentration that inhibited 50% ($IC_{50}$) of the RLU signal using OriginPro v.7.5 software (OriginLab, Northampton, Mass.).

$$y = \left[ \frac{\max - \min}{1 + \left(\frac{[\text{drug}]}{IC_{50}}\right)^{n_H}} \right] + \min \quad (1)$$

To assess the quality of the FLIPR assays, the Z-factor (2) was used to quantify the suitability of the assay conditions using the following equation:

$$Z = 1 - \frac{3SD_{sample} + 3SD_{control}}{mean_{sample} - mean_{control}} \quad (2)$$

Data were expressed as mean and standard deviation (SD).

hERG $K^+$ Channel Activity

It may be desirable that the compound has very low activity with respect to the hERG $K^+$ channel, which is expressed in the heart: compounds that block this channel with high potency may cause reactions which are fatal. See, e.g., Bowlby et al., "hERG (KCNH2 or $K_v11.1$ $K^+$ Channels: Screening for Cardiac Arrhythmia Risk," *Curr. Drug Metab.* 9(9):965-70 (2008)). Thus, for a compound that modulates, e.g., sodium channel activity, it may also be shown that the hERG $K^4$ channel is not inhibited or only minimally inhibited as compared to the inhibition of the primary channel targeted. Such compounds may be particularly useful in the methods described herein.

Compounds were tested using a standard electrophysiological assay (see Kiss et al., *Assay & Drug Development Technologies*, 1:1-2, 2003, and Bridgland-Taylor et al., *Journal of Pharmacological and Toxicological Methods*, 54:189-199, 2006). Briefly, compounds were tested at 3 µM using IonWorks and the percent inhibition of the peak of the slowly deactivating hERG tail current was used to assess the affinity.

Pain Models

L5/L6 Spinal Nerve Ligation (SNL)—Chung Pain Model

The Spinal Nerve Ligation is an animal model representing peripheral nerve injury generating a neuropathic pain syndrome. In this model experimental animals develop the clinical symptoms of tactile allodynia and hyperalgesia. L5/L6 Spinal nerve ligation (SNL) injury was induced using the procedure of Kim and Chung (Kim et al., *Pain* 50:355-363 (1992)) in male Sprague-Dawley rats (Harlan; Indianapolis, Ind.) weighing 200 to 250 grams. An exemplary protocol is provided below The animals were anesthetized with isoflurane, the left L6 transverse process was removed, and the L5 and L6 spinal nerves were tightly ligated with 6-0 silk suture. The wound was closed with internal sutures and external tissue adhesive. Rats that exhibit motor deficiency (such as paw-dragging) or failure to exhibit subsequent tactile allodynia can be excluded from further testing.

Sham control rats can undergo the same operation and handling as the experimental animals, but without SNL.

Assessment of Mechanical Hyperalgesia

Baseline and post-treatment values for mechanical hyperalgesia were evaluated using a digital Randall-Selitto device (dRS; IITC Life Sciences, Woodland Hills, Calif.). Animals were allowed to acclimate to the testing room for a minimum of 30 minutes before testing. Animals were placed in a restraint sling that suspends the animal, leaving the hind limbs available for testing. Paw compression threshold was measured once at each time point for the ipsilateral and contralateral paws. The stimulus was applied to the plantar surface of the hind paw by a dome-shaped tip placed between the 3rd and 4th metatarsus, and pressure was applied gradually over approximately 10 seconds. Measurements are taken from the first observed nocifensive behavior of vocalization, struggle or withdrawal. A cut-off value of 300 g was used to prevent injury to the animal. The mean and standard error of the mean (SEM) were determined for each paw for each treatment group. Fourteen days after surgery, mechanical hyperalgesia was assessed and rats were assigned to treatment groups based on pre-treatment baseline values. Prior to initiating drug delivery, baseline behavioural testing data can be obtained. At selected times after infusion of the Test or Control Article behavioural data can then be collected again.

Exemplary data are shown in FIGS. 2A-2C and 3A-3C for select compounds of the invention. Additional data are presented in Tables 2-4 below.

Table 2 shows Compound (1) and Compound (41) (30 mg/kg, p.o.) significantly decreased mechanical hyperalgesia at 2 and 4 hours after administration compared to vehicle treated animals. Compound (24) (30 mg/kg, p.o.) had no significant effect on mechanical hyperalgesia at any time point tested compared to vehicle treated animals.

Table 3 shows that administration of Compound (33) (30 mg/kg, p.o.) significantly decreased mechanical hyperalgesia at 1, 2 and 4 hours after administration compared to vehicle treated animals. Administration of Compound (56), Compound (31) or Compound (34) (30 mg/kg, p.o.) significantly decreased mechanical hyperalgesia 2 and 4 hours after administration compared to vehicle treated animals. Administration of Compound (36) (30 mg/kg, p.o.) had no significant effect on mechanical hyperalgesia at any time point tested compared to vehicle treated animals.

TABLE 2

| Compound | Response Threshold (g) | | | % Reversal | | | % Gabapentin Peak |
|---|---|---|---|---|---|---|---|
| | 1 hr | 2 hr | 4 hr | 1 hr | 2 hr | 4 hr | |
| Gabapentin (100 mg/kg; p.o.) | 129.0 | 154.6 | 135.7 | 359. | 55.3 | 41.0 | — |
| DMA/PS80/PEG400 (10:45:45, 2 mL/kg, p.o.) | 90.9 | 85.1 | 84.6 | 5.4 | 0.8 | 0.4 | 1.4 |
| Compound (1) (30 mg/kg, p.o.) | 93.8 | 120.6 | 113.3 | 9.2 | 30.2 | 24.4 | 54.7 |
| Compound (24) (30 mg/kg, p.o.) | 84.0 | 118.4 | 116.6 | 0.8 | 27.9 | 26.5 | 50.5 |
| Compound (41) (30 mg/kg, p.o.) | 99.6 | 108.3 | 109.0 | 13.8 | 20.7 | 21.3 | 37.5 |

TABLE 3

| Compound | Response Threshold (g) | | | % Reversal | | | % Gabapentin Peak |
|---|---|---|---|---|---|---|---|
| | 1 hr | 2 hr | 4 hr | 1 hr | 2 hr | 4 hr | |
| Gabapentin (100 mg/kg; p.o.) | 113.5 | 153.8 | 169.3 | 22.9 | 61.0 | 75.7 | — |
| DMA/PS80/PEG400 (10:45:45, 2 mL/kg, p.o.) | 87.8 | 85.5 | 83.2 | −0.2 | −2.2 | −4.3 | −3.7 |
| Compound (31) (30 mg/kg, p.o.) | 107.9 | 139.0 | 109.9 | 17.2 | 48.0 | 19.2 | 78.7 |
| Compound (33) (30 mg/kg, p.o.) | 113.6 | 136.9 | 150.8 | 22.4 | 44.7 | 58.1 | 73.3 |
| Compound (34) (30 mg/kg, p.o.) | 104.5 | 144.8 | 132.4 | 15.3 | 54.2 | 42.3 | 88.9 |
| Compound (56) (30 mg/kg, p.o.) | 110.8 | 131.4 | 140.4 | 19.8 | 40.4 | 49.4 | 66.2 |

TABLE 3-continued

| Compound | Response Threshold (g) | | | % Reversal | | | % Gabapentin Peak |
|---|---|---|---|---|---|---|---|
| | 1 hr | 2 hr | 4 hr | 1 hr | 2 hr | 4 hr | |
| Compound (36) (30 mg/kg, p.o.) | 87.8 | 107.0 | 112.3 | −0.5 | 18.6 | 23.8 | 30.5 |

Figure 2C:
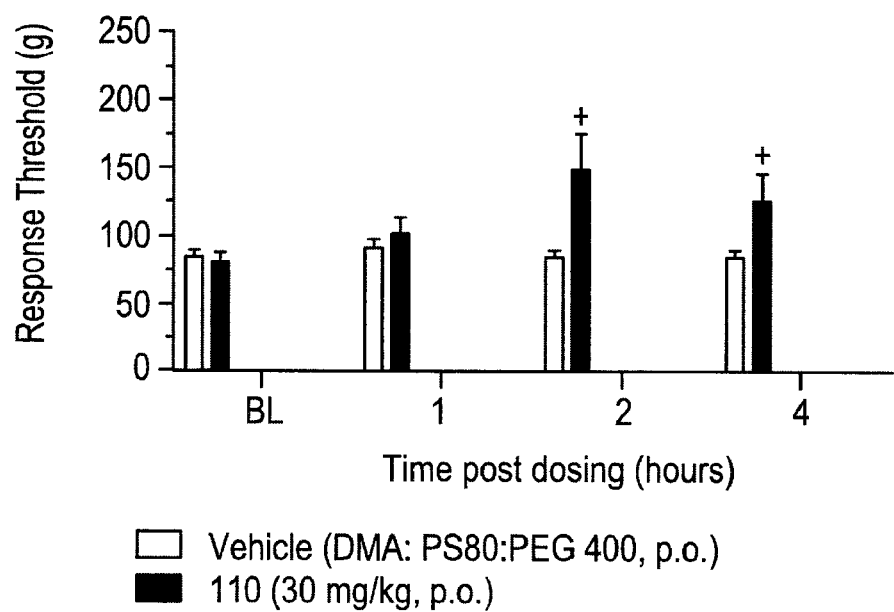
Figure 3C:
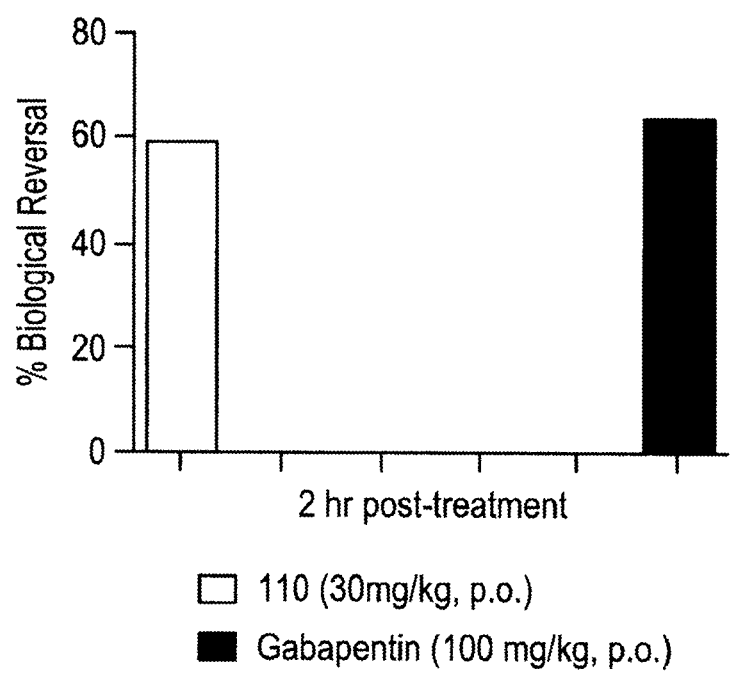

Exemplary data are also shown in FIG. 2C and FIG. 3C for Compound (110) and in Table 4 below. Compound (110) is shown to significantly decrease mechanical hyperalgesia at two and four hours after administration compared to vehicle treated animals.

TABLE 4

| Compound | Response Threshold (g) | | | % Reversal | | | % Gabapentin Peak |
|---|---|---|---|---|---|---|---|
| | 1 hr | 2 hr | 4 hr | 1 hr | 2 hr | 4 hr | |
| Gabapentin (100 mg/kg; p.o.) | 129.0 | 154.6 | 135.7 | 359. | 55.3 | 41.0 | — |
| DMA/PS80/PEG400 (10:45:45, 2 mL/kg, p.o.) | 90.9 | 85.1 | 84.6 | 5.4 | 0.8 | 0.4 | 1.4 |
| Compound (110) (30 mg/kg, p.o.) | 100.6 | 148.5 | 126.1 | 14.6 | 51.2 | 34.1 | 92.7 |

Assessment of Tactile Allodynia—Von Frey

The assessment of tactile allodynia can consist of measuring the withdrawal threshold of the paw ipsilateral to the site of nerve injury in response to probing with a series of calibrated von Frey filaments (innocuous stimuli). Animals can be acclimated to the suspended wire-mesh cages for 30 min before testing. Each von Frey filament can be applied perpendicularly to the plantar surface of the ligated paw of rats for 5 sec. A positive response can be indicated by a sharp withdrawal of the paw. For rats, the first testing filament is 4.31. Measurements can be taken before and after administration of test articles. The paw withdrawal threshold can be determined by the non-parametric method of Dixon (Dixon, *Ann. Rev. Pharmacol. Toxicol.* 20:441-462 (1980)), in which the stimulus was incrementally increased until a positive response was obtained, and then decreased until a negative result was observed. The protocol can be repeated until three changes in behaviour were determined ("up and down" method; Chaplan et al., *J. Neurosci. Methods* 53:55-63 (1994)). The 50% paw withdrawal threshold can be determined as $(10^{[Xf+k\delta]})/10,000$, where $X_f$=the value of the last von Frey filament employed, k=Dixon value for the positive/negative pattern, and $\delta$=the logarithmic difference between stimuli. The cut-off values for rats can be, for example, no less than 0.2 g and no higher than 15 g (5.18 filament); for mice no less than 0.03 g and no higher than 2.34 g (4.56 filament). A significant drop of the paw withdrawal threshold compared to the pre-treatment baseline is considered tactile allodynia. Rat SNL tactile allodynia can be tested for the compounds described herein at, e.g., 60 minutes compared to baseline and post-SNL.

Assessment of Thermal Hypersensitivity—Hargreaves

The method of Hargreaves and colleagues (Hargreaves et al., *Pain* 32:77-8 (1988)) can be employed to assess paw-withdrawal latency to a noxious thermal stimulus.

Rats may be allowed to acclimate within a Plexiglas enclosure on a clear glass plate for 30 minutes. A radiant heat source (e.g., halogen bulb coupled to an infrared filter) can then be activated with a timer and focused onto the plantar surface of the affected paw of treated rats. Paw-withdrawal latency can be determined by a photocell that halts both lamp and timer when the paw is withdrawn. The latency to withdrawal of the paw from the radiant heat source can be determined prior to L5/L6 SNL, 7-14 days after L5/L6 SNL but before drug, as well as after drug administration. A maximal cut-off of 33 seconds is typically employed to prevent tissue damage. Paw withdrawal latency can be thus determined to the nearest 0.1 second. A significant drop of the paw withdrawal latency from the baseline indicates the status of thermal hyperalgesia. Antinociception is indicated by a reversal of thermal hyperalgesia to the pre-treatment baseline or a significant (p<0.05) increase in paw withdrawal latency above this baseline. Data is converted to % anti hyperalgesia or % anti nociception by the formula: (100×(test latency−baseline latency)/(cut-off−baseline latency) where cut-off is 21 seconds for determining anti hyperalgesia and 40 seconds for determining anti nociception.

Epilepsy Models

6 Hz Psychomotor Seizure Model of Partial Epilepsy

Compounds can be evaluated for the protection against seizures induced by a 6 Hz, 0.2 ms rectangular pulse width of 3 s duration, at a stimulus intensity of 32 mA (CC97) applied to the cornea of male CF1 mice (20-30 g) according to procedures described by Barton et al, "Pharmacological Characterization of the 6 Hz Psychomotor Seizure Model of Partial Epilepsy," *Epilepsy Res.* 47(3):217-27 (2001). Seizures are characterised by the expression of one or more of the following behaviours: stun, forelimb clonus, twitching of the vibrissae and Straub-tail immediately following electrical stimulation. Animals can be considered "protected" if, following pre-treatment with a compound, the 6 Hz stimulus failed to evoke a behavioural response as describe above.

GAERS (Genetic Absence Epilepsy Rats from Strasbourg) Epilepsy Model

The GAERS (Genetic Absence Epilepsy Rats from Strasbourg) is noted for its long and frequently recurring absence seizure episodes. Investigators have determined, using electrophysiological recordings from neurons within the thalamus, that the activity and expression of the low-voltage calcium channels is significantly increased in GAERS. Eight female GAERS rats, bred in the Ludwig Institute for Cancer Research, were used for this study. Rats weighed between 180 and 250 g and aged between 18 and 26 weeks at the start of the experiment. Methods for conducting this assay are known in the art.

Assessments of Neurological or Muscular Impairments

To assess a compound's undesirable side effects (toxicity), animals can be monitored for overt signs of impaired neurological or muscular function. In mice, the rotarod procedure (Dunham et al., J. Am. Pharmacol. Assoc. 46:208-209 (1957)) is used to disclose minimal muscular or neurological impairment (MMI). When a mouse is placed on a rod that rotates at a speed of 6 rpm, the animal can maintain its equilibrium for long periods of time. The animal is considered toxic if it falls off this rotating rod three times during a 1-min period. In addition to MMI, animals may exhibit a circular or zigzag gait, abnormal body posture and spread of the legs, tremors, hyperactivity, lack of exploratory behavior, somnolence, stupor, catalepsy, loss of placing response and changes in muscle tone.

Recordings on Lamina I/II Spinal Cord Neurons

Male Wistar rats (P6 to P9 for voltage-clamp and P15 to P18 for current-clamp recordings) can be anaesthetized through intraperitoneal injection of Inactin (Sigma). The spinal cord can then be rapidly dissected out and placed in an ice-cold solution protective sucrose solution containing (in mM): 50 sucrose, 92 NaCl, 15 D-Glucose, 26 $NaHCO_3$, 5 KCl, 1.25 $NaH_2PO_4$, 0.5 $CaCl_2$, 7 $MgSO_4$, 1 kynurenic acid, and bubbled with 5% $CO_2$/95% $O_2$. The meninges, dura, and dorsal and ventral roots can then removed from the lumbar region of the spinal cord under a dissecting microscope. The "cleaned" lumbar region of the spinal cord may be glued to the vibratome stage and immediately immersed in ice cold, bubbled, sucrose solution. For current-clamp recordings, 300 to 350 μm parasagittal slices can be cut to preserve the dendritic arbour of lamina I neurons, while 350 to 400 μm transverse slices can be prepared for voltage-clamped $Na_v$ channel recordings. Slices may be allowed to recover for 1 hour at 35° C. in Ringer solution containing (in mM): 125 NaCl, 20 D-Glucose, 26 $NaHCO_3$, 3 KCl, 1.25 $NaH_2PO_4$, 2 $CaCl_2$, 1 $MgCl_2$, 1 kynurenic acid, 0.1 picrotoxin, bubbled with 5% $CO_2$/95% $O_2$. The slice recovery chamber can then returned to room temperature (20 to 22° C.) for recordings.

Neurons may be visualized using IR-DIC optics (Zeiss Axioskop 2 FS plus, Gottingen, Germany), and neurons from lamina I and the outer layer of lamina II can be selected based on their location relative to the substantia gelatinosa layer. Neurons can be patch-clamped using borosilicate glass patch pipettes with resistances of 3 to 6 MW. Current-clamp recordings of lamina I/II neurons in the intact slice, the external recording solution was the above Ringer solution, while the internal patch pipette solution contained (in mM): 140 KGluconate, 4 NaCl, 10 HEPES, 1 EGTA, 0.5 $MgCl_2$, 4 MgATP, 0.5 $Na_2$GTP, adjusted to pH 7.2 with 5 M KOH and to 290 mOsm with D-Mannitol (if necessary). Tonic firing neurons can be selected for current-clamp experiments, while phasic, delayed onset and single spike neurons may be discarded (22). Recordings can be digitized at 50 kHz and low-pass filtered at 2.4 kHz.

Pharmacokinetic Parameters

Preliminary exposure characteristics of the compounds can be evaluated using, e.g., an in vivo Rat Early Pharmacokinetic (EPK) study design to show bioavailability. For example, Male Sprague-Dawley rats can be dosed via oral (PO) gavage in a particular formulation. Blood samples can then be collected from the animals at 6 timepoints out to 4 hours post-dose. Pharmacokinetic analysis can then performed on the LC-MS/MS measured concentrations for each timepoint of each compound.

Other Embodiments

While the invention has been described in connection with specific embodiments thereof, it will be understood that it is capable of further modifications and this application is intended to cover any variations, uses, or adaptations of the invention following, in general, the principles of the invention and including such departures from the present disclosure come within known or customary practice within the art to which the invention pertains and may be applied to the essential features hereinbefore set forth.

All publications, patents and patent applications are herein incorporated by reference in their entirety to the same extent as if each individual publication, patent or patent application was specifically and individually indicated to be incorporated by reference in its entirety.

What is claimed is:

1. A compound selected from the group consisting of

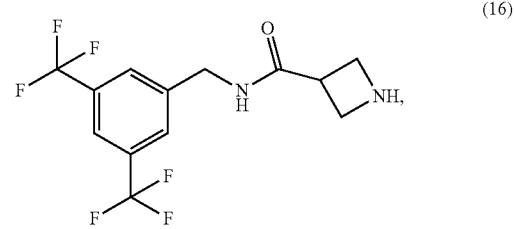

(16)

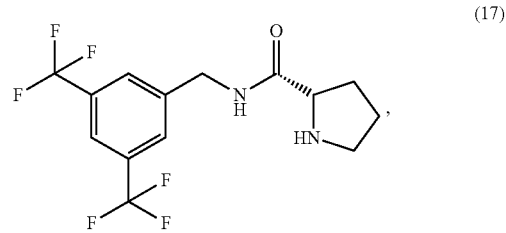

(17)

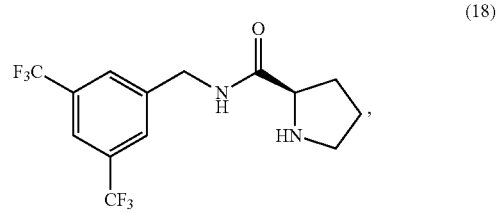

(18)

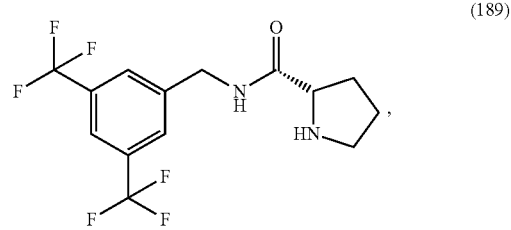

(189)

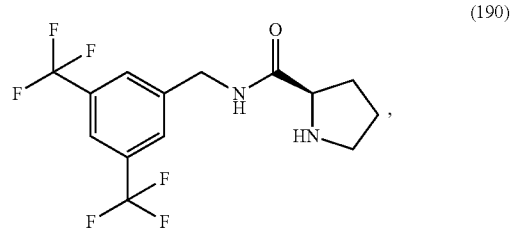

(190)

(194) 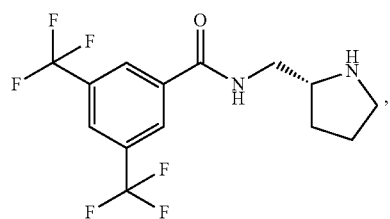
(195) 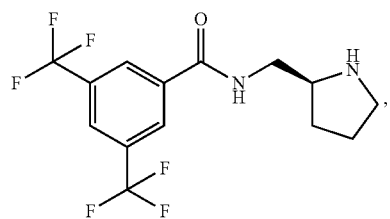
(199) 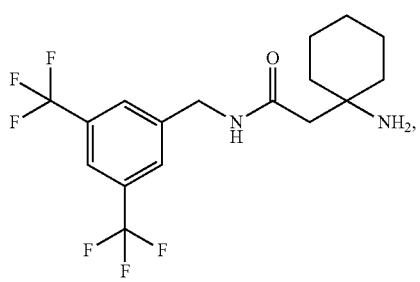
(200) 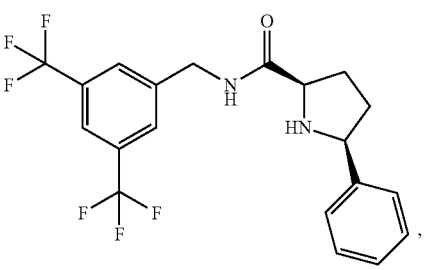
(203) 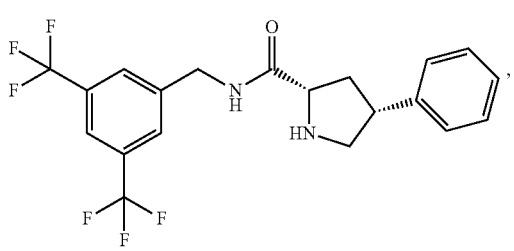
(204) 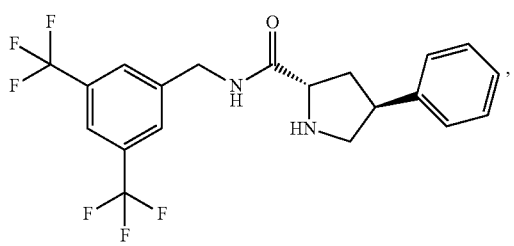
(205) 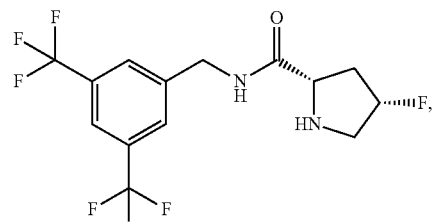
(206) 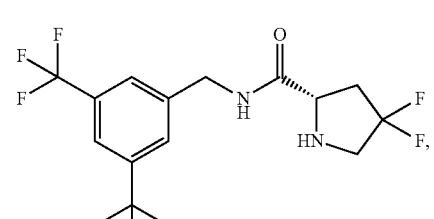
(207) 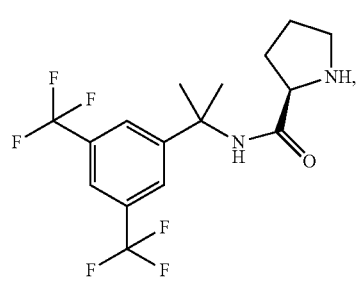
(208) 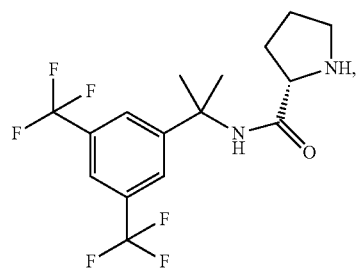
(209) 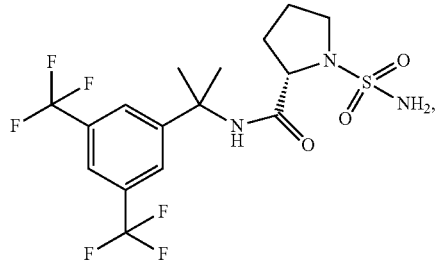
(210) 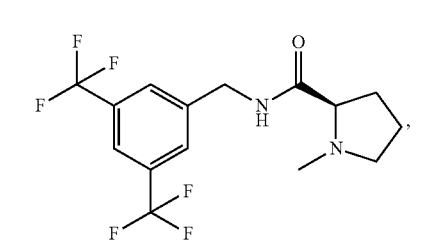

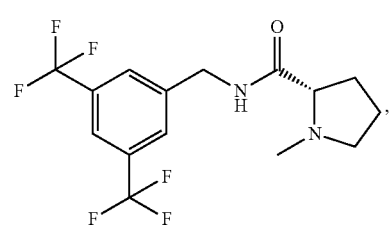 (211)
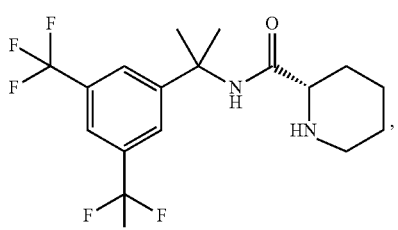 (212)
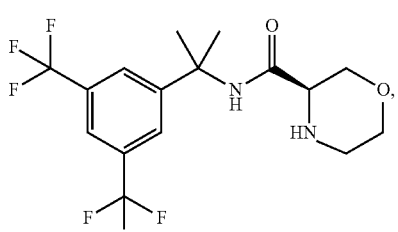 (213)
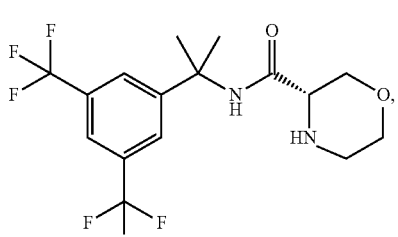 (214)
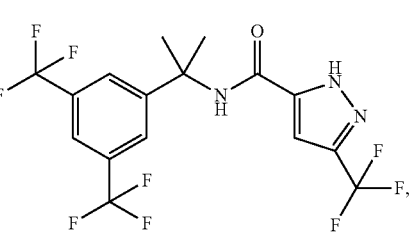 (215)
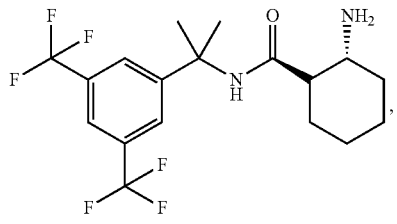 (216)
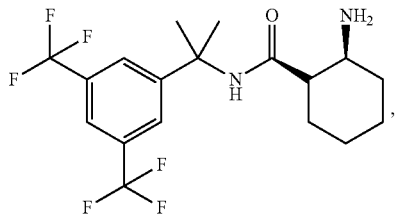 (217)
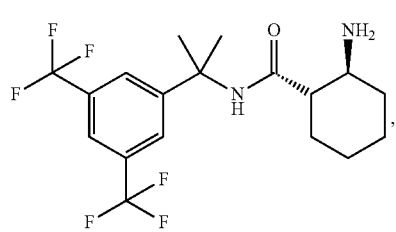 (218)
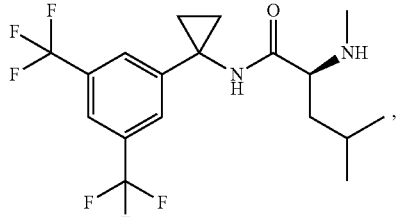 (219)
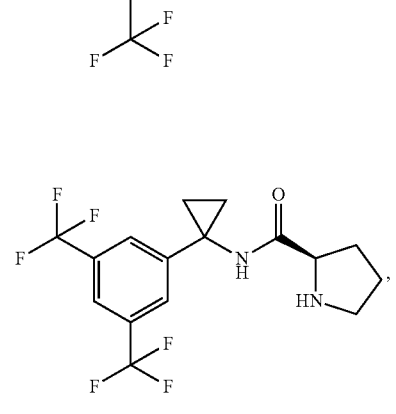 (220)
(221)
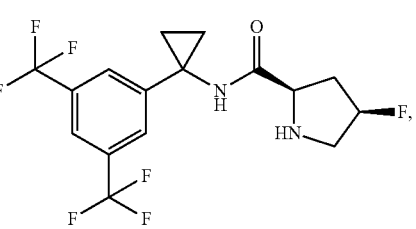 (222)
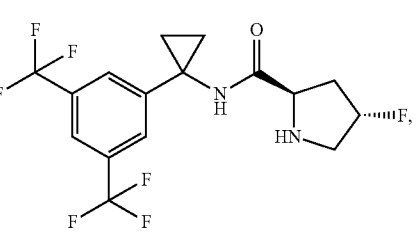 (223)

(224) 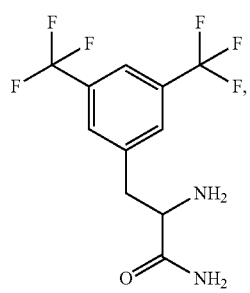
(234) 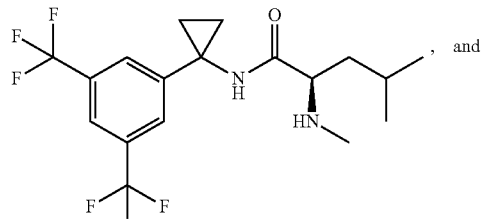, and
(225) 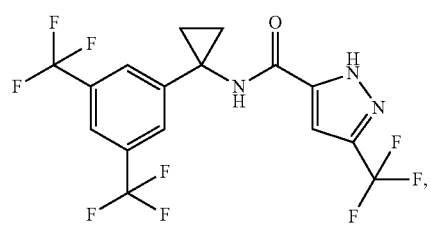
(228) 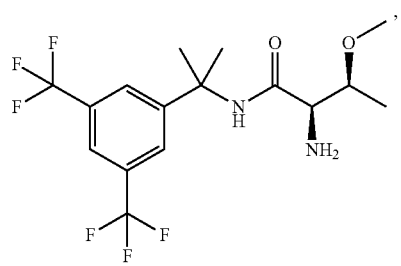
(236) 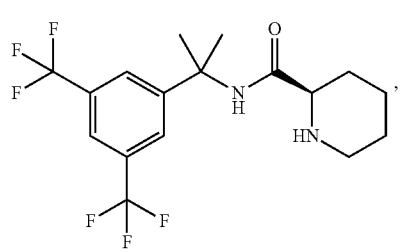
or a pharmaceutically acceptable salt or solvate thereof.
2. The compound of claim 1, selected from the group consisting of
(231) 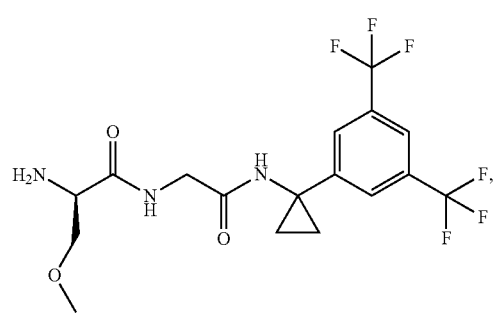
(205) 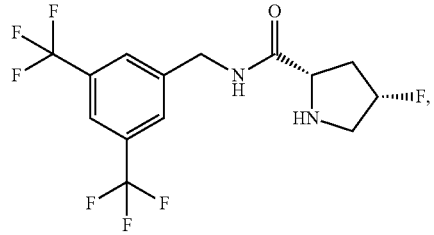
(208) 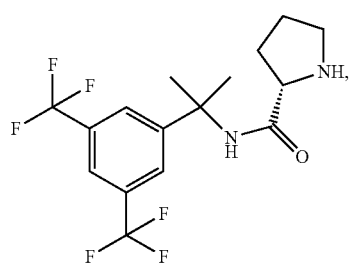
(232) 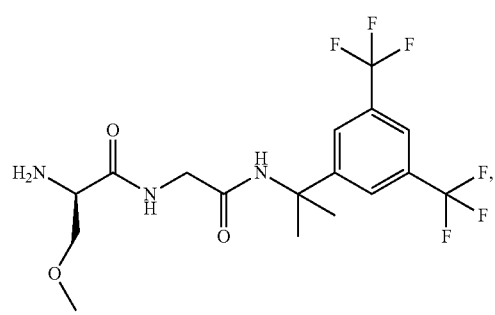
(190) 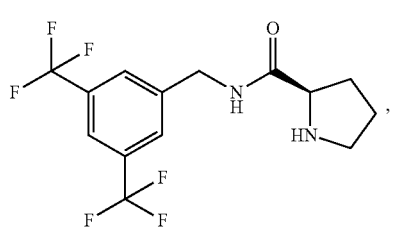

-continued (211)

(203)

(204)

(223)

or a pharmaceutically acceptable salt or solvate thereof.

3. A pharmaceutical composition comprising the compound of claim 1 and a pharmaceutically acceptable carrier or excipient.

4. The pharmaceutical composition of claim 3, wherein said pharmaceutical composition is formulated in unit dosage form.

5. The pharmaceutical composition of claim 4, wherein said unit dosage form is a tablet, caplet, capsule, lozenge, film, strip, gelcap, or syrup.

6. A compound selected from the group consisting of:

(196)

-continued (197)

(227)

(229)

(230)

(233)

and

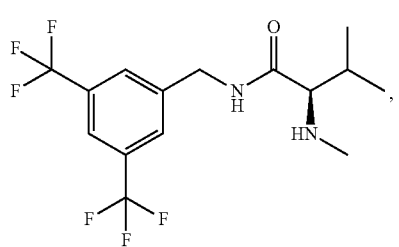
(235)
or a pharmaceutically acceptable salt or solvate thereof.
\* \* \* \* \*